US011858995B2

(12) United States Patent
Elliott et al.

(10) Patent No.: US 11,858,995 B2
(45) Date of Patent: Jan. 2, 2024

(54) BISPECIFIC ANTIBODIES AGAINST CD3 AND CD20 FOR TREATING CHRONIC LYMPHOCYTIC LEUKEMIA

(71) Applicant: GENMAB A/S, Valby (DK)

(72) Inventors: Brian Elliott, Hoboken, NJ (US); Jenny Jianlin Chen, East Hanover, NJ (US); Tahamtan Ahmadi, Rydal, PA (US); Christopher W. L. Chiu, Warren, NJ (US); Esther C. W. Breij, Driebergen (NL); Ida Hiemstra, Utrecht (NL); Maria N. Jure-Kunkel, Plainsboro, NJ (US)

(73) Assignee: GENMAB A/S, Valby (DK)

( * ) Notice: Subject to any disclaimer, the term of this patent is extended or adjusted under 35 U.S.C. 154(b) by 0 days.

(21) Appl. No.: 17/559,935

(22) Filed: Dec. 22, 2021

(65) Prior Publication Data

US 2022/0112287 A1 Apr. 14, 2022

Related U.S. Application Data

(63) Continuation of application No. 17/471,861, filed on Sep. 10, 2021, now abandoned.

(60) Provisional application No. 63/076,733, filed on Sep. 10, 2020.

(51) Int. Cl.
*A61K 39/00* (2006.01)
*C07K 16/28* (2006.01)

(52) U.S. Cl.
CPC ...... *C07K 16/2809* (2013.01); *C07K 16/2887* (2013.01); *A61K 2039/507* (2013.01); *A61K 2039/545* (2013.01); *C07K 2317/24* (2013.01); *C07K 2317/31* (2013.01)

(58) Field of Classification Search
None
See application file for complete search history.

(56) References Cited

U.S. PATENT DOCUMENTS

| 4,946,778 | A | 8/1990 | Ladner et al. |
|---|---|---|---|
| 5,589,466 | A | 12/1996 | Felgner et al. |
| 5,731,168 | A | 3/1998 | Carter et al. |
| 5,736,137 | A | 4/1998 | Anderson et al. |
| 5,739,277 | A | 4/1998 | Presta et al. |
| 5,973,972 | A | 10/1999 | Kwon et al. |
| 6,077,835 | A | 6/2000 | Hanson et al. |
| 7,262,028 | B2 | 8/2007 | Van Berkel et al. |
| 7,375,118 | B2 | 5/2008 | Sircar et al. |
| 7,612,181 | B2 | 11/2009 | Wu et al. |
| 7,951,918 | B2 | 5/2011 | Glaser et al. |
| 8,236,308 | B2 | 8/2012 | Kischel et al. |
| 9,150,663 | B2 | 10/2015 | Labrijn et al. |
| 9,212,230 | B2 | 12/2015 | Schuurman et al. |
| 10,273,227 | B2 | 4/2019 | Kettle et al. |
| 10,344,050 | B2 | 7/2019 | Gramer et al. |
| 10,407,501 | B2 | 9/2019 | Van Den Brink et al. |
| 10,465,006 | B2 | 11/2019 | Van Den Brink et al. |
| 10,544,220 | B2 | 1/2020 | Engelberts et al. |
| 10,590,206 | B2 | 3/2020 | Labrijn et al. |
| 10,597,464 | B2 | 3/2020 | Labrijn et al. |
| 10,906,991 | B2 | 2/2021 | Schuurman et al. |
| 11,180,572 | B2 | 11/2021 | De Jong et al. |
| 11,359,015 | B2 | 6/2022 | Rademaker et al. |
| 11,485,796 | B2 | 11/2022 | Labrijn et al. |
| 11,492,371 | B2 | 11/2022 | Gramer et al. |
| 11,535,679 | B2 | 12/2022 | Elliott et al. |
| 11,548,952 | B2 | 1/2023 | Elliott et al. |
| 11,608,383 | B2 | 3/2023 | Elliott et al. |
| 11,613,575 | B2 | 3/2023 | Van Den Brink et al. |
| 2004/0167319 | A1 | 8/2004 | Teeling et al. |
| 2010/0105874 | A1 | 4/2010 | Schuurman et al. |
| 2010/0155133 | A1 | 6/2010 | Makwinski et al. |
| 2011/0275787 | A1 | 11/2011 | Kufer et al. |
| 2013/0039913 | A1 | 2/2013 | Labrijn et al. |
| 2013/0216556 | A1 | 8/2013 | Fowler et al. |
| 2014/0088295 | A1 | 3/2014 | Smith et al. |
| 2014/0112914 | A1 | 4/2014 | Nezu et al. |
| 2014/0303356 | A1 | 10/2014 | Gramer et al. |
| 2015/0071943 | A1 | 3/2015 | Bishop et al. |
| 2015/0166661 | A1 | 6/2015 | Chen et al. |
| 2015/0175707 | A1 | 6/2015 | De Jong et al. |
| 2015/0209430 | A1 | 7/2015 | Benedict et al. |
| 2015/0225479 | A1 | 8/2015 | Huille et al. |
| 2015/0337049 | A1 | 11/2015 | Labrijn et al. |
| 2016/0046727 | A1 | 2/2016 | Labrijn et al. |
| 2016/0159930 | A1 | 6/2016 | Schuurman et al. |
| 2016/0168247 | A1 | 6/2016 | Van Den Brink et al. |

(Continued)

FOREIGN PATENT DOCUMENTS

| CN | 102250246 A | 11/2011 |
|---|---|---|
| CN | 104922688 A | 9/2015 |

(Continued)

OTHER PUBLICATIONS

Genbank locus IGKC_Human, P01834.2, Aug. 12, 2020, pp. 1-6. (Year: 2020).*
NCT04358458, pp. 1-7, Apr. 20, 2020. (Year: 2020).*
U.S. Department of Health and Human Services, FDA, Center for Drug Evaluation and Research (CDER), Jul. 2005, pp. i-iii and 1-27. (Year: 2005).*
ASCO Post Staff, "Will Bispecific Antibodies Compete With CAR T-Cell Therapy in Lymphoma?," pp. 1-5, Feb. 25, 2020. (Year: 2020).*
Hampel et al. (Leuk Lymphoma. Nov. 2019 ; 60(11): 2712-2719). (Year: 2019).*
ASCO Post Staff, "Will Bispecific Antibodies Compete With CAR T-Cell Therapy in Lymphoma?," pp. 1-7, Feb. 25, 2020. (Year: 2020).*

(Continued)

*Primary Examiner* — Zachary S Skelding
(74) *Attorney, Agent, or Firm* — Nelson Mullins Riley & Scarborough LLP; Jane E. Remillard, Esq.; Cynthia L. Kanik

(57) ABSTRACT

Provided are methods of clinical treatment of chronic lymphoblastic leukemia (CLL) in human subjects using a bispecific antibody which binds to CD3 and CD20.

28 Claims, 2 Drawing Sheets
Specification includes a Sequence Listing.

(56) References Cited

U.S. PATENT DOCUMENTS

| | | |
|---|---|---|
| 2016/0199399 A1 | 7/2016 | Knudsen |
| 2016/0333095 A1 | 11/2016 | Van Den Brink et al. |
| 2017/0233497 A1 | 8/2017 | Labrijn et al. |
| 2017/0349657 A1 | 12/2017 | Saville et al. |
| 2017/0355767 A1 | 12/2017 | Engelberts et al. |
| 2018/0134798 A1* | 5/2018 | Chu .................. C07K 16/2866 |
| 2019/0284278 A1 | 9/2019 | Rademaker et al. |
| 2020/0048304 A1 | 2/2020 | Gramer et al. |
| 2020/0123255 A1 | 4/2020 | Van Den Brink et al. |
| 2020/0199229 A1 | 6/2020 | Van Den Brink et al. |
| 2020/0199231 A1 | 6/2020 | Engelberts et al. |
| 2020/0262932 A1 | 8/2020 | Labrijn et al. |
| 2020/0332022 A1 | 10/2020 | Labrijn et al. |
| 2021/0032358 A1 | 2/2021 | Valbjoern et al. |
| 2021/0230301 A1 | 7/2021 | De Jong et al. |
| 2021/0371538 A1 | 12/2021 | Ahmadi et al. |
| 2022/0088070 A1 | 3/2022 | Albertson et al. |
| 2022/0112300 A1 | 4/2022 | Elliott et al. |
| 2022/0112301 A1 | 4/2022 | Elliott et al. |
| 2022/0112309 A1 | 4/2022 | Elliott et al. |
| 2022/0119544 A1 | 4/2022 | Elliott et al. |
| 2022/0144964 A1 | 5/2022 | Elliott et al. |
| 2022/0380464 A1 | 12/2022 | Rademaker et al. |
| 2022/0389101 A1 | 12/2022 | Rademaker et al. |
| 2022/0411505 A1 | 12/2022 | Valbjoern et al. |

FOREIGN PATENT DOCUMENTS

| | | |
|---|---|---|
| EP | 0 629 240 A1 | 12/1994 |
| EP | 1870459 A1 | 12/2007 |
| WO | 92/22653 A1 | 12/1992 |
| WO | 9850431 A2 | 11/1998 |
| WO | 2000/46147 A2 | 8/2000 |
| WO | 00/70087 A1 | 11/2000 |
| WO | 2003/074569 A2 | 9/2003 |
| WO | 2004/035607 A2 | 4/2004 |
| WO | 2005/004809 A2 | 1/2005 |
| WO | 2005/061547 A2 | 7/2005 |
| WO | 2005/103081 A2 | 11/2005 |
| WO | 2007/042261 A2 | 4/2007 |
| WO | 2007/059782 A1 | 5/2007 |
| WO | 2007110205 A2 | 10/2007 |
| WO | 2008/003116 A2 | 1/2008 |
| WO | 2008/119353 A1 | 10/2008 |
| WO | 2008/119567 A2 | 10/2008 |
| WO | 2008/145141 A1 | 12/2008 |
| WO | 2008/157379 A2 | 12/2008 |
| WO | 2009/040562 A1 | 4/2009 |
| WO | 2009058383 A2 | 5/2009 |
| WO | 2009/080254 A1 | 7/2009 |
| WO | 2009/089004 A1 | 7/2009 |
| WO | 2010/015792 A1 | 2/2010 |
| WO | 2010/026923 A1 | 3/2010 |
| WO | 2010059315 A1 | 5/2010 |
| WO | 2010/080538 A1 | 7/2010 |
| WO | 2010111625 A1 | 9/2010 |
| WO | 2010/129304 A2 | 11/2010 |
| WO | 2010134666 A1 | 11/2010 |
| WO | 2011014659 A2 | 2/2011 |
| WO | 2011/028952 A1 | 3/2011 |
| WO | 2011066501 A1 | 6/2011 |
| WO | 2011069104 A2 | 6/2011 |
| WO | 2011090762 A1 | 7/2011 |
| WO | 2011/117329 A1 | 9/2011 |
| WO | 2011/131746 A1 | 10/2011 |
| WO | 11143545 A1 | 11/2011 |
| WO | 2012023053 A2 | 2/2012 |
| WO | 2012025525 A1 | 3/2012 |
| WO | 2012025530 A1 | 3/2012 |
| WO | 2012/058768 A1 | 5/2012 |
| WO | 2012073985 A1 | 6/2012 |
| WO | 2012/143524 A2 | 10/2012 |
| WO | 2012162067 A2 | 11/2012 |
| WO | 2013/026833 A1 | 2/2013 |
| WO | 2013/060867 A2 | 5/2013 |
| WO | 2013123114 A2 | 8/2013 |
| WO | 2013157953 A1 | 10/2013 |
| WO | 2014/047231 A1 | 3/2014 |
| WO | 2014081202 A1 | 5/2014 |
| WO | 2014108483 A1 | 7/2014 |
| WO | 2014/131694 A1 | 9/2014 |
| WO | 2014/131711 A1 | 9/2014 |
| WO | 2015/001085 A1 | 1/2015 |
| WO | 2015006749 A2 | 1/2015 |
| WO | 2015/143079 A1 | 9/2015 |
| WO | 2016/081490 A1 | 5/2016 |
| WO | 2016/110576 A1 | 7/2016 |
| WO | 2017/210485 A1 | 12/2017 |
| WO | 2019/155008 A1 | 8/2019 |
| WO | 2021028587 A1 | 2/2021 |

OTHER PUBLICATIONS

Labrijn, AF et al., "Efficient generation of stable bispecific IgG1 by controlled Fab-arm exchange," PNAS, vol. 110(13):5145-5150 (2013).

Lee, D et al., "ASTCT Consensus Grading for Cytokine Release Syndrome and Neurologic Toxicity Associated with Immune Effector Cells," Biol Blood Marrow Transplant, vol. 25(4): 625-638 (2019).

Leonard, J. P et al., "AUGMENT: A Phase III Study of Lenalidomide Plus Rituximab Versus Placebo Plus Rituximab in Relapsed or Refractory Indolent Lymphoma," J Clin Oncol., vol. 37(14):1188-99 (2019).

Locke, F et al., "Long-term safety and activity of axicabtagene ciloleucel in refractory large B-cell lymphoma (ZUMA-1): a single-arm, multicentre, phase 1-2 trial," Lancet Oncol., vol. 20(1):31-42 (2019).

Lum and Thakur, "Targeting T cells with bispecific antibodies for cancer therapy," BioDrugs, vol. 25(6): 365-379 (2011).

Mau-Soerensen, M. et al. "A phase I trial of intravenous catumaxomab: a bispecific monoclonal antibody targeting EpCAM and the T cell coreceptor CD32015," Cancer Chemother. Pharmacol., vol. 75(5): 1065-1073 (2015).

Morschhauser F. et al. "Rituximab plus Lenalidomide in Advanced Untreated Follicular Lymphoma" New England Journal of Medicine, vol. 379(10): 934-947 (2018).

Muller, D, et al., "Bispecific antibodies for cancer immunotherapy: Current perspectives," BioDrugs, vol. 24(2): 89-98 (2010).

Niemann, C et al., "Venetoclax and Ibrutinib for Patients with Relapsed/Refractory Chronic Lymphocytic Leukemia (R/R CLL)-15-Month Safety, Response and MRD Evaluation: Third Interim Analysis from the Phase II Vision HO141 Trial," Blood, vol. 134(1): Abstract 4292, 5 pages (2019).

Oganesyan V et al., "Structural characterization of a human Fc fragment engineered for lack of effector functions," Acta Cryst., (D64): 700-704 (2008).

Oken, M et al., "Toxicity and response criteria of the Eastern Cooperative Oncology Group," Am J Clin Oncol, vol. 5(6): 649-655 (1982).

Olejniczak, S et al., "A quantitative exploration of surface antigen expression in common B-cell malignancies using flow cytometry," Immunol Invest, vol. 35(1): 93-114 (2006).

Overdijk, M et al., "Crosstalk between human IgG isotypes and murine effector cells," J. Immunol., vol. 189(7): 3430-3438 (2012).

Paraplatin®, retrieved on Feb. 9, 2022 www.accessdata.fda.gov/drugsatfda_docs/label/2010/020452s005lbl.pdf, 21 pages.

Parren, P. et al., "Induction of T-cell proliferation by recombinant mouse and chimeric mouse/human anti-CD3 monoclonal antibodies," Res Immunol., vol. 142(9): 749-763 (1991).

Patrizia, M. et al. "Bendamustine plus Rituximab Versus R-CHOP as First-Line Treatment for Patients with Follicular Lymphoma Grade 3A: Evidence from a Multicenter, Retrospective Study," The Oncologist, vol. 23(4):454-460 (2018).

Pedersen, I. et al., "The chimeric anti-CD20 antibody rituximab induces apoptosis in B-cell chronic lymphocytic leukemia cells through a p38 mitogen activated protein-kinase-dependent mechanism," Blood, vol. 99(4): 1314-1319 (2002).

(56) References Cited

OTHER PUBLICATIONS

Perks, B. et al., "Bispecific antibodies direct the immune system against blood; cancers," The Pharmaceutical Journal, URI: 20068566: 2 pages (2015).
Prescribing Information for Cyclophosphamide, Retrieved on Feb. 9, 2022, www.accessdata.fda.gov/drugsatfda_docs/label/2013/012141s090,012142s112lbl.pdf, 18 pages.
Prescribing Information for Eloxatin Retrieved on Feb. 9, 2022, www.accessdata.fda.gov/drugsatfda_docs/label/2020/021759s023lbl.pdf, 42 pages.
Prescribing Information for Gemzar, Retrieved on Feb. 9, 2022, www.accessdata.fda.gov/drugsatfda_docs/label/2014/020509s077lbl.pdf 18 pages.
Prescribing Information For Infugem, Retrieved on Feb. 9, 2022, www.accessdata.fda.gov/drugsatfda_docs/label/2018/208313Orig1s000lbl.pdf, 30 pages.
Prescribing Information for Rituxan®, Retrieved on Feb. 9, 2022, www.accessdata.fda.gov/drugsatfda_docs/label/2013/103705s5414lbl.pdf, 41 pages.
Prescribing Information for Treanda, 11 pages, (2008) retrieved on Feb. 9, 2022 https://www.accessdata.fda.gov/drugsatfda_docs/label/2008/022303lbl.pdf.
Prescribing Infromation for Bendeka Retrieved on Feb. 9, 2022, www.accessdata.fda.gov/drugsatfda_docs/label/2015/208194s000lbl.pdf. 23 pages.
Prescribing Infromation for Revlimid, Retrieved on Feb. 9, 2022, www.accessdata.fda.gov/drugsatfda_docs/label/2013/021880s034lbl.pdf, 33 pages.
Prevodnik, V. et al., "The predictive significance of CD20 expression in; B-cell lymphomas," Diagn Pathol., vol. 6(33): 6 pages (2011).
Project et al., "A predictive model for aggressive non-Hodgkin's lymphoma," N Engl J Med., vol. 329(14):987-994 (1993).
Qiu-Dan, S. et al. "Gemcitabine oxaliplatin plus rituximab (R-GemOx) as first-line treatment in elderly patients with diffuse large B-cell lymphoma: a single-arm, open-label, phase 2 trial," Lancet Haematology, vol. 5(6): 261-269 (2018).
Relander, T. et al., "Prognostic factors in follicular lymphoma," J Clin Oncol, vol. 28(17): 2902-2913 (2010).
Rigacci, L. et al., "Oxaliplatin-based chemotherapy (dexamethasone, high-dose cytarabine, and oxaliplatin) ± rituximab is an effective salvage regimen in patients with relapsed or refractory lymphoma," Cancer, vol. 116(19): 4573-4579 (2010).
Rossi, D et al., "Integrated mutational and cytogenetic analysis identifies new prognostic subgroups in chronic lymphocytic leukemia," Blood, vol. 121(8):1403-1412 (2013).
Rudikoff, S. et al., "Single amino acid substitution altering antigen-binding specificity," PNAS, vol. 79(6):1979-83 (1982).
Rummel, M. et al.,"Bendamustine plus rituximab versus CHOP plus rituximab as first-line treatment for patients with Indolent and mantle-cell lymphomas: an open-label, multicentre, randomised, phase 3 non-inferiority trial," Lancet, vol. 381 (9873):1203-1210 (2013).
Safety and Efficacy Trial of Epcoritamab Combinations in Subjects With B-cell Non-Hodgkin Lymphoma, https://clinicaltrials.gov/ct2/show/NCT04663347 ClinicalTrials.gov Identifier: NCT04663347, Nov. 3, 2021, 13 pages.
Salles, G. et al., "Efficacy and safety of idelalisib in patients with relapsed, rituximab- and alkylating agent-refractory follicular lymphoma: a subgroup analysis of a phase 2 study," Haematologica, vol. 102(4):e159 (2017).
Schuster, S et al., "Tisagenlecleucel in Adult Relapsed or Refractory Diffuse Large B-Cell Lymphoma," N Engl J Med, vol. 380(1): 45-56 (2019).
Sehn, L. et al., "The revised International Prognostic Index (R-IPI) is a better predictor of outcome than the standard IPI for patients with diffuse large B-cell lymphoma treated with R-CHOP," Blood, vol. 109(5):1857-1861 (2007).
Seymour, JF et al., "Venetoclax-Rituximab in Relapsed or Refractory Chronic Lymphocytic Leukemia," N Engl J Med, vol. 378(12): 1107-1120 (2018).
Shields, R et al., "High resolution mapping of the binding site on human IgG1 for Fc gamma RI, Fc gamma RII, Fc gamma RIII, and FcRn and design of IgG1 variants with improved binding to the Fc gamma R," Journ of Biol Chem., vol. 276(9): 6591-604 (2001).
Siegel, R et al., "Cancer statistics, 2019," 2019, CA Cancer J Clin, vol. 69(1):7-34 (2019).
Smith, E. et al."A novel, native-format bispecific antibody triggering T-cell killing of B-cells is robustly active in mouse tumor models and cynomolgus monkeys," Nat. Sci. Rep., vol. 5:17943: 12 pages (2015).
Staerz, U. et al., "Hybrid antibodies can target sites for attack by T cells," 1985, Nature, vol. 314(6012):628-31(1985).
Stanglmaier, M et al., "Bi20 (fBTA05), a novel trifunctional bispecific antibody (anti-CD20 x anti-CD3), mediates efficient killing of B-cell lymphoma cells even with very low CD20 expression levels," Int. J. Cancer, vol. 123 (5):1181-1189 (2008).
Sun, L et al., "Anti-CD20/CD3 T cell-dependent bispecific antibody; for the treatment of B cell malignancies," Science Transl Medicine, vol. 7(287): 1-11 (2015).
Tedder, TF et al., "The B cell surface molecule B1 is functionally linked with B cell activation and differentiation," J. Immunol., vol. 135(2): 973-979 (1985).
Tixier, F et al.,"Comparative toxicities of 3 platinum-containing chemotherapy regimens in relapsed/refractory lymphoma patients," Hematol Oncol., vol. 35(4):584-590 (2016).
Uhm, J., "Recent advances in chronic lymphocytic leukemia therapy," Blood Res Seoul, vol. 55(S1):S72-S82(2020).
Vajdos, F. et al., "Comprehensive functional maps of the antigen-binding site of an anti-ErbB2 antibody obtained with shotgun scanning mutagenesis," J Mol Biol., vol. 320(2): 415-28 (2002).
Valentine, M et al., "Phosphorylation of the CD20 phosphoprotein in resting B lymphocytes. Regulation by protein kinase C," J. Biol. Chem., vol. 264(19): 11282-11287 (1989).
Van der Horst, H. et al., "Duobody-CD3xCD20 Induces Potent Anti-Tumor Activity in Malignant Lymph Node B Cells from Patients with DLBCL, FL and MCL Ex Vivo, Irrespective of Prior Treatment with CD20 Monoclonal Antibodies," Blood, American Soc. of Hem., vol. 134(1): Abstract 4066: 4 pages (2019).
Van Der Neut Kolfschoten, M. et al., "Anti-Inflammatory Activity of Human IgG4 Antibodies by Dynamic Fab Arm Exchange," Science, vol. 317(5844): 1554-1557 (2007).
Varadarajan I, et al., "Management of Cytokine Release Syndrome," Chimeric Antigen receptor T-cell therapies for Cancer, Chapter 5 :45-64 (2020).
VinCRIStine Sulfate Rx only Injection, USP, Retrieved on Feb. 9, 2022, www.accessdata.fda.gov/drugsatfda_docs/label/2014/071484s042lbl.pdf, 9 pages.
Wagner-Johnston, N. et al., "Outcomes of transformed follicular lymphoma in the modern era: a report from the National LymphoCare Study (NLCS)," Blood, vol. 126(7): 851-857 (2015).
Wierda, W et al., "Multivariable model for time to first treatment in patients with chronic lymphocytic leukemia," Journ Clin Oncol., vol. 29(31): 4088-4095 (2011).
Wolchok, J et al., "Guidelines for the evaluation of immune therapy activity in solid tumors: immune-related response criteria," Clin Cancer Res, vol. 15(23): 7412-7420 (2009).
Wu, C. et al., "Simultaneous targeting of multiple disease mediators by a dual-variable-domain immunoglobulin," Nat Biotechnol., vol. 25(11):1290-1297 (2007).
Xiong, D. et al., "Efficient inhibition of human B-cell lymphoma xenografts with an anti-CD20 x anti-CD3 bispecific diabody," Cancer Letters., vol. 177(1):29-39 (2002).
Zenz, T. et al., "From pathogenesis to treatment of chronic lymphocytic leukaemia," Nat Rev Cancer, vol. 10(1):37-50 (2010).
Burger, J. et al., "Randomized trial of ibrutinib vs ibrutinib plus rituximab in patients with chronic lymphocytic leukemia," Blood, vol. 133(10):1011-1019 (2019).

(56) References Cited

OTHER PUBLICATIONS

Gramer, M. et al., "Production of stable bispecific IgG1 by controlled Fab-arm exchange Scalability from bench to large-scale manufacturing by application of standard approaches," mAbs, vol. 5(6): 962-973 (2013).
Labrijn, A. et al., "Controlled Fab-arm exchange for the generation of stable bispecific IgG1," Nature Protocols, vol. 9 (10): 2450-63 (2014).
Sarkozy, C. et al., "Cause of Death in Follicular Lymphoma in the First Decade of the Rituximab Era: A Pooled Analysis of French and US Cohorts," J Clin Oncol., vol. 37:144-152. (2018).
Tam, C. et al., "Ibrutinib (Ibr) Plus Venetoclax (Ven) for First-Line Treatment of Chronic Lymphocytic Leukemia (CLL)/Small Lymphocytic Lymphoma (SLL): Results from the MRD Cohort of the Phase 2 CAPTIVATE Study," Blood, vol. 134 (Supplement_1): Abstract No. 35 (2019) Abstract Only, 8 pages.
U.S. Appl. No. 14/934,956, filed Nov. 6, 2015, Janine Schuurman, U.S. Pat. No. 10,906,991.
U.S. Appl. No. 12/593,759, filed Jan. 6, 2010, Janine Schuurman, U.S. Pat. No. 9,212,230.
U.S. Appl. No. 16/777,053, filed Jan. 30, 2020, Aran Frank Labrijn, US 2020-0262932.
U.S. Appl. No. 15/414,122, filed Jan. 24, 2017, Aran Frank Labrijn, U.S. Pat. No. 10,597,464.
U.S. Appl. No. 13/642,253, filed Oct. 24, 2012, Aran Frank Labrijn, U.S. Pat. No. 9,150,663.
U.S. Appl. No. 16/426,647, filed May 30, 2019, Michael Gramer, US 2020-0048304.
U.S. Appl. No. 14/353,962, filed Apr. 24, 2014, Michael Gramer, U.S. Pat. No. 10,344,050.
U.S. Appl. No. 16/783,720, filed Feb. 6, 2020, Aran Frank Labrijn, US 2020-0332022.
U.S. Appl. No. 14/760,157, filed Jul. 9, 2015 Aran Frank Labrijn, U.S. Pat. No. 10,590,206.
U.S. Appl. No. 16/582,428, filed Sep. 25, 2019, Edward Van Den Brink, US 2020-0123255.
U.S. Appl. No. 14/902,757, filed Jan. 4, 2016, Edward Van Den Brink, U.S. Pat. No. 10,465,006.
U.S. Appl. No. 16/544,376, filed Aug. 19, 2019, Edward Norbert Van Den Brink, US 2020-0199229.
U.S. Appl. No. 15/110,414, filed Jul. 8, 2016, Edward Norbert Van Den Brink, U.S. Pat. No. 10,407,501.
U.S. Appl. No. 16/702,996, filed Dec. 4, 2019, Patrick Engelberts, US 2020-0199231.
U.S. Appl. No. 15/541,594, filed Jul. 5, 2017, Patrick Engelberts, U.S. Pat. No. 10,544,220.
U.S. Appl. No. 17/558,430, filed Dec. 21, 2021, Brian Elliott.
U.S. Appl. No. 17/559,938, filed Dec. 22, 2021, Brian Elliott.
U.S. Appl. No. 17/558,404, filed Dec. 21, 2021, Brian Elliott.
U.S. Appl. No. 17/560,006, filed Dec. 22, 2021, Brian Elliott.
U.S. Appl. No. 17/559,965, filed Dec. 22, 2021, Brian Elliott.
Sarkozy, C. et al., "New drugs for the management of relapsed or refractory diffuse large B-cell lymphoma," Ann Lymphoma, vol. 3(10) 19 pages (2019).
Chen, X. et al., "A Modeling Framework to Characterize Cytokine Release upon T-Cell-Engaging Bispecific Antibody Treatment: Methodology and Opportunities," Clinical Translational Science, vol. 12(6): 600-608 (2019).
Chiu, H. et al., "Combination lenalidomide-rituximab immunotherapy activates anti-tumour immunity and induces tumour cell death by complementary mechanisms of action in follicular lymphoma," British Journal of Haematology, vol. 185:240-253 (2019).
Friend, P.J. et al., "Phase I study of an engineered aglycosylated humanized CD3 antibody in renal transplant rejection," Transplantation, vol. 68 (11): 13 pages (1999).
Lignon, J. et al., "Rituximab, Dexamethasone, Cytarabine, and Oxaliplatin (R-DHAX) Is an Effective and Safe Salvage Regimen in Relapsed/Refractory B-Cell Non-Hodgkin Lymphoma," Clinical Lymphoma, Myeloma & Leukemia, vol. 10 (4): 262-269 (2010).
MedlinePlus. Lenalidomide, Mar. 22, 2022, pp. 1-7 (2022).

Rummel, M. et al., Lymphoma: Chemotherapy, Excluding Pre-Clinical Models Non-Hodgkin Lymphoma Therapy, Blood, vol. 114 (22) (Abstract No. 405):3 pages (2009).
Sarkozy and Sehn, "Management of relapsed/refractory DLBCL," Best Practice & Research in Clinical Hematology, vol. 31: 209-216 (2018).
Seiler and Hiddemann, "Advances in the management of follicular lymphoma," Current Opinion in Oncology, vol. 24(6): 742-747 (2012).
Tessoulin, B. et al., "Carboplatin instead of cisplatin in combination with dexamethasone, high-dose cytarabine with or without rituximab (DHAC+/−R) is an effective treatment with low toxicity in Hodgkin's and non-Hodgkin's lymphomas," Annals of Hematology, vol. 96: 943-950 (2017).
Adriamycin (DOXOrubicin HCI) for Injection, retrieved on Feb. 9, 2022 www.accessdata.fda.gov/drugsatfda_docs/label/2012/062921s022lbl.pdf, 2 pages.
Almasri, N et al., "Reduced expression of CD20 antigen as a characteristic marker for chronic lymphocytic leukemia," Am J Hematol, vol. 40(4):259-63 (1992).
Amgen, Blinatumomab prescribing information and medication guide, Dec. 2014, 24 pages.
Andersson, K. et al., "Expression of human B cell-associated antigens on leukemias and lymphomas: a model of human B cell differentiation," Blood, vol. 63(69):1424-1433 (1984).
Bacac, M. et al., "CD20-TCB with obinutuzumab pretreatment as next generation treatment of hematological malignancies," Clin Cancer Res., vol. 24(19):4785-4797 (2018).
Barrington, S. et al., "Role of imaging in the staging and response assessment of lymphoma: consensus of the International Conference on Malignant Lymphomas Imaging Working Group," J Clin Oncol., vol. 32(27):3048-58 (2014).
Bedouelle, H. et al., "Diversity and junction residues as hotspots of binding energy in an antibody neutralizing the dengue virus," FEBS J., vol. 273(1):34-46 (2006).
Berek, J. et al., "Catumaxomab for the treatment of malignant ascites in patients with chemotherapy-refractory ovarian cancer: a phase II study," Int. J. Gynecol. Cancer, vol. 24(9): 1583-1589 (2014).
Brown, M. et al., "Tolerance of single, but not multiple, amino acid replacements in antibody VH CDR 2: a means of minimizing B cell wastage from somatic hypermutation?," J Immunol., vol. 156(9):3285-91 (1996).
Canfield, S.M. et al., "The binding affinity of human IgG for its high affinity Fc receptor is determined by multiple amino acids in the CH2 domain and is modulated by the hinge region," J. Exp.Med., vol. 173(6):1483-91 (1991).
Casulo, C. et al., "Autologous Transplantation in Follicular Lymphoma with Early Therapy Failure: A National LymphoCare Study and Center for International Blood and Marrow Transplant Research Analysis," Biol Bood Marrow Transplant, vol. 24(6):1163-71 (2018).
Cheson, B. et al., "Recommendations for initial evaluation, staging, and response assessment of Hodgkin and non-Hodgkin lymphoma: the Lugano classification," J Clin Oncol., vol. 32(27):3059-68 (2014).
Cheson, B. et al., "Refinement of the Lugano Classification lymphoma response criteria in the era of Immunomodulatory therapy," Blood, vol. 128(21):2489-96 (2016).
Chiorazzi, N. et al., "Chronic lymphocytic leukemia," N Engl J Med., vol. 352(8):804-15. (2005).
Chu, S. et al, "3111 Immunotherapy with Long-Lived Anti-CD20 x Anti-CD3 Bispecific Antibodies Stimulates Potent T Cell-Mediated Killing of Human B Cell Lines and of Circulating and Lymphoid B Cells in Monkeys: A Potential Therapy for B Cell Lymphomas and Leukemias," 56th ASH Annutal Meeting and Exposition, 2 pages (2014).
CLL-IPI, "An international prognostic index for patients with chronic lymphocytic leukaemia (CLL-IPI): a meta-analysis of individual patient data," Lancet Oncol., vol. 17(6):779-790 (2016).
Coiffier, B. et al., "Guidelines for the management of pediatric and adult tumor lysis syndrome: an evidence-based review," J Clin Oncol., vol. 26(16):2767-2708 (2008).

(56) References Cited

OTHER PUBLICATIONS

Colman, P., "Effects of amino acid sequence changes on antibody-antigen interactions," Res Immunol., vol. 145(1):33-6 (1994).
Cytarabine—cytarabine injection, solution Hospira, Inc., lebeling, retrieved on Feb. 9, 2022, labeling.pfizer.com/ShowLabeling aspx?id=4397.
Dall'Acqua WF et al., "Modulation of the effector functions of a human IgG1 through engineering of its hinge region," J Immunol., vol. 177(2):1129-1138 (2006).
D'Arena, G et al., "Quantitative flow cytometry for the differential diagnosis of leukemic B-cell chronic lymphoproliferative disorders," Am J Hematol, vol. 64(4): 275-281 (2000).
Dexamethasone Sodium Phosphate Label, Retrieved on Feb. 9, 2022, www.accessdata.fda.gov/drugsatfda_docs/label/2014/40572s002lbledt.pdf, 2 pages.
Doxorubicin Hydrochloride for Injection, usp, retrieved on Feb. 9, 2022 www.accessdata.fda.gov/drugsatfda_docs/label/2010/050467s070lbl.pdf, 22 pages.
Duncan, A.R., "The binding site for C1q on IgG," Nature, vol. 332(6166):738-40 (1988).
Einfeld, DA, et al., "Molecular cloning of the human B cell CD20 receptor predicts a hydrophobic protein with multiple transmembrane domains," EMBO Journ, vol. 7(3): 711-717 (1988).
Engelberts, P. J et al., "DuoBody-CD3xCD20 induces potent T-cell-mediated killing of malignant B cells in preclinical models and provides opportunities for subcutaneous dosing," EBioMedicine, vol. 52(102625) 13 pages (2020).
Fisher, K. et al., "Venetoclax and Obinutuzumab in Patients with CLL and Coexisting Conditions," N Engl J Med., vol. 380 (23):2225-2236 (2019).
Fitzmaurice, C et al., "Global, Regional, and National Cancer Incidence, Mortality, Years of Life Lost, Years Lived With Disability, and Disability-Adjusted Life-Years for 29 Cancer Groups, 1990 to 2016: A Systematic Analysis for the Global Burden of Disease Study," JAMA Oncol., vol. 4(11):1553-68 (2018).
Gall, J. M et al., "T cells armed with anti-CD3 x anti-CD20 bispecific antibody enhance killing of CD20+ malignant B cells and bypass complement-mediated rituximab resistance in vitro," Exp Hematol., vol. 33(4):452-9 (2005).
Garber, K., "Bispecific antibodies rise again," Nat. Rev. Drug Discov., vol. 13(11): 799-801 (2014).
GEN3013 Trial in Patients With Relapsed, Progressive or Refractory B-Cell Lymphoma, https://clinicaltrials.gov/ct2/show/study/NCT03625037, GEN3013 Trial in Patients With Relapsed . . . —Full Text View—ClinicalTrials.pdf, 8 pages.
Ginaldi, L. et al., "Levels of expression of CD19 and CD20 in chronic B cell leukaemias," J Clin Pathol., vol. 51(5): 364-369 (1988).
Gisselbrecht, C et al., "Salvage regimens with autologous transplantation for relapsed large B-cell lymphoma in the rituximab era," J Clin Oncol., vol. 28 (27): 4184-90 (2010).
Goede, V et al., "Obinutuzumab plus chlorambucil in patients with CLL and coexisting conditions," N Engl J Med., vol. 370(12):1101-10 (2014).
Gokarn Y. R. et al, "Self-buffering antibody formulations," Journal of Pharmaceutical Sciences, American Chemical Society and American Pharmaceutical Association US, vol. 97(8): 3051-66 (2008).
Hallek, M. et al., "Chronic lymphocytic leukaemia," The Lancet, vol. 391(10129):1524-1537 (2018).
Hallek, M. et al.,"Addition of rituximab to fludarabine and cyclophosphamide in patients with chronic lymphocytic leukaemia: a randomised, open-label, phase 3 trial," 2010, Lancet, vol. 376(9747): 1164-1174 (2010).
Herold, K et al., "A single course of anti-CD3 monoclonal antibody hOKT3gamma1(Ala-Ala) results in improvement in C-peptide responses and clinical parameters for at least 2 years after onset of type 1 diabetes," Diabetes, vol. 54(6): 1763-1769 (2005).
Hezareh, M et al., "Effector function activities of a panel of mutants of a broadly neutralizing antibody against human immunodeficiency virus type 1," J Virol., vol. 75(24): 12161-12168 (2001).
Hiddemann, W. et al., "Frontline therapy with rituximab added to the combination of cyclophosphamide, doxorubicin, vincristine, and prednisone (CHOP) significantly improves the outcome for patients with advanced-stage follicular lymphoma compared with therapy with CHOP alone: results of a prospective randomized study of the German Low-Grade Lymphoma Study Group," Blood, vol. 106(12):3725-3732 (2005).
Howard, S. et al., "The tumor lysis syndrome," N Engl J Med, vol. 364(19): 1844-1854 (2011).
Ito K et al.,"Influence of R-CHOP Therapy on Immune System Restoration in Patients with B-Cell Lymphoma," Oncology, vol. 91(6):302-310 (2016).
Jabbour, E. et al., "Phase II Study Of The Hyper-CVAD Regimen In Combination With Ofatumumab As Frontline Therapy For Adults With CD-20 Positive Acute Lymphoblastic Leukemia (ALL)," Blood, vol. 122(21):2664: 5 pages (2003).
Jardin F., "Improving R-CHOP in diffuse large B-cell lymphoma is still a challenge" Lancet Oncology, vol. 20 (5):605-606 (2019).
Jurinovic, V et al., "Autologous Stem Cell Transplantation for Patients with Early Progression of Follicular Lymphoma: A Follow-Up Study of 2 Randomized Trials from the German Low Grade Lymphoma Study Group," Biol Blood Marrow Transplant, vol. 24(6): 1172-9 (2018).
Kang J, et al, "Rapid formulation Development for Monoclonal Antibodies" Bioprocess International, 6 page, Apr. 12, 2016.
Khan, Y et al., "Acalabrutinib and its use in treatment of chronic lymphocytic leukemia," Future Oncol., vol. 15(6):579-589 (2019).
Kontermann, R et al., "Bispecific antibodies," Drug Discov Today, vol. 20(7):838-847 (2015).
Konternamm R "Dual targeting strategies with bispecific antibodies" mAbs vol. 4(2), p. 182-197 (2012).
Kurokawa, T. et al., "Immune reconstitution of B-cell lymphoma patients receiving CHOP-based chemotherapy containing rituximab," Hematol Oncol., vol. 29(1): 5-9 (2011).
Mounier, N. et al., "Rituximab plus CHOP (R-CHOP) overcomes bcl-2—associated resistance to chemotherapy in elderly patients with diffuse large B-cell lymphoma (DLBCL)," Blood, vol. 101: 4279-4284 (2003).
Mounier, N. et al., "Rituximab plus gemcitabine and oxaliplatin in patients with refractory/relapsed diffuse large B-cell lymphoma who are not candidates for high-dose therapy. A phase II Lymphoma Study Association trial," Haematologica, vol. 98(11): 1726-1731 (2013).
Maeshima, A. et al., "Follow-up Data of 10 Patients With B-cell Non-Hodgkin Lymphoma With a CD20-negative Phenotypic Change After Rituximab-containing Therapy," Am J Surg Pathol., vol. 37:563-570 (2013).
Mansfield, K. et al., "Marmoset Models Commonly Used in Biomedical Research," Comparative Med., vol. 53(4):383-92 (2003).
Marvin JS et al., "Recombinant approaches to IgG-like bispecific antibodies," Acta Pharmacol Sin., vol. 26(6):649-58 (2005).
McCafferty, J. et al., "Phage antibodies: filamentous phage displaying antibody variable domains," Nature, vol. 348:552-554 (1990).
Mendez MJ, et al., "Functional transplant of megabase human immunoglobulin loci recapitulates human antibody response in mice," Nat Genet., vol. 15(2):146-56 (1997).
Mølhøj M, et al., "CD19-/CD3-bispecific antibody of the BiTE class is far superior to tandem diabody with respect to redirected tumor cell lysis," Mol Immunol., vol. 44(8):1935-43 (2007).
Mondello, P. et al. "Bendamustine plus Rituximab Versus R-CHOP as First-Line Treatment for Patients with Follicular Lymphoma Grade 3A: Evidence from a Multicenter, Retrospective Study," The Oncologist, vol. 23(4):454-460 (2018).
Myers EW et al., "Optimal alignments in linear space," Comput Appl Biosci., vol. 4(1):11-17 (1988).
Needleman and Wunsch, J., "A general method applicable to the search for similarities in the amino acid sequence of two proteins," Mol. Biol., vol. 48(3): 444-453 (1970).
Neelapu SS, et al., "Chimeric antigen receptor T-cell therapy—assessment and management of toxicities," Nat Rev Clin Oncol., vol. 15(1):47-62 (2018).

(56) References Cited

OTHER PUBLICATIONS

Paino, T. et al., "CD20 positive cells are undetectable in the majority of multiple myeloma cell lines and are not associated with a cancer stem cell phenotype," Diagnostic Pathology, vol. 6:33 (2011).
Parren PW, et al., "On the interaction of IgG subclasses with the low affinity Fc gamma Rlla (CD32) on human monocytes, neutrophils, and platelets, Analysis of a functional polymorphism to human IgG2," J Clin Invest., vol. 90(4):1537-46 (1992).
Patel et al., "Preliminary Safety and Anti-Tumor activity of XmAbl 3676, an Anti-CD20 x Anti-CD3 Bispecific Antibody, In Patients with Relapsed/Refractory Non-Hodgkin's Lymphoma and Chronic Lymphocytic Leukemia," Blood, Abstract only, 1 page (2019).
Paul, W. Fundamental Immunology Ch. 7 (2nd ed. Raven Press, N.Y. (1989).
Pearce LA, et al., "Linear gene fusions of antibody fragments with streptavidin can be linked to biotin labelled secondary molecules to form bispecific reagents," Biochem Mol Biol Int., vol. 42(6):1179-1188 (1997).
Pluckthun in 'The Pharmacology of Monoclonal Antibodies', vol. 113, Rosenburg and Moore eds. Springer-Verlag, New York, pp. 269 315 (1994).
Poncelet P, et al., "Cytofluorometric quantification of cell-surface antigens by indirect immunofluorescence using monoclonal antibodies," J Immunol Methods, vol. 85(1):65-74 (1985).
Prescribing Information for IMBRUVICA®, Retrieved on May 4, 2023, https://www.accessdata.fda.gov/drugsatfda_docs/label/2016/205552s007lbl.pdf, 32 pages.
Prescribing Information for POLIVY®, Retrieved on May 4, 2023, https://www.accessdata.fda.gov/drugsatfda_docs/label/2019/761121s000lbl.pdf, 19 pages.
Rasouli M. "Basic concepts and practical equations on osmolality: Biochemical approach," Clin Biochem., vol. 49(12):936-941 (2016).
Remington: The Science and Practice of Pharmacy, 19th Edition, Gennaro, Ed., Mack Publishing Co., Easton, PA, 1995.
Revets H, et al., "Nanobodies as novel agents for cancer therapy," Expert Opin Biol Ther., vol. 5(1):111-24 (2005).
Sambrook et al., 1989, Molecular Cloning: A laboratory Manual, New York: Cold Spring Harbor Laboratory Press, Ch. 15.
Schakowski F, et al., "A novel minimal-size vector (MIDGE) improves transgene expression in colon carcinoma cells and avoids transfection of undesired DNA," Mol Ther., vol. 3(5 Pt 1):793-800 (2001).
Schoonjans R, et al., "Fab chains as an efficient heterodimerization scaffold for the production of recombinant bispecific and trispecific antibody derivatives," J Immunol., vol. 165(12):7050-7 (2000).
Shen, Qiu-Dan, et al. "Gemcitabine oxaliplatin plus rituximab (R-GemOx) as first-line treatment in elderly patients with diffuse large B-cell lymphoma: a single-arm, open-label, phase 2 trial," Lancet Haematology, vol. 5(6): 261-269 (2018).
Shipp et al., "A predictive model for aggressive non-Hodgkin's lymphoma," N Engl J Med., vol. 329(14):987-994 (1993).
Sykes KF, et al., "Linear expression elements: a rapid, in vivo, method to screen for gene functions," Nat Biotechnol., vol. 17(4):355-9 (1999).
The EMA Guideline on the Evaluation of Anti-cancer Medicinal Products in Man (EMA, 2012).
The EMA Guideline on the Evaluation of Anti-cancer Medicinal Products in Man (EMA, 2017).
Thieblemont, C. et al., "Epcoritamab, a Novel, Subcutaneous CD3xCD20 Bispecific T-Cell-Engaging Antibody, in Relapsed or Refractory Large B-Cell Lymphoma: Dose Expansion in a Phase I/II Trial," Clinical Oncology, vol. 41 (12):2238-2247 (2023).
Van Heeke G, et al. "Expression of human asparagine synthetase in *Escherichia coli*," J Biol Chem., vol. 264(10):5503-9 (1989).
Wang, W. et al., "Antibody Structure, Instability, and Formulation," J Pharm Sci., vol. 96(1)1-26 (2007).
Ward, E. et al. "Binding activities of a repertoire of single immunoglobulin variable domains secreted from *Escherichia coli*," Nature, vol. 341:544-546 (1989).

Webster DM, et al., "Engineering antibody affinity and specificity," Int J Cancer Suppl., vol. 3:13-6 (1988).
Wigler M., et al. "Biochemical transfer of single-copy eucaryotic genes using total cellular DNA as donor," Cell, vol. 14(3):725-31 (1978).
Withoff, S. et al., Characterization of BIS20x3, a bi-specific antibody activating and retargeting T-cells to CD20-positve B-cells,: British Journal of Cancer, vol. 84(8):1115-1121 (2001).
Wranik BJ et al., "LUZ-Y, a novel platform for the mammalian cell production of full-length IgG-bispecific antibodies," J Biol Chem., vol. 287(52):43331-9 (2012).
Wu et al., Generation and Characterization of a Dual Variable Domain Immunoglobulin (DVD-Ig™) Molecule, In: Antibody Engineering, Springer Berlin Heidelberg (2010).
Xu, D. et al., "In vitro characterization of five humanized OKT3 effector function variant antibodies," Cell Immunol., vol. 200 (1):16-26 (2000).
Zalevsky J, et al., "Enhanced antibody half-life improves in vivo activity," Nat Biotechnol., vol. 28(2):157-9 (2010).
Zheng, L., et al., "Expression Improvement and Mechanistic Study of the Retro-Diels-Alderase Catalytic Antibody 10F11 by Site-directed Mutagenesis," Journal of Molecular Biology, vol. 341(3), 807-14 (2004).
Zhu X. et al., "COMBODY: one-domain antibody multimer with improved avidity," Immunol Cell Biol., vol. 88(6):667-75 (2010).
Alvaro-Naranjo, T. et al., "CD20-negative DLBCL transformation after rituximab treatment in follicular lymphoma: a new case report and review of the literature," Ann Hematol., vol. 82:585-588 (2003).
Anonymous: "Definition of dose escalation study—NCI Dictionary of Cancer Terms—National Cancer Institute," pp. 1-1,(2021) XP55828675, Retrieved from the Internet:URL:https://www.cancer.gov/publications/dictionaries/cancer-terms/def/dose-escalation-study [retrieved on Jul. 29, 2021].
Anonymous: "loading dose SpringerLink",Jun. 27, 2021 (Jun. 27, 2021), p. 1 XP055828729, Retrieved from the Internet:URL:https://link.springer.com/chapter/10.I007/978-3-211-89836-9796 [retrieved on Jul. 29, 2021].
Ausubel, F. et al., ed. Current Protocols in Molecular Biology, Greene Publishing and Wiley InterScience New York (1987).
Bargou, R. et al., "Tumor Regression in Cancer Patients by Very Low Doses of a I Cell-Engaging Antibody," Science, vol. 321:974-977 (2008).
Bebbington, C.R. et al., "High-level expression of a recombinant antibody from myeloma cells using a glutamine synthetase gene as an amplifiable selectable marker," Biotechnology, vol. 10(2):169-75 (1992).
Bird, R.E. et al., "Single-chain antigen-binding proteins," Science, vol. 242(4877):423?426 (1988).
Blankenship JW, et al., "Abstract #5465: CD79BxDR SCORPIONTM molecule: a single chain, bispecific immunotherapeutic with potent in vitro activity against B cell lymphoma ," AACR 100th Annual Meeting, Cancer Res/, vol. 69 (9_Supplement):4 pages (2009).
Blinatumomab prescribing information and medication guide, Dec. 2014, pp. 1-20 and 1-4 (2014).
Bostrom, J. et al., "Variants of the antibody herceptin that interact with HER2 and VEGF at the antigen binding site," Science, vol. 323 (5921): 1610-1614 (2009).
Brochet X., "IMGT/V-Quest: the highly customized and integrated system for IG and TR standardized V-J and V-D-J sequence analysis," Nucl Acids Res., vol. 36:W503-508 (2008).
Brok, H. et al., "An Extensive Monoclonal Antibody Panel for the Phenotyping of Leukocyte Subsets in the Common Marmoset and the Cotton-Top Tamarin," Cytometry, vol. 45:294-303 (2001).
Bruhns, P. et al., "Specificity and affinity of human Fcgamma receptors and their polymorphic variants for human IgG subclasses," Blood, vol. 113(16): 3716-3725 (2009).
Buckner , C. et al., "Priming B cell-mediated anti-HIV envelope responses by vaccination allows for the long-tem control of infection in macaques exposed to a R5-tropic SHIN," Virology, vol. 320, 167-180 (2004).
Chavez, J. et al., "CAR T cell therapy for B-cell lymphomas," Best Pract Res Clin Haematol., vol. 31(2):135-146 (2018).

(56) References Cited

OTHER PUBLICATIONS

Chothia and Lesk J., "Canonical structures for the hypervariable regions of immunoglobulins," Mol. Biol., vol. 196(4):901-917 (1987).
Collett ED—Aulton ME (ED) 2, "Dosage Regimens", Jan. 1, 2001 (Jan. 1, 2001), Pharmaceutics. The Science of Dosage Form Design ED. 2, Churchill Livigstone, pp. 275-288, XP003030862.
Committee for Medicinal Products for Human Use (CHMP), "Guideline on the evaluation of anticancer medicinal products in man," European Medicines Agency, Science Medicines Health, EMA/CHMP/205/95 Rev.5, Sep. 22, 2017, 43 pages.
Coraro and Pearson, "Enhancing the efficiency of DNA-mediated gene transfer in mammalian cells," Somatic Cell Genetics, vol. 7(5):603-615 (1981).
Dall'Acqua, W. et al., "Properties of human IgG1s engineered for enhanced binding to the neonatal Fc receptor (FcRn)," J. Biol. Chem., vol. 281(33):23514-23524 (2006).
Deo YM, et al. "Bispecific molecules directed to the Fc receptor for IgA (Fc alpha RI, CD89) and tumor antigens efficiently promote cell-mediated cytotoxicity of tumor targets in whole blood," J Immunol., vol. 160(4):1677-86. PMID: 9469424 (1998).
Dick LW et al., "C-terminal lysine variants in fully human monoclonal antibodies: investigation of test methods and possible causes," Biotechnol Bioeng., vol. 100(6):1132-43 (2008).
Dimasi, N., et al., "The design and characterization of oligospecific antibodies for simultaneous targeting of multiple disease mediators," J Mol Biol., vol. 393(3): 672-92 (2009).
Doppalapudi VR, et al., "Chemically programmed antibodies: endothelin receptor targeting CovX-Bodies," Bioorg Med Chem Lett., vol. 17(2):501-6 (2007).
Edelman GM, et al.,"The covalent structure of an entire gammaG immunoglobulin molecule," Proc Natl Acad Sci., vol. 63(1):78-85 (1969).
Evans MJ, et al., "Rapid expression of an anti-human C5 chimeric Fab utilizing a vector that replicates in COS and 293 cells," J Immunol Methods, vol. 84(1):123-38(1995).
Falchi, L. et al, "Subcutaneous Epcoritamab with Rituximab + Lenalidomide in Patients with Relapsed or Refractory Follicular Lymphoma:Phase 1/2 Trial Update," Blood, vol. 140 (Supplement 1): 1464-1466 (2022).
Giavedoni, L.D. et al., "Phenotypic changes associated with advancing gestation in maternal and fetal baboon lymphocytes," Journal of Reproductive Immunology, vol. 64:121-132 (2004).
Grant, B. et al., "Expression and Secretion Vectors for Yeast," Methods in Enzymol., vol. 153: 516-544 (1987).
Hinton, P. et al., "An Engineered Human IgG1 Antibody with Longer Serum; Half-Life," J. Immunol., vol. 176:346-356 (2006).
Himila, I. et al.,A bispecific nanobody to provide full protection against lethal scorpion envenoming. FASEB J., vol. 24(9):3479-3489 (2010).
Holt, L. et al., "Domain antibodies: proteins for therapy," Trends Biotechnol., vol. 21(11):484-490 (2003).
Huston, J. et al., "rotein engineering of antibody binding sites: recovery of specific activity in an anti-digoxin single-chain Fv analogue produced in *Escherichia coli*," PNAS, vol. 85(16): 5879?5883 (1988).
Hutchings M. et al., Epcoritamab (GEN3013; DuoBody-CD3xCD20) to induce complete response in patients with relapsed/refractory B-cell non-Hodgkin lymphoma (B-NHL): Complete dose escalation data and efficacy results from a phase I/II trial., Journal of Clinical Oncology, 1 page (2020).
Idusogie EE, et al., "Mapping of the C1q binding site on rituxan, a chimeric antibody with a human IgG1 Fc," J Immunol., vol. 164: 4178-4184 (2000).

International Search Report and Written Opinion, PCT/EP2020/072927, dated Nov. 18, 2020, 10 pages.
International Search Report, PCT/EP2021/062231, dated Aug. 9, 2021, 6 pages.
Kabat et al., Sequences of Proteins of Immunological Interest, Fifth Edition. 1991 NIH Publication No. 91-3242.
Kohler and Milstein, "Continuous cultures of fused cells secreting antibody of predefined specificity," Nature, ol. 256(5517) : 495-497 (1975).
LaFleur DW, et al., "Monoclonal antibody therapeutics with up to five specificities: functional enhancement through fusion of target-specific peptides," MAbs vol. 5(2):208-18 (2013).
Lawrence, L.J. "Orientation of antigen binding sites in dimeric and trimeric single chain Fv antibody fragments," FEBS Lett., vol. 425(3):479-484 (1988).
Le Gall, F. et al., "Effect of linker sequences between the antibody variable domains on the formation, stability and biological activity of a bispecific tandem diabody," Protein Eng Des Sel., vol. 17(4):357-366 (2004).
Le Tourneau et al., "Dose escalation methods in phase I cancer clinical trials," Clinical Trials, J Natl Cancer Inst, vol. 101(10):708-720 (2009).
Leabman M.L. et al., "Effects of altered Fc?R binding on antibody pharmacokinetics in cynomolgus monkeys," Mabs, vol. 5(6):896-903 (2013).
Lefranc MP, et al., "IMGT, the international ImMunoGeneTics database.," Nucleic Acids Res., vol. 27(1):209-212 (1999).
Lewis SM, et al., "Generation of bispecific IgG antibodies by structure-based design of an orthogonal Fab interface," Nat Biotechnol., vol. 32(2):191-8 (2014).
Li T. et al., "Novel Semi-Mechanistic Model Leveraging Preclinical and Clinical Data to Inform the Recommended Phase 2 Dose (RP2D) Selection for Epcoritamab (DuoBody CD3xCD20)", Nov. 5, 2020 (Nov. 5, 2020), pp. 1-3, Retrieved from the Internet: URL:https://ashpublications.org/blood/article/136/Supplement%201/35/472423/Novel-Semi-Mechanistic-Model-Leveraging XP055828844 [retrieved on Jul. 29, 2021].
Lightle S, et al., "Mutations within a human IgG2 antibody form distinct and homogeneous disulfide isomers but do not affect Fc gamma receptor or C1q binding" Protein Sci., vol. 19(4):753-62 (2010).
Lindhofer H. et al., "Preferential species-restricted heavy/light chain pairing in rat/mouse quadromas. Implications for a single-step purification of bispecific antibodies.," J Immunol., vol. 155(1):219-25 (1995).
Lugtenburg P., et al., "First-in-Human, Phase 1/2 Trial to Assess the Safety and Clinical Activity of Subcutaneous GEN3013 (DuoBody-CD3xCD20) in B-Cell Non-Hodgkin Lymphomas," Blood, American Society of Hematology, US, vol. 134 (2019).
U.S. Appl. No. 17/314,946, filed May 7, 2021, Tahamtan Ahmadi, US 20210371538.
U.S. Appl. No. 17/923,317, filed Nov. 4, 2022, Tahamtan Ahmadi.
U.S. Appl. No. 17/939,736, filed Sep. 7, 2022, Michael Gramer.
U.S. Appl. No. 17/950,350, filed Sep. 22, 2022, Aran Frank Labrijn.
U.S. Appl. No. 18/109,708, filed Feb. 14, 2023, Edward Norbert Van Den Brink.
U.S. Appl. No. 16/967,365, filed Aug. 4, 2020, Jesper Valbjoern, US 20210032358.
U.S. Appl. No. 17/635,258, filed Feb. 14, 2022, Jesper Valbjoern, US 20220411505.
U.S. Appl. No. 18/160,386, filed Jan. 27, 2023, Christopher W. L. Chiu.
U.S. Appl. No. 18/160,391, filed Jan. 27, 2023, Christopher W. L. Chiu.

\* cited by examiner

BISPECIFIC ANTIBODIES AGAINST CD3 AND CD20 FOR TREATING CHRONIC LYMPHOCYTIC LEUKEMIA

CROSS-REFERENCE TO RELATED APPLICATIONS

This application is a continuation of U.S. application Ser. No. 17/471,861, filed on Sep. 10, 2021, which claims the benefit of U.S. Provisional Application Ser. No. 63/076,733, filed on Sep. 10, 2020. The entire contents of the above-referenced patent applications are incorporated herein by reference.

SEQUENCE LISTING

The instant application contains a Sequence Listing which has been submitted electronically in ASCII format and is hereby incorporated by reference in its entirety. Said ASCII copy, created on Dec. 22, 2021, is named GMI_195CN_Sequence_Listing.txt and is 43381 bytes in size.

FIELD

The present invention relates to bispecific antibodies targeting both CD3 and CD20 and the use of such antibodies in the treatment of chronic lymphocytic leukemia (CLL). Advantageous treatment regimens are also provided.

BACKGROUND

Chronic lymphocytic leukemia (CLL) is a B-cell malignancy that originates from uncontrolled proliferation of immature lymphocytes in the bone marrow and involves circulating tumor cells in the blood. CLL is characterized by accumulation of clonal CD5+CD19+CD20+CD23+ B cells in the bone marrow, blood, and lymphoid organs such as lymph nodes and spleen (Zenz et al., *Nat Rev Cancer* 2010; 10:37-50). CLL is often a slow-growing cancer. CLL is primarily a disease of older adults, with a median age of 70 years at the time of diagnosis. CLL is the most common leukemia in adults in Western countries, accounting for approximately 25% to 30% of all leukemias in the US with estimated 20,720 new cases and 3,930 deaths (Siegel et al., *CA Cancer J Clin* 2019; 69:7-34). Worldwide, there are approximately 105,000 cases per year, of which 35,000 are deaths (Global Burden of Disease Cancer, Fitzmaurice et al., *JAMA Oncol* 2018; 4:1553-68).

In contrast, lymphoma originates from uncontrolled proliferation of lymphocytes in organs outside of the bone marrow. Although in some lymphomas, bone marrow can also have tumor cell infiltrates. Lymphoma cells will usually not appear in the peripheral blood. Expression of CD20 was observed to be lower on CLL than on normal peripheral B cells or on other malignant NHL (Almasri et al., *Am J Hematol* 1992:40:259-63; Pedersen et al., *Blood* 2002; 99:1314-9; Prevodnik et al., *Diagn Pathol* 2011; 6:33; Olejniczak et al., *Immunol Invest* 2006; 35:93-114; Ginaldi et al., *J Clin Pathol* 1998; 51:364-9; D'Arena et al., *Am J Hematol* 2000; 64:275-81).

Most patients with newly diagnosed CLL present with an asymptomatic disease and can be monitored without therapy. For symptomatic or high-risk disease, standard of care includes cytotoxic chemotherapy (i.e. fludarabine, cyclophosphamide, bendamustine, or chlorambucil) in combination with an anti-CD20 monoclonal antibody (i.e., rituximab or obinutuzumab) (Goede et al., *N Engl J Med* 2014; 370-1101-10; Hallek et al., *Lancet* 2010; 376:1164-74). Although the treatment for CLL has been revolutionized by these chemo-immunotherapies, novel agents with a low toxicity profile are of particular importance as a replacement of these highly toxic and intensive regimens.

In recent years, chemotherapy-free regimens, such as ibrutinib plus rituximab (Burger et al., *Ann Intern Med* 2015; 163:461-4), venetoclax plus rituximab (Seymour et al., *N Engl J Med* 2018; 378:1107-20), venetoclax plus obinutuzumab (Fisher et al. *N Engl J Med;* 2019; 380(23):2225-36)), ibrutinib plus venetoclax (Niemann et al., *Blood* 2019; 134:4292; Tam et al., 2019 ASH Annual Meeting; Dec. 7 to 10, 2019; Orlando, FL. Abstract 35. bit.ly/2RvawBV), and acalabrutinib alone or in combination with obinutuzumab (Khan et al., *Future Oncol;* 2019; 15(6):579-89)) have shown promising results in both newly diagnosed and relapsed/refractory CLL. Despite these advantages, CLL remains an incurable disease outside of aggressive therapy with stem cell transplantation. In particular, patients who have early relapse from the combination of ibrutinib and venetoclax, or who were intolerant to targeted therapies pose a significant unmet medical need. Overall, CLL patients, especially those who have relapsed early while on ibrutinib or venetoxlax treatment or who are intolerant to target therapies, have very limited options.

There remains an unmet need with respect to treatment options for CLL patients, for example, those who have relapsed after or are intolerant to currently available therapies.

SUMMARY

Provided herein are methods of treating human subjects who have CLL by administering a bispecific antibody which binds to CD3 and CD20 and, in particular, advantageous clinical treatment regimens.

In one aspect, provided herein is a method of treating CLL, for example, relapsed and/or refractory CLL, in a human subject, the method comprising administering (e.g., subcutaneously) to the subject an effective amount of a bispecific antibody (e.g., epcoritamab) comprising:
(i) a first binding arm comprising a first antigen-binding region which binds to human CD3ε (epsilon) and comprises a variable heavy chain (VH) region and a variable light chain (VL) region, wherein the VH region comprises the CDR1, CDR2 and CDR3 sequences that are in the VH region sequence of SEQ ID NO: 6, and the VL region comprises the CDR1, CDR2 and CDR3 sequences that are in the VL region sequence of SEQ ID NO: 7; and
(ii) a second binding arm comprising a second antigen-binding region which binds to human CD20 and comprises a VH region and a VL region, wherein the VH region comprises the CDR1, CDR2 and CDR3 sequences that are in the VH region sequence of SEQ ID NO: 13, and the VL region comprises the CDR1, CDR2 and CDR3 sequences that are in the VL region sequence of SEQ ID NO: 14;
wherein the bispecific antibody is administered at a dose ranging from 12-60 mg in 28-days cycles. In some embodiments, the bispecific antibody is administered at a dose of (or a dose of about) 12 mg, 24 mg, 48 mg, or 60 mg. In some embodiments, the bispecific antibody is administered at a dose of (or a dose of about) 12 mg. In some embodiments, the bispecific antibody is administered at a dose of (or a dose of about) 24 mg.

In some embodiments, the bispecific antibody is administered at a dose of (or a dose of about) 48 mg. In some embodiments, the bispecific antibody is administered at a dose of (or a dose of about) 60 mg.

In some embodiments, the bispecific antibody is administered once every week, e.g., for 2.5 28-day cycles (i.e., days 15 and 22 of cycle 1, and days 1, 8, 15, and 22 of cycles 2-3). In some embodiments, the bispecific antibody is administered once every two weeks after the weekly administration, e.g., for six 28-day cycles. In some embodiments, the bispecific antibody is administered once every four weeks after the biweekly administration. In a further embodiment, a priming dose (e.g., 0.05-0.35 mg, for example, 0.16 mg or about 0.16 mg) of the bispecific antibody is administered two weeks prior to administering the weekly dose of 24 mg or 48 mg. In a further embodiment, the priming dose is administered one week before the intermediate dose, and the intermediate dose is administered one week before the first weekly dose of 24 mg or 48 mg.

In some embodiments, the bispecific antibody is administered in 28-day cycles, wherein:
a) in cycle 1, a priming dose (e.g., 0.05-0.35 mg, for example, 0.16 mg or about 0.16 mg) is administered on day 1, an intermediate dose (e.g., 0.6-1.2 mg, for example, 0.8 mg or about 0.8 mg) on day 8, and a full dose of 12-60 mg (e.g., 12 mg, 24 mg, 48 mg, or 60 mg) on days 15 and 22;
b) in cycles 2-3, a full dose of 12-60 mg (e.g., 12 mg, 24 mg, 48 mg, or 60 mg) is administered on days 1, 8, 15, and 22;
c) in cycles 4-9, a full dose of 12-60 mg (e.g., 12 mg, 24 mg, 48 mg, or 60 mg) is administered on days 1 and 15; and
d) in cycle 10 and subsequent cycles, a full dose of 12-60 mg (e.g., 12 mg, 24 mg, 48 mg, or 60 mg) is administered on day 1.

In some embodiments, the subject is intolerant to a BTK inhibitor. In some embodiments, the subject has received at least two prior lines of antineoplastic therapy, e.g., wherein at least one of the two prior lines of antineoplastic therapy comprises treatment with a BTK inhibitor, such as ibrutinib. In some embodiments, the subject's CLL is refractory to a BTK inhibitor (e.g., ibrutinib or acalabrutinib). In a further embodiment, the subject's CLL relapsed during treatment with a BTK inhibitor (ibrutinib). In a further embodiment, the subject has refractory and/or relapsed CLL after receiving the two prior antineoplastic therapies.

In some embodiments, the subject is treated with prophylaxis for cytokine release syndrome (CRS). In some embodiments, the prophylaxis comprises administering a corticosteroid (e.g., prednisolone at a dose of, e.g., 100 mg or equivalent thereof, including oral dose) on, for example, the same day as the bispecific antibody. In some embodiments, the corticosteroid is further administered on the second, third, and fourth days after administering the bispecific antibody.

In some embodiments, the subject is administered premedication, such as antihistamine (e.g., diphenhydramine, intravenously or orally at a dose of, e.g., 50 mg or equivalent thereof) and/or antipyretic (e.g., acetaminophen at a dose of, e.g., 560-1000 mg), to reduce reactions to injections. In some embodiments, the premedication is administered on the same day as the bispecific antibody.

In some embodiments, the prophylaxis and premedication are administered during cycle 1. In some embodiments, the prophylaxis is administered during cycle 2 when the subject experiences CRS greater than grade 1 after the last administration of the bispecific antibody in cycle 1. In some embodiments, the prophylaxis is continued in a subsequent cycle, when in the last administration of the bispecific antibody of the previous cycle, the subject experiences CRS greater than grade 1. In a further embodiment, the premedication is administered during cycle 2. In a further embodiment, the premedication is administered during subsequent cycles.

In some embodiments, the subject is treated with antipyretics and hydration if the subject develops Grade 1 CRS. In some embodiments, the subject is treated with tocilizumab and/or dexamethasone or its equivalent of methylprednisolone if the subject develops Grade 2 CRS. In some embodiments, the subject is treated with tocilizumab and dexamethasone (e.g., at a dose of 10-20 mg or its equivalent of methylprednisolone, e.g., administered once every 6 hours) if the subject develops Grade 3 CRS. In a further embodiment, the subject is treated with tocilizumab and methylprednisolone (e.g., at a dose of 1000 mg/day) if the subject develops Grade 4 CRS. In a further embodiment, tocilizumab is switched to siltuximab if the subject does not respond to tocilizumab.

In some embodiments, the subject is administered prophylaxis for tumor lysis syndrome (TLS). In some embodiments, the prophylaxis for TLS comprises administering one or more uric acid reducing agents prior to administration of the bispecific antibody. In some embodiments, allopurinol and rasburicase are administered as the uric acid reducing agents. In a further embodiment, allopurinol is administered at least 72 hours prior to administration of the bispecific antibody. In a further embodiment, rasburicase is administered after administering allopurinol and prior to administering the bispecific antibody. In some embodiments, when a subject shows signs of TLS, supportive therapy, such as rasburicase and/or allopurinol, may be used.

In some embodiments, the subject treated with the methods described herein achieves a complete response, a partial response, or stable disease, e.g., as defined by iwCLL response criteria.

In some embodiments, the first antigen-binding region of the bispecific antibody comprises VHCDR1, VHCDR2, and VHCDR3 comprising the amino acid sequences set forth in SEQ ID NOs: 1, 2, and 3, respectively, and VLCDR1, VLCDR2, and VLCDR3 comprising the amino acid sequences set forth in SEQ ID NO: 4, the sequence GTN, and SEQ ID NO: 5, respectively; and the second antigen-binding region comprises VHCDR1, VHCDR2, and VHCDR3 comprising the amino acid sequences set forth in SEQ ID NOs: 8, 9, and 10, respectively, and VLCDR1, VLCDR2, and VLCDR3 comprising the amino acid sequences set forth in SEQ ID NO: 11, the sequence DAS, and SEQ ID NO: 12, respectively.

In some embodiments, the first antigen-binding region of the bispecific antibody comprises a VH region comprising the amino acid sequence of SEQ ID NO: 6, and the VL region comprising the amino acid sequence of SEQ ID NO: 7; and the second antigen-binding region comprises a VH region comprising the amino acid sequence of SEQ ID NO: 13, and the VL region comprising the amino acid sequence of SEQ ID NO: 14.

In some embodiments, the first binding arm of the bispecific antibody is derived from a humanized antibody, preferably from a full-length IgG1,λ (lambda) antibody. In some embodiments, the second binding arm of the bispecific antibody is derived from a human antibody, preferably from a full-length IgG1,κ (kappa) antibody. In some embodiments, the bispecific antibody is a full-length antibody with a human IgG1 constant region.

In some embodiments, the bispecific antibody comprises an inert Fc region, for example, an Fc region in which the amino acids in the positions corresponding to positions L234, L235, and D265 in the human IgG1 heavy chain constant region of SEQ ID NO: 15 are F, E, and A, respectively. In some embodiments, the bispecific antibody comprises substitutions which promote bispecific antibody formation, for example, wherein in the first heavy chain, the amino acid in the position corresponding to F405 in the human IgG1 heavy chain constant region of SEQ ID NO: 15 is L, and wherein in the second heavy chain, the amino acid in the position corresponding to K409 in the human IgG1 heavy chain constant region of SEQ ID NO: 15 is R, or vice versa. In some embodiments, the bispecific antibody has both an inert Fc region (e.g., substitutions at L234, L235, and D265 (e.g., L234F, L235E, and D265A)) and substitutions which promote bispecific antibody formation (e.g., F405L and K409R). In a further embodiment, the bispecific antibody comprises heavy chain constant regions comprising the amino acid sequences of SEQ ID NOs: 19 and 20.

In some embodiments, the bispecific antibody comprises a first heavy chain and a first light chain comprising (or consisting of) the amino acid sequences set forth in SEQ ID NOs: 24 and 25, respectively, and a second heavy chain and a second light chain comprising (or consisting of) the amino acid sequences set forth in SEQ ID NOs: 26 and 27, respectively. In some embodiments, the bispecific antibody is epcoritamab, or a biosimilar thereof.

DETAILED DESCRIPTION

Definitions

Figure 1A:
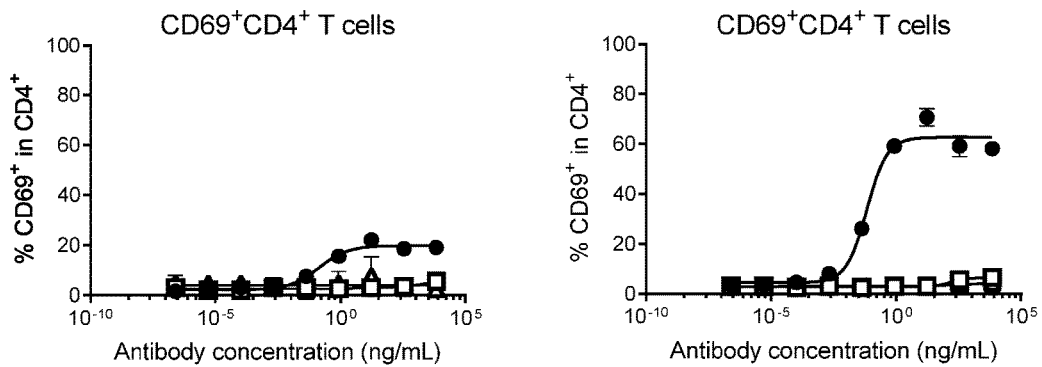
FIGS. 1A-1C are a series of graphs showing the effects of epcoritamab on CD4+ (FIG. 1A) and CD8+ (FIG. 1B) T cell activation, as well as B cell viability (FIG. 1C), in PBMCs obtained from a CLL patient (left panel) and a healthy donor (right panel). Data shown are percentages±SD of duplicate wells from one representative donor out of three donors tested. Panels on the left show results for PBMCs from the CLL patient (CFSE-negative), panels on the right for healthy donor PBMCs (CFSE-positive). Filled circles represent epcoritamab, open squares represent a control bispecific antibody containing a CD3-specific arm and a control (non-binding) arm, and open triangles represent a control bispecific antibody containing a CD20-specific arm and a control (non-binding) arm.

The term "immunoglobulin" as used herein refers to a class of structurally related glycoproteins consisting of two pairs of polypeptide chains, one pair of light (L) low molecular weight chains and one pair of heavy (H) chains, all four inter-connected by disulfide bonds. The structure of immunoglobulins has been well characterized (see, e.g., Fundamental Immunology Ch. 7 (Paul, W., ed., 2nd ed. Raven Press, N.Y. (1989)). Briefly, each heavy chain typically is comprised of a heavy chain variable region (abbreviated herein as VH or $V_H$) and a heavy chain constant region (abbreviated herein as CH or $C_H$). The heavy chain constant region typically is comprised of three domains, CH1, CH2, and CH3. The hinge region is the region between the CH1 and CH2 domains of the heavy chain and is highly flexible. Disulfide bonds in the hinge region are part of the interactions between two heavy chains in an IgG molecule. Each light chain typically is comprised of a light chain variable region (abbreviated herein as VL or VL) and a light chain constant region (abbreviated herein as CL or $C_L$). The light chain constant region typically is comprised of one domain, CL. The VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk J Mol Biol 1987; 196:90117). Unless otherwise stated or contradicted by context, CDR sequences herein are identified according to IMGT rules (Brochet X., *Nucl Acids Res* 2008; 36:W503-508; Lefranc M P., *Nucl Acids Res* 1999; 27:209-12; www.imgt.org/). Unless otherwise stated or contradicted by context, reference to amino acid positions in the constant regions is according to the EU-numbering (Edelman et al., *PNAS.* 1969; 63:78-85; Kabat et al., Sequences of Proteins of Immunological Interest, Fifth Edition. 1991 NIH Publication No. 91-3242). For example, SEQ ID NO: 15 sets forth amino acids positions 118-447, according to EU numbering, of the IgG1 heavy chain constant region.

The term "amino acid corresponding to position . . . " as used herein refers to an amino acid position number in a human IgG1 heavy chain. Corresponding amino acid positions in other immunoglobulins may be found by alignment with human IgG1. Thus, an amino acid or segment in one sequence that "corresponds to" an amino acid or segment in another sequence is one that aligns with the other amino acid or segment using a standard sequence alignment program such as ALIGN, ClustalW or similar, typically at default settings and has at least 50%, at least 80%, at least 90%, or at least 95% identity to a human IgG1 heavy chain. It is within the ability of one of ordinary skill in the art to align a sequence or segment in a sequence and thereby determine the corresponding position in a sequence to an amino acid position according to the present invention.

The term "antibody" (Ab) as used herein in the context of the present invention refers to an immunoglobulin molecule which has the ability to specifically bind to an antigen under typical physiological conditions with a half-life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The term antibody, unless specified otherwise, also encompasses polyclonal antibodies, monoclonal antibodies (mAbs), antibody-like polypeptides, chimeric antibodies and humanized antibodies. An antibody as generated can possess any isotype.

The term "antibody fragment" or "antigen-binding fragment" as used herein refers to a fragment of an immunoglobulin molecule which retains the ability to specifically bind to an antigen, and can be generated by any known technique, such as enzymatic cleavage, peptide synthesis, and recombinant techniques. Examples of antibody fragments include (i) a Fab' or Fab fragment, a monovalent fragment consisting of the VL, VH, CL and CH1 domains, or a monovalent antibody as described in WO2007059782 (Genmab); (ii) F(ab')2 fragments, bivalent fragments comprising two Fab fragments linked by a disulfide bridge at the hinge region; (iii) a Fd fragment consisting essentially of the VH and CH1 domains; (iv) a Fv fragment consisting essentially of the VL and VH domains of a single arm of an antibody, (v) a dAb fragment (Ward et al., Nature 1989; 341: 54446), which consists essentially of a VH domain and also called domain antibodies (Holt et al; Trends Biotechnol 2003; 21:484-90); (vi) camelid or nanobodies (Revets et al; Expert Opin Biol Ther 2005; 5:111-24) and (vii) an isolated complementarity determining region (CDR). Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain antibodies or single chain Fv (scFv), see, e.g., Bird et al., Science 1988; 242:42326 and Huston et al., PNAS 1988; 85:587983). Such single chain antibodies are encompassed within the term antibody fragment unless otherwise noted or clearly indicated by context.

The term "antibody-binding region" or "antigen-binding region" as used herein refers to the region which interacts with the antigen and comprises both the VH and the VL regions. The term antibody when used herein refers not only to monospecific antibodies, but also multispecific antibodies which comprise multiple, such as two or more, e.g., three or more, different antigen-binding regions. The term antigen-binding region, unless otherwise stated or clearly contradicted by context, includes fragments of an antibody that are antigen-binding fragments, i.e., retain the ability to specifically bind to the antigen.

As used herein, the term "isotype" refers to the immunoglobulin class (for instance IgG1, IgG2, IgG3, IgG4, IgD, IgA, IgE, or IgM) that is encoded by heavy chain constant region genes. When a particular isotype, e.g., IgG1, is mentioned, the term is not limited to a specific isotype sequence, e.g., a particular IgG1 sequence, but is used to indicate that the antibody is closer in sequence to that isotype, e.g. IgG1, than to other isotypes. Thus, e.g., an IgG1 antibody may be a sequence variant of a naturally-occurring IgG1 antibody, which may include variations in the constant regions.

The term "bispecific antibody" or "bs" or "bsAb" as used herein refers to an antibody having two different antigen-binding regions defined by different antibody sequences. A bispecific antibody can be of any format.

The terms "half molecule", "Fab-arm", and "arm", as used herein, refer to one heavy chain-light chain pair.

When a bispecific antibody is described as comprising a half-molecule antibody "derived from" a first parental antibody, and a half-molecule antibody "derived from" a second parental antibody, the term "derived from" indicates that the bispecific antibody was generated by recombining, by any known method, said half-molecules from each of said first and second parental antibodies into the resulting bispecific antibody. In this context, "recombining" is not intended to be limited by any particular method of recombining and thus includes all of the methods for producing bispecific antibodies described herein, including for example recombining by half-molecule exchange (also known as "controlled Fab-arm exchange"), as well as recombining at nucleic acid level and/or through co-expression of two half-molecules in the same cells.

The term "full-length" as used herein in the context of an antibody indicates that the antibody is not a fragment but contains all of the domains of the particular isotype normally found for that isotype in nature, e.g., the VH, CH1, CH2, CH3, hinge, VL and CL domains for an IgG1 antibody. A full-length antibody may be engineered. An example of a "full-length" antibody is epcoritamab.

The term "Fc region" as used herein refers to an antibody region consisting of the Fc sequences of the two heavy chains of an immunoglobulin, wherein said Fc sequences comprise at least a hinge region, a CH2 domain, and a CH3 domain.

The term "heterodimeric interaction between the first and second CH3 regions" as used herein refers to the interaction between the first CH3 region and the second CH3 region in a first-CH3/second-CH3 heterodimeric protein.

The term "homodimeric interactions of the first and second CH3 regions" as used herein refers to the interaction between a first CH3 region and another first CH3 region in a first-CH3/first-CH3 homodimeric protein and the interaction between a second CH3 region and another second CH3 region in a second-CH3/second-CH3 homodimeric protein.

The term "binding" as used herein in the context of the binding of an antibody to a predetermined antigen typically refers to binding with an affinity corresponding to a $K_D$ of about $10^{-6}$M or less, e.g., $10^{-7}$ M or less, such as about $10^{-8}$M or less, such as about $10^{-9}$ M or less, about $10^{-10}$ M or less, or about $10^{-11}$M or even less, when determined by, e.g., BioLayer Interferometry (BLI) technology in a Octet HTX instrument using the antibody as the ligand and the antigen as the analyte, and wherein the antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its $K_D$ of binding to a non-specific antigen (e.g., BSA, casein) other than the predetermined antigen or a closely related antigen. The amount with which the $K_D$ of binding is lower is dependent on the $K_D$ of the antibody, so that when the $K_D$ of the antibody is very low, then the amount with which the $K_D$ of binding to the antigen is lower than the $K_D$ of binding to a non-specific antigen may be at least 10,000-fold (i.e., the antibody is highly specific).

The term "$K_D$" (M) as used herein refers to the dissociation equilibrium constant of a particular antibody-antigen interaction. Affinity, as used herein, and $K_D$ are inversely related, that is that higher affinity is intended to refer to lower $K_D$, and lower affinity is intended to refer to higher $K_D$.

The term "isolated antibody" as used herein refers to an antibody which is substantially free of other antibodies having different antigenic specificities. In a preferred embodiment, an isolated bispecific antibody that specifically binds to CD20 and CD3 is in addition substantially free of monospecific antibodies that specifically bind to CD20 or CD3.

The term "CD3" as used herein refers to the human Cluster of Differentiation 3 protein which is part of the T-cell co-receptor protein complex and is composed of four distinct chains. CD3 is also found in other species, and thus, the term "CD3" is not limited to human CD3 unless contradicted by context. In mammals, the complex contains a CD3γ (gamma) chain (human CD3γ chain UniProtKB/Swiss-Prot No P09693, or cynomolgus monkey CD3γ UniProtKB/Swiss-Prot No Q95LI7), a CD3δ chain (human CD3δ UniProtKB/Swiss-Prot No P04234, or cynomolgus monkey CD3δ UniProtKB/Swiss-Prot No Q95LI8), two CD3ε (epsilon) chains (human CD3ε UniProtKB/Swiss-Prot No P07766, SEQ ID NO: 28); cynomolgus CD3ε UniProtKB/Swiss-Prot No Q95LI5; or rhesus CD3ε UniProtKB/Swiss-Prot No G7NCB9), and a CD3ζ-chain (zeta) chain (human CD3ζ UniProtKB/Swiss-Prot No P20963, cynomolgus monkey CD3ζ UniProtKB/Swiss-Prot No Q09TK0). These chains associate with a molecule known as the T-cell receptor (TCR) and generate an activation signal in T lymphocytes. The TCR and CD3 molecules together comprise the TCR complex.

The term "CD3 antibody" or "anti-CD3 antibody" as used herein refers to an antibody which binds specifically to the antigen CD3, in particular human CD3ε (epsilon).

The term "human CD20" or "CD20" refers to human CD20 (UniProtKB/Swiss-Prot No P11836, SEQ ID NO: 29) and includes any variants, isoforms, and species homologs of CD20 which are naturally expressed by cells, including tumor cells, or are expressed on cells transfected with the CD20 gene or cDNA. Species homologs include rhesus monkey CD20 (*Macaca mulatta*; UniProtKB/Swiss-Prot No H9YXP1) and cynomolgus monkey CD20 (*Macaca fascicularis*; UniProtKB No G7PQ03).

The term "CD20 antibody" or "anti-CD20 antibody" as used herein refers to an antibody which binds specifically to the antigen CD20, in particular to human CD20.

The term "CD3xCD20 antibody", "anti-CD3xCD20 antibody", "CD20xCD3 antibody" or "anti-CD20xCD3 antibody" as used herein refers to a bispecific antibody which comprises two different antigen-binding regions, one of which binds specifically to the antigen CD20 and one of which binds specifically to CD3.

The term "DuoBody-CD3xCD20" as used herein refers to an IgG1 bispecific CD3xCD20 antibody comprising a first heavy and light chain pair as defined in SEQ ID NO: 24 and SEQ ID NO: 25, respectively, and comprising a second heavy and light chain pair as defined in SEQ ID NO: 26 and SEQ ID NO: 27. The first heavy and light chain pair comprises a region which binds to human CD3ε (epsilon), the second heavy and light chain pair comprises a region which binds to human CD20. The first binding region comprises the VH and VL sequences as defined by SEQ ID NOs: 6 and 7, and the second binding region comprises the VH and VL sequences as defined by SEQ ID NOs: 13 and 14. This bispecific antibody can be prepared as described in WO 2016/110576.

Antibodies comprising functional variants of the heavy chain, light chains, VL regions, VH regions, or one or more CDRs of the antibodies of the examples as also provided herein. A functional variant of a heavy chain, a light chain, VL, VH, or CDRs used in the context of an antibody still allows the antibody to retain at least a substantial proportion (at least about 90%, 95% or more) of functional features of the "reference" and/or "parent" antibody, including affinity and/or the specificity/selectivity for particular epitopes of CD20 and/or CD3, Fc inertness and PK parameters such as half-life, Tmax, Cmax. Such functional variants typically retain significant sequence identity to the parent antibody and/or have substantially similar length of heavy and light chains. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm. Exemplary variants include those which differ from heavy and/or light chains, VH and/or VL, and/or CDR regions of the parent antibody sequences mainly by conservative substitutions; e.g., 10, such as 9, 8, 7, 6, 5, 4, 3, 2 or 1 of the substitutions in the variant may be conservative amino acid residue replacements.

Conservative substitutions may be defined by substitutions within the classes of amino acids reflected in the following table:

TABLE 1

| Amino acid residue classes for conservative substitutions | |
| --- | --- |
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Unless otherwise indicated, the following nomenclature is used to describe a mutation: i) substitution of an amino acid in a given position is written as, e.g., K409R which means a substitution of a Lysine in position 409 with an Arginine; and ii) for specific variants the specific three or one letter codes are used, including the codes Xaa and X to indicate any amino acid residue. Thus, the substitution of Lysine with Arginine in position 409 is designated as: K409R, and the substitution of Lysine with any amino acid residue in position 409 is designated as K409X. In case of deletion of Lysine in position 409 it is indicated by K409*.

The term "humanized antibody" as used herein refers to a genetically engineered non-human antibody, which contains human antibody constant domains and non-human variable domains modified to contain a high level of sequence homology to human variable domains. This can be achieved by grafting of the six non-human antibody CDRs, which together form the antigen binding site, onto a homologous human acceptor framework region (FR) (see WO92/22653 and EP0629240). In order to fully reconstitute the binding affinity and specificity of the parental antibody, the substitution of framework residues from the parental antibody (i.e., the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. The VH and VL of the CD3 arm that is used herein in DuoBody-CD3xCD20 represents a humanized antigen-binding region. Optionally, additional amino acid modifications, which are not necessarily back-mutations, may be applied to obtain a humanized antibody with preferred characteristics, such as affinity and biochemical properties.

The term "human antibody" as used herein refers to antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The VH and VL of the CD20 arm that is used in DuoBody-CD3xCD20 represents a human antigen-binding region. Human monoclonal antibodies of the invention can be produced by a variety of techniques, including conventional monoclonal antibody methodology, e.g., the standard somatic cell hybridization technique of Kohler and Milstein, *Nature* 256: 495 (1975). Although somatic cell hybridization procedures are preferred, in principle, other techniques for producing monoclonal antibody can be employed, e.g., viral or oncogenic transformation of B-lymphocytes or phage display techniques using libraries of human antibody genes. A suitable animal system for preparing hybridomas that secrete human monoclonal antibodies is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known. Human monoclonal antibodies can thus be generated using, e.g., transgenic or transchromosomal mice or rats carrying parts of the human immune system rather than the mouse or rat system. Accordingly, in one embodiment, a human antibody is obtained from a transgenic animal, such as a mouse or a rat, carrying human germline immunoglobulin sequences instead of animal immunoglobulin sequences. In such embodiments, the antibody originates from human germline immunoglobulin sequences introduced in the animal, but the final antibody sequence is the result of said human germline immunoglobulin sequences being further modified by somatic hypermutations and affinity maturation by the endogenous animal antibody machinery (see, e.g., Mendez et al. *Nat Genet* 1997; 15:146-56). The VH and VL regions of the CD20 arm that is used in DuoBody-CD3xCD20 represents a human antigen-binding region.

The term "biosimilar" (e.g., of an approved reference product/biological drug) as used herein refers to a biologic product that is similar to the reference product based on data from (a) analytical studies demonstrating that the biological product is highly similar to the reference product notwithstanding minor differences in clinically inactive components; (b) animal studies (including the assessment of toxicity); and/or (c) a clinical study or studies (including the assessment of immunogenicity and pharmacokinetics or pharmacodynamics) that are sufficient to demonstrate safety, purity, and potency in one or more appropriate conditions of use for which the reference product is approved and intended to be used and for which approval is sought (e.g., that there are no clinically meaningful differences between the biological product and the reference product in terms of the safety, purity, and potency of the product). In some embodiments, the biosimilar biological product and reference product utilizes the same mechanism or mechanisms of action for the condition or conditions of use prescribed, recommended, or suggested in the proposed labeling, but only to the extent the mechanism or mechanisms of action are known for the reference product. In some embodiments, the condition or conditions of use prescribed, recommended, or suggested in the labeling proposed for the biological product have been previously approved for the reference product. In some embodiments, the route of administration, the dosage form, and/or the strength of the biological product are the same as those of the reference product. A biosimilar can be, e.g., a presently known antibody having the same primary amino acid sequence as a marketed antibody, but may be made in different cell types or by different production, purification, or formulation methods.

The term "reducing conditions" or "reducing environment" as used herein refers to a condition or an environment in which a substrate, here a cysteine residue in the hinge region of an antibody, is more likely to become reduced than oxidized.

The term "recombinant host cell" (or simply "host cell") as used herein is intended to refer to a cell into which an expression vector has been introduced, e.g., an expression vector encoding an antibody described herein. Recombinant host cells include, for example, transfectomas, such as CHO, CHO-S, HEK, HEK293, HEK-293F, Expi293F, PER.C6 or NS0 cells, and lymphocytic cells.

As used herein, "chronic lymphocytic leukemia" or "CLL" refers to a disorder of morphologically mature but immunologically less mature lymphocytes and is manifested by progressive accumulation of these cells in the blood, bone marrow, and lymphatic tissues. CLL can be diagnosed and classified based on WHO classification, which is included herein by reference (Swerdlow S H, Campo E, Harris N L, et al. WHO Classification of Tumours of Haematopoietic and Lymphoid Tissues (Revised ed. 4th). Lyon, France: IARC Press (2017); Swerdlow S H, Campo E, Harris N L, et al. WHO Classification of Tumours of Haematopoietic and Lymphoid Tissues (ed. 4th). Lyon, France: IARC Press (2008)). CLL starts from lymphocytes in the bone marrow, and most commonly occurs in those aged >50 years. It is characterized by the clonal proliferation and accumulation of mature B lymphocytes, which ultimately leads to monoclonal B-cell lymphocytosis (reviewed in Uhm, *Blood Res* 2020; 55:S72-82). Monoclonal B cells in CLL express several markers that are characteristic of mature activated B lymphocytes, including CD5, CD19, CD20 and CD23, as well as reduced expression of IgGM, IgGD, and CD79b (Chiorazzi et al., *N Engl J Med* 2005; 352-804-15). Several prognostic markers have been reported for the disease, including mutations in the IGHV gene, mutations in TP53, del(17p), and del(11q) (Wierda et al., *J Clin Oncol* 2011; 29:4088-95; Rossi et al., *Blood* 2013-121:1403-12; CLL-IPI, *Lancet Oncol* 2016; 17:779-90). Treatments for CLL include, for example, chemotherapy, BCL2 inhibitors, BTK inhibitors, PI3Kδ inhibitors, alone or in combination with anti-CD20 antibodies, (Uhm, 2020, supra).

The term "treatment" refers to the administration of an effective amount of a therapeutically active antibody described herein for the purpose of easing, ameliorating, arresting or eradicating (curing) symptoms or disease states such as CLL. Treatment may result in a complete response (CR), partial response (PR), or stable disease (SD), for example, as defined by iwCLL response criteria, as shown in Table 2. Treatment may be continued, for example, until disease progression (PD) or unacceptable toxicity.

The term "administering" or "administration" as used herein refers to the physical introduction of a composition (or formulation) comprising a therapeutic agent to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, a therapeutic agent described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods. In the methods described herein, the bispecific antibody (e.g., epcoritamab) is administered subcutaneously. Other agents used in combination with the bispecific antibody, such as for cytokine release syndrome prophylaxis or tumor lysis syndrome (TLS) prophylaxis, may be administered via other routes, such as intravenously or orally.

The term "effective amount" or "therapeutically effective amount" refers to an amount effective, at dosages and for periods of time necessary, to achieve a desired therapeutic result. For example, dosages as defined herein for the bispecific antibody (e.g., epcoritamab) in the range of 12-60 mg administered subcutaneously can be defined as such an "effective amount" or "therapeutically effective amount". A therapeutically effective amount of an antibody may vary according to factors such as the disease state, age, sex, and weight of the individual, and the ability of the antibody to elicit a desired response in the individual. A therapeutically effective amount is also one in which any toxic or detrimental effects of the antibody or antibody portion are outweighed by the therapeutically beneficial effects. In some embodiments, patients treated with the methods described herein will show an improvement in ECOG performance status. A therapeutically effective amount or dosage of a drug includes a "prophylactically effective amount" or a "prophylactically effective dosage", which is any amount of the drug that, when administered alone or in combination with another therapeutic agent to a subject at risk of developing a disease or disorder (e.g., cytokine release syndrome) or of suffering a recurrence of disease, inhibits the development or recurrence of the disease.

The term "inhibits growth" of a tumor as used herein includes any measurable decrease in the growth of a tumor, e.g., the inhibition of growth of a tumor by at least about 10%, for example, at least about 20%, at least about 30%, at least about 40%, at least about 50%, at least about 60%, at least about 70%, at least about 80%, at least about 90%, at least about 99%, or 100%.

The term "subject" as used herein refers to a human patient, for example, a human patient with CLL. The terms "subject" and "patient" are used interchangeably herein.

The term "buffer" as used herein denotes a pharmaceutically acceptable buffer. The term "buffer" encompasses those agents which maintain the pH value of a solution, e.g., in an acceptable range and includes, but is not limited to, acetate, histidine, TRIS® (tris (hydroxymethyl) aminomethane), citrate, succinate, glycolate and the like. Generally, the "buffer" as used herein has a pKa and buffering capacity suitable for the pH range of about 5 to about 6, preferably of about 5.5.

"Disease progression" or "PD" as used herein refers to a situation in which one or more indices of CLL show that the disease is advancing despite treatment. In some embodiments, disease progression is defined based on iwCLL response criteria, as shown in Table 2.

A "surfactant" as used herein is a compound that is typically used in pharmaceutical formulations to prevent drug adsorption to surfaces and or aggregation. Furthermore, surfactants lower the surface tension (or interfacial tension) between two liquids or between a liquid and a solid. For example, an exemplary surfactant can significantly lower the surface tension when present at very low concentrations (e.g., 5% w/v or less, such as 3% w/v or less, such as 1% w/v or less such as 0.4% w/v or less, such as below 0.1% w/v or less, such as 0.04% w/v). Surfactants are amphiphilic, which means they are usually composed of both hydrophilic and hydrophobic or lipophilic groups, thus being capable of forming micelles or similar self-assembled structures in aqueous solutions. Known surfactants for pharmaceutical use include glycerol monooleate, benzethonium chloride, sodium docusate, phospholipids, polyethylene alkyl ethers, sodium lauryl sulfate and tricaprylin (anionic surfactants); benzalkonium chloride, citrimide, cetylpyridinium chloride and phospholipids (cationic surfactants); and alpha tocopherol, glycerol monooleate, myristyl alcohol, phospholipids, poloxamers, polyoxyethylene alkyl ethers, polyoxyethylene castor oil derivatives, polyoxyethylene sorbintan fatty acid esters, polyoxyethylene sterarates, polyoxyl hydroxystearate, polyoxylglycerides, polysorbates such as polysorbate 20 or polysorbate 80, propylene glycol dilaurate, propylene glycol monolaurate, sorbitan esters sucrose palmitate, sucrose stearate, tricaprylin and TPGS (Nonionic and zwitterionic surfactants).

A "diluent" as used herein is one which is pharmaceutically acceptable (safe and non-toxic for administration to a human) and is useful for the preparation of dilutions of the pharmaceutical composition or pharmaceutical formulation (the terms "composition" and "formulation" are used interchangeably herein). Preferably, such dilutions of the composition dilute only the antibody concentration but not the buffer and stabilizer. Accordingly, in one embodiment, the diluent contains the same concentrations of the buffer and stabilizer as is present in the pharmaceutical composition of the invention. Further exemplary diluents include sterile water, bacteriostatic water for injection (BWFI), a pH buffered solution which is preferably an acetate buffer, sterile saline solution, Ringer's solution or dextrose solution. In one embodiment the diluent comprises or consists essentially of acetate buffer and sorbitol.

As used herein, the term "about" refers to ±10% of a specified value.

CLL Treatment Regimens

Provided herein are methods of treating CLL in a human subject using a bispecific antibody which binds to CD3 and CD20 ("anti-CD3xCD20 antibody"), e.g., an isolated anti-CD3xCD20 antibody which binds to human CD3 and human CD20. The methods are also useful for treating recurrent or refractory CLL (R/R CLL). It is understood that the methods of treating CLL with a bispecific antibody which binds to both CD3 and CD20 described herein also encompass corresponding uses of the bispecific antibody for treating CLL in a human subject.

Accordingly, in one aspect, provided herein is a method of treating CLL in a human subject, the method comprising administering (e.g., subcutaneously) to the subject an effective amount of a bispecific antibody comprising:

(i) a first binding arm comprising a first antigen-binding region which binds to human CD3ε (epsilon) and comprises a variable heavy chain (VH) region and a variable light chain (VL) region, wherein the VH region comprises the CDR1, CDR2 and CDR3 sequences that are in the VH region sequence of SEQ ID NO: 6, and the VL region comprises the CDR1, CDR2 and CDR3 sequences that are in the VL region sequence of SEQ ID NO: 7; and (ii) a second binding arm comprising a second antigen-binding region which binds to human CD20 and comprises a VH region and a VL region, wherein the VH region comprises the CDR1, CDR2 and CDR3 sequences that are in the VH region sequence of SEQ ID NO: 13, and the VL region comprises the CDR1, CDR2 and CDR3 sequences that are in the VL region sequence of SEQ ID NO: 14;

wherein the bispecific antibody is administered at a dose ranging from 12-60 mg in 28-days cycles.

In some embodiments, the bispecific antibody is a full length antibody. In some embodiments, the bispecific antibody is an antibody with an inert Fc region. In some embodiments, the bispecific antibody is a full length antibody with an inert Fc region.

In some embodiments, the bispecific antibody is administered at a dose of (or a dose of about) 12 mg. In some embodiments, the bispecific antibody is administered at a dose of (or a dose of about) 24 mg. In some embodiments, the bispecific antibody is administered at a dose of (or a dose of about) 48 mg. In some embodiments, the bispecific antibody is administered at a dose of (or a dose of about) 60 mg.

With regard to the dose of 12-60 mg of the bispecific antibody that is to be administered, or any other specified dose, it is understood that this amount refers to the amount of a bispecific antibody representing a full-length antibody, such as epcoritamab as defined in the Examples section. Hence, one may refer to administering a dose of a bispecific antibody of 24 mg as administering a dose of a bispecific antibody described herein, wherein the dose corresponds to a dose of 24 mg of epcoritamab. One of ordinary skill in the art can readily determine the amount of antibody to be administered when, for example, the antibody used differs substantially in molecular weight from the molecular weight of a full-length antibody such as epcoritamab. For instance, the amount of antibody can be calculated by dividing the molecular weight of the antibody by the weight of a full-length antibody such as epcoritamab and multiplying the outcome thereof with the specified dose as described herein. As long as the bispecific antibody (e.g., a functional variant of DuoBody-CD3xCD20) has highly similar features as DuoBody-CD3xCD20, with regard to plasma half-life, Fc inertness, and/or binding characteristics for CD3 and CD20, i.e., with regard to CDRs and epitope binding features, such antibodies are suitable for use in the methods provided herein at a dose described for a full-length antibody such as epcoritamab.

In one embodiment, the bispecific anti-CD3xCD20 antibody is administered at a dose in the range of between 12 mg and 60 mg. In some embodiments, the bispecific antibody is administered at a dose of 12 mg or about 12 mg. In some embodiments, the bispecific antibody is administered at a dose of 24 mg or about 24 mg. In some embodiments, the bispecific antibody is administered at a dose of 48 mg or about 48 mg. In some embodiments, the bispecific antibody is administered at a dose of 60 mg or about 60 mg.

In some embodiments, the dose of bispecific antibody is administered once every week (weekly administration) in 28-day cycles. In some embodiments, the weekly administration is performed for 2.5 28-day cycles (i.e., 10 times). In one embodiment, the dose is administered for 2.5 28-day cycles (i.e., 10 times; on days 15 and 22 of cycle 1, and days 1, 8, 15, and 22 of cycles 2 and 3). In some embodiments, after said weekly administration, one may reduce the interval of administrating the bispecific antibody to an administration once every two weeks (biweekly administration). In some embodiments, such biweekly administration may be performed for six 28-day cycles (i.e., 12 times). In some embodiments, after said biweekly administration, the interval of administrating the bispecific antibody may be reduced further to once every four weeks. In one embodiment, the administration once every four weeks may be performed for an extended period, for example, for at least 1 cycle, at least 2 cycles, at least 3 cycles, at least 4 cycles, at least 5 cycles, at least 6 cycles, at least 7 cycles, at least 8 cycles, at least 9 cycles, at least 10 cycles, at least 11 cycles, at least 12 cycles, at least 13 cycles, at least 14 cycles, at least 15 cycles, at least 16 cycles, at least 17 cycles, or between 1-20 cycles, 1-19 cycles, 1-18 cycles, 1-17 cycles, 1-16 cycles, 1-15 cycles, 1-14 cycles, 1-13 cycles, 1-12 cycles, 1-10 cycles, 1-5 cycles, 5-20 cycles, 5-15 cycles, or 5-10 cycles of the 28-day cycles. In some embodiments, epcoritamab is administered once every four weeks until disease progression (e.g., as defined by the iwCLL response criteria, as shown in Table 2) or unacceptable toxicity. In one embodiment, the weekly dose is administered on cycles 1-3 (and may include priming and intermediate doses, as described below), the biweekly dose is administered on cycles 4-9, and the dose once every four weeks is administered from cycle 10 onward.

It is understood that the doses referred to herein may also be referred to as a full or a flat dose in the scenarios above wherein, e.g., the weekly dose, the biweekly dose, and/or the dose every four weeks is administered is at the same level. Accordingly, when a dose of 48 mg is selected, preferably, at each weekly administration, each biweekly administration, and each administration every four weeks, the same dose of 48 mg is administered. Prior to administering the dose, a priming or a priming and subsequent intermediate (second priming) dose may be administered. This may be advantageous as it may help mitigate cytokine release syndrome (CRS) risk and severity, a side-effect that can occur during treatment with the bispecific anti-CD3xCD20 antibody described herein. Such priming, or priming and intermediate doses, are at a lower dose as compared with the flat or full dose.

Accordingly, in some embodiments, prior to administering the weekly dose of 12-60 mg, a priming dose of the bispecific antibody may be administered. In one embodiment, the priming dose is administered two weeks prior to administering the first weekly dose of 12-60 mg in cycle 1. The priming dose may be in the range of 20-2000 µg (0.02 mg-2 mg), for example, in the range of 50-1000 µg (0.05 mg to 1 mg) or in the range of 70-350 µg (0.07 mg to 0.35 mg). The priming dose can be, for example, 80, 100, 120, 140, 160, 180, 200, 220, 240, 260, 280, 300, 320, 350, 400, 450, 500, 600, 700, 800, 900, or 1000 µg, or about 80, about 100, about 120, about 140, about 160, about 180, about 200, about 220, about 240, about 260, about 280, about 300, about 320, about 350, about 400, about 450, about 500, about 600, about 700, about 800, about 900, or about 1000 µg. In a preferred embodiment, the priming dose is in the range of 50 and 350 µg (0.05 and 0.35 mg, respectively). In a more preferred embodiment, the priming dose is 160 µg (0.16 mg) or about 160 µg (about 0.16 mg). In most preferred embodiments, the priming dose is 160 µg (0.16 mg) or about 160 µg (about 0.16 mg) of the full-length bispecific antibody.

In some embodiments, after administering the priming dose and prior to administering the first weekly dose of 12-60 mg, an intermediate dose of said bispecific antibody is administered. In one embodiment, the priming dose is administered on day 1 and the intermediate dose is administered on day 8 before the first weekly dose of 12-60 mg on days 15 and 22 of cycle 1 i.e. the priming dose is administered one week before the intermediate dose (i.e., day 1 of cycle 1), and the intermediate dose is administered one week before the first weekly dose of 12-60 mg (day 8 of cycle 1). The intermediate dose is selected from a range in between the priming dose and the flat or full dose. For example, the intermediate dose may be in the range of 200-8000 µg (0.2-8 mg), e.g., in the range of 400-4000 µg (0.4-4 mg) or 600-2000 µg (0.6-2 mg). The intermediate dose can be, for example, 200, 300, 400, 500, 600, 700, 800, 900, 1000, 1100, 1200, 1300, 1400, 1500, or 1600 µg, or about 200, about 300, about 400, about 500, about 600, about 700, about 800, about 900, about 1000, about 1100, about 1200, about 1300, about 1400, about 1500, or about 1600 µg. In a preferred embodiment, the intermediate dose is in the range of 600 and 1200 µg (0.6 and 1.2 mg, respectively). In a more preferred embodiment, the intermediate dose is 800 µg (0.8 mg) or about 800 µg (0.8 mg). In a most preferred embodiment, the intermediate dose is 800 µg or about 800 µg (0.8 mg) of the full-length bispecific antibody.

In some embodiments, the bispecific antibody is administered (e.g., subcutaneously) in 28-day cycles, wherein
a) in cycle 1, a priming dose is administered on day 1, an intermediate dose on day 8, and a full dose of 12-60 mg on days 15 and 22;
b) in cycles 2-3, a full dose of 12-60 mg is administered on days 1, 8, 15, and 22;
c) in cycles 4-9, a full dose of 12-60 mg is administered on days 1 and 15; and
d) in cycle 10 and subsequent cycles, a full dose of 12-60 mg is administered on day 1.

In some embodiments, the bispecific antibody is administered (e.g., subcutaneously) in 28-day cycles, wherein
a) in cycle 1, a priming dose in the range of 0.05-0.35 is administered on day 1, an intermediate dose in the range of 0.6-1.2 mg on day 8, and a full dose of 12-60 mg on days 15 and 22;
b) in cycles 2-3, a full dose of 12-60 mg is administered on days 1, 8, 15, and 22;
c) in cycles 4-9, a full dose of 12-60 mg is administered on days 1 and 15; and
d) in cycle 10 and subsequent cycles, a full dose of 12-60 mg is administered on day 1.

In some embodiments, the bispecific antibody is administered (e.g., subcutaneously) in 28-day cycles, wherein
a) in cycle 1, a priming dose of 160 µg is administered on day 1, an intermediate dose of 800 µg on day 8, and a full dose of 12-60 mg on days 15 and 22;
b) in cycles 2-3, a full dose of 12-60 mg is administered on days 1, 8, 15, and 22;
c) in cycles 4-9, a full dose of 12-60 mg is administered on days 1 and 15; and
d) in cycle 10 and subsequent cycles, a full dose of 12-60 mg is administered on day 1.

In some embodiments, the bispecific antibody is administered (e.g., subcutaneously) in 28-day cycles, wherein
a) in cycle 1, a priming dose is administered on day 1, an intermediate dose on day 8, and a full dose of 12 mg or about 12 mg on days 15 and 22;
b) in cycles 2-3, a full dose of 12 mg or about 12 mg is administered on days 1, 8, 15, and 22;
c) in cycles 4-9, a full dose of 12 mg or about 12 mg is administered on days 1 and 15; and
d) in cycle 10 and subsequent cycles, a full dose of 12 mg or about 12 mg is administered on day 1.

In some embodiments, the bispecific antibody is administered (e.g., subcutaneously) in 28-day cycles, wherein
a) in cycle 1, a priming dose in the range of 0.05-0.35 is administered on day 1, an intermediate dose in the range of 0.6-1.2 mg on day 8, and a full dose of 12 mg on days 15 and 22;
b) in cycles 2-3, a full dose of 12 mg is administered on days 1, 8, 15, and 22;
c) in cycles 4-9, a full dose of 12 mg is administered on days 1 and 15; and
d) in cycle 10 and subsequent cycles, a full dose of 12 mg is administered on day 1.

In some embodiments, the bispecific antibody is administered (e.g., subcutaneously) in 28-day cycles, wherein
a) in cycle 1, a priming dose of 160 µg is administered on day 1, an intermediate dose of 800 µg on day 8, and a full dose of 12 mg or about 12 mg on days 15 and 22;
b) in cycles 2-3, a full dose of 12 mg or about 12 mg is administered on days 1, 8, 15, and 22;
c) in cycles 4-9, a full dose of 12 mg or about 12 mg is administered on days 1 and 15; and
d) in cycle 10 and subsequent cycles, a full dose of 12 mg or about 12 mg is administered on day 1.

In some embodiments, the bispecific antibody is administered (e.g., subcutaneously) in 28-day cycles, wherein
a) in cycle 1, a priming dose is administered on day 1, an intermediate dose on day 8, and a full dose of 24 mg or about 24 mg on days 15 and 22;
b) in cycles 2-3, a full dose of 24 mg or about 24 mg is administered on days 1, 8, 15, and 22;
c) in cycles 4-9, a full dose of 24 mg or about 24 mg is administered on days 1 and 15; and
d) in cycle 10 and subsequent cycles, a full dose of 24 mg or about 24 mg is administered on day 1.

In some embodiments, the bispecific antibody is administered (e.g., subcutaneously) in 28-day cycles, wherein
a) in cycle 1, a priming dose in the range of 0.05 and 0.35 is administered on day 1, an intermediate dose in the range of 0.6 and 1.2 mg on day 8, and a full dose of 24 mg on days 15 and 22;
b) in cycles 2-3, a full dose of 24 mg is administered on days 1, 8, 15, and 22;
c) in cycles 4-9, a full dose of 24 mg is administered on days 1 and 15; and
d) in cycle 10 and subsequent cycles, a full dose of 24 mg is administered on day 1.

In some embodiments, the bispecific antibody is administered (e.g., subcutaneously) in 28-day cycles, wherein
a) in cycle 1, a priming dose of 160 µg is administered on day 1, an intermediate dose of 800 µg on day 8, and a full dose of 24 mg or about 24 mg on days 15 and 22;
b) in cycles 2-3, a full dose of 24 mg or about 24 mg is administered on days 1, 8, 15, and 22;
c) in cycles 4-9, a full dose of 24 mg or about 24 mg is administered on days 1 and 15; and
d) in cycle 10 and subsequent cycles, a full dose of 24 mg or about 24 mg is administered on day 1.

In some embodiments, the bispecific antibody is administered (e.g., subcutaneously) in 28-day cycles, wherein
  a) in cycle 1, a priming dose is administered on day 1, an intermediate dose on day 8, and a full dose of 48 mg or about 48 mg on days 15 and 22;
  b) in cycles 2-3, a full dose of 48 mg or about 48 mg is administered on days 1, 8, 15, and 22;
  c) in cycles 4-9, a full dose of 48 mg or about 48 mg is administered on days 1 and 15; and
  d) in cycle 10 and subsequent cycles, a full dose of 48 mg or about 48 mg is administered on day 1.

In some embodiments, the bispecific antibody is administered (e.g., subcutaneously) in 28-day cycles, wherein
  a) in cycle 1, a priming dose in the range of 0.05-0.35 is administered on day 1, an intermediate dose in the range of 0.6-1.2 mg on day 8, and a full dose of 48 mg on days 15 and 22;
  b) in cycles 2-3, a full dose of 48 mg is administered on days 1, 8, 15, and 22;
  c) in cycles 4-9, a full dose of 48 mg is administered on days 1 and 15; and
  d) in cycle 10 and subsequent cycles, a full dose of 48 mg is administered on day 1.

In some embodiments, the bispecific antibody is administered (e.g., subcutaneously) in 28-day cycles, wherein
  a) in cycle 1, a priming dose of 160 µg is administered on day 1, an intermediate dose of 800 µg on day 8, and a full dose of 48 mg or about 48 mg on days 15 and 22;
  b) in cycles 2-3, a full dose of 48 mg or about 48 mg is administered on days 1, 8, 15, and 22;
  c) in cycles 4-9, a full dose of 48 mg or about 48 mg is administered on days 1 and 15; and
  d) in cycle 10 and subsequent cycles, a full dose of 48 mg or about 48 mg is administered on day 1.

In some embodiments, the bispecific antibody is administered (e.g., subcutaneously) in 28-day cycles, wherein
  a) in cycle 1, a priming dose is administered on day 1, an intermediate dose on day 8, and a full dose of 60 mg or about 60 mg on days 15 and 22;
  b) in cycles 2-3, a full dose of 60 mg or about 60 mg is administered on days 1, 8, 15, and 22;
  c) in cycles 4-9, a full dose of 60 mg or about 60 mg is administered on days 1 and 15; and
  d) in cycle 10 and subsequent cycles, a full dose of 60 mg or about 60 mg is administered on day 1.

In some embodiments, the bispecific antibody is administered (e.g., subcutaneously) in 28-day cycles, wherein
  a) in cycle 1, a priming dose in the range of 0.05-0.35 is administered on day 1, an intermediate dose in the range of 0.6-1.2 mg on day 8, and a full dose of 60 mg on days 15 and 22;
  b) in cycles 2-3, a full dose of 60 mg is administered on days 1, 8, 15, and 22;
  c) in cycles 4-9, a full dose of 60 mg is administered on days 1 and 15; and
  d) in cycle 10 and subsequent cycles, a full dose of 60 mg is administered on day 1.

In some embodiments, the bispecific antibody is administered (e.g., subcutaneously) in 28-day cycles, wherein
  a) in cycle 1, a priming dose of 160 µg is administered on day 1, an intermediate dose of 800 µg on day 8, and a full dose of 60 mg or about 60 mg on days 15 and 22;
  b) in cycles 2-3, a full dose of 60 mg or about 60 mg is administered on days 1, 8, 15, and 22;
  c) in cycles 4-9, a full dose of 60 mg or about 60 mg is administered on days 1 and 15; and
  d) in cycle 10 and subsequent cycles, a full dose of 60 mg or about 60 mg is administered on day 1.

In some embodiments, the bispecific antibody is epcoritamab, which is administered subcutaneously in 28-day cycles, wherein
  a) in cycle 1, a priming dose is administered on day 1, an intermediate dose on day 8, and a full dose of 12-60 mg on days 15 and 22;
  b) in cycles 2-3, a full dose of 12-60 mg is administered on days 1, 8, 15, and 22;
  c) in cycles 4-9, a full dose of 12-60 mg is administered on days 1 and 15; and
  d) in cycle 10 and subsequent cycles, a full dose of 12-60 mg is administered on day 1.

In some embodiments, the bispecific antibody is epcoritamab, which is administered (e.g., subcutaneously) in 28-day cycles, wherein
  a) in cycle 1, a priming dose in the range of 0.05-0.35 is administered on day 1, an intermediate dose in the range of 0.6-1.2 mg on day 8, and a full dose of 12-60 mg on days 15 and 22;
  b) in cycles 2-3, a full dose of 12-60 mg is administered on days 1, 8, 15, and 22;
  c) in cycles 4-9, a full dose of 12-60 mg is administered on days 1 and 15; and
  d) in cycle 10 and subsequent cycles, a full dose of 12-60 mg is administered on day 1.

In some embodiments, the bispecific antibody is epcoritamab, which is administered subcutaneously in 28-day cycles, wherein
  a) in cycle 1, a priming dose of 160 µg is administered on day 1, an intermediate dose of 800 µg on day 8, and a full dose of 12-60 mg on days 15 and 22;
  b) in cycles 2-3, a full dose of 12-60 mg is administered on days 1, 8, 15, and 22;
  c) in cycles 4-9, a full dose of 12-60 mg is administered on days 1 and 15; and
  d) in cycle 10 and subsequent cycles, a full dose of 12-60 mg is administered on day 1.

In some embodiments, the bispecific antibody is epcoritamab, which is administered subcutaneously in 28-day cycles, wherein
  a) in cycle 1, a priming dose is administered on day 1, an intermediate dose on day 8, and a full dose of 12 mg or about 12 mg on days 15 and 22;
  b) in cycles 2-3, a full dose of 12 mg or about 12 mg is administered on days 1, 8, 15, and 22;
  c) in cycles 4-9, a full dose of 12 mg or about 12 mg is administered on days 1 and 15; and
  d) in cycle 10 and subsequent cycles, a full dose of 12 mg or about 12 mg is administered on day 1.

In some embodiments, the bispecific antibody is epcoritamab, which is administered (e.g., subcutaneously) in 28-day cycles, wherein
  a) in cycle 1, a priming dose in the range of 0.05-0.35 is administered on day 1, an intermediate dose in the range of 0.6-1.2 mg on day 8, and a full dose of 12 mg on days 15 and 22;
  b) in cycles 2-3, a full dose of 12 mg is administered on days 1, 8, 15, and 22;
  c) in cycles 4-9, a full dose of 12 mg is administered on days 1 and 15; and
  d) in cycle 10 and subsequent cycles, a full dose of 12 mg is administered on day 1.

In some embodiments, the bispecific antibody is epcoritamab, which is administered subcutaneously in 28-day cycles, wherein a) in cycle 1, a priming dose of 160 µg is administered on day 1, an intermediate dose of 800 µg on day 8, and a full dose of 12 mg or about 12 mg on days 15 and 22;
b) in cycles 2-3, a full dose of 12 mg or about 12 mg is administered on days 1, 8, 15, and 22;
c) in cycles 4-9, a full dose of 12 mg or about 12 mg is administered on days 1 and 15; and
d) in cycle 10 and subsequent cycles, a full dose of 12 mg or about 12 mg is administered on day 1.

In some embodiments, the bispecific antibody is epcoritamab, which is administered subcutaneously in 28-day cycles, wherein
a) in cycle 1, a priming dose is administered on day 1, an intermediate dose on day 8, and a full dose of 24 mg or about 24 mg on days 15 and 22;
b) in cycles 2-3, a full dose of 24 mg or about 24 mg is administered on days 1, 8, 15, and 22;
c) in cycles 4-9, a full dose of 24 mg or about 24 mg is administered on days 1 and 15; and
d) in cycle 10 and subsequent cycles, a full dose of 24 mg or about 24 mg is administered on day 1.

In some embodiments, the bispecific antibody is epcoritamab, which is administered (e.g., subcutaneously) in 28-day cycles, wherein
a) in cycle 1, a priming dose in the range of 0.05-0.35 is administered on day 1, an intermediate dose in the range of 0.6-1.2 mg on day 8, and a full dose of 24 mg on days 15 and 22;
b) in cycles 2-3, a full dose of 24 mg is administered on days 1, 8, 15, and 22;
c) in cycles 4-9, a full dose of 24 mg is administered on days 1 and 15; and
d) in cycle 10 and subsequent cycles, a full dose of 24 mg is administered on day 1.

In some embodiments, the bispecific antibody is epcoritamab, which is administered subcutaneously in 28-day cycles, wherein
a) in cycle 1, a priming dose of 160 µg is administered on day 1, an intermediate dose of 800 µg on day 8, and a full dose of 24 mg or about 24 mg on days 15 and 22;
b) in cycles 2-3, a full dose of 24 mg or about 24 mg is administered on days 1, 8, 15, and 22;
c) in cycles 4-9, a full dose of 24 mg or about 24 mg is administered on days 1 and 15; and
d) in cycle 10 and subsequent cycles, a full dose of 24 mg or about 24 mg is administered on day 1.

In some embodiments, the bispecific antibody is epcoritamab, which is administered subcutaneously in 28-day cycles, wherein
a) in cycle 1, a priming dose is administered on day 1, an intermediate dose on day 8, and a full dose of 48 mg or about 48 mg on days 15 and 22;
b) in cycles 2-3, a full dose of 48 mg or about 48 mg is administered on days 1, 8, 15, and 22;
c) in cycles 4-9, a full dose of 48 mg or about 48 mg is administered on days 1 and 15; and
d) in cycle 10 and subsequent cycles, a full dose of 48 mg or about 48 mg is administered on day 1.

In some embodiments, the bispecific antibody is epcoritamab, which is administered (e.g., subcutaneously) in 28-day cycles, wherein
a) in cycle 1, a priming dose in the range of 0.05-0.35 is administered on day 1, an intermediate dose in the range of 0.6-1.2 mg on day 8, and a full dose of 48 mg on days 15 and 22;
b) in cycles 2-3, a full dose of 48 mg is administered on days 1, 8, 15, and 22;
c) in cycles 4-9, a full dose of 48 mg is administered on days 1 and 15; and
d) in cycle 10 and subsequent cycles, a full dose of 48 mg is administered on day 1.

In some embodiments, the bispecific antibody is epcoritamab, which is administered subcutaneously in 28-day cycles, wherein
a) in cycle 1, a priming dose of 160 µg is administered on day 1, an intermediate dose of 800 µg on day 8, and a full dose of 48 mg or about 48 mg on days 15 and 22;
b) in cycles 2-3, a full dose of 48 mg or about 48 mg is administered on days 1, 8, 15, and 22;
c) in cycles 4-9, a full dose of 48 mg or about 48 mg is administered on days 1 and 15; and
d) in cycle 10 and subsequent cycles, a full dose of 48 mg or about 48 mg is administered on day 1.

In some embodiments, the bispecific antibody is epcoritamab, which is administered subcutaneously in 28-day cycles, wherein
a) in cycle 1, a priming dose is administered on day 1, an intermediate dose on day 8, and a full dose of 60 mg or about 60 mg on days 15 and 22;
b) in cycles 2-3, a full dose of 60 mg or about 60 mg is administered on days 1, 8, 15, and 22;
c) in cycles 4-9, a full dose of 60 mg or about 60 mg is administered on days 1 and 15; and
d) in cycle 10 and subsequent cycles, a full dose of 60 mg or about 60 mg is administered on day 1.

In some embodiments, the bispecific antibody is epcoritamab, which is administered (e.g., subcutaneously) in 28-day cycles, wherein
a) in cycle 1, a priming dose in the range of 0.05-0.35 is administered on day 1, an intermediate dose in the range of 0.6-1.2 mg on day 8, and a full dose of 60 mg on days 15 and 22;
b) in cycles 2-3, a full dose of 60 mg is administered on days 1, 8, 15, and 22;
c) in cycles 4-9, a full dose of 60 mg is administered on days 1 and 15; and
d) in cycle 10 and subsequent cycles, a full dose of 60 mg is administered on day 1.

In some embodiments, the bispecific antibody is epcoritamab, which is administered subcutaneously in 28-day cycles, wherein
a) in cycle 1, a priming dose of 160 µg is administered on day 1, an intermediate dose of 800 µg on day 8, and a full dose of 60 mg or about 60 mg on days 15 and 22;
b) in cycles 2-3, a full dose of 60 mg or about 60 mg is administered on days 1, 8, 15, and 22;
c) in cycles 4-9, a full dose of 60 mg or about 60 mg is administered on days 1 and 15; and
d) in cycle 10 and subsequent cycles, a full dose of 60 mg or about 60 mg is administered on day 1.

In one embodiment, on days 1 and 8 of the first cycle, a priming dose of 80 µg and an intermediate dose of 800 µg, respectively, is selected. In some embodiments, on days 1 and 8 of the first cycle, a priming dose of 80 µg and an intermediate dose of 1200 µg, respectively, is selected. In some embodiments, on days 1 and 8 of the first cycle, a priming dose of 80 µg and an intermediate dose of 1600 µg, respectively, is selected. In some embodiments, on days 1 and 8 of the first cycle, a priming dose of 160 µg and an intermediate dose of 1200 µg, respectively, is selected. In some embodiments, on days 1 and 8 of the first cycle, a priming dose of 160 µg and an intermediate dose of 1600 µg, respectively, is selected.

In one embodiment, the human subject has active CLL disease that needs treatment, meeting at least one of the following criteria: (1) evidence of progressive marrow failure as manifested by the development of, or worsening of, anemia and/or thrombocytopenia; (2) Massive (i.e., ≥6 cm below the left costal margin) or progressive or symptomatic splenomegaly; (3) Massive nodes (i.e., ≥10 cm in longest diameter) or progressive or symptomatic lymphadenopathy; (4) Progressive lymphocytosis with an increase of ≥50% over a 2-month period, or lymphocyte doubling time (LDT) <6 months; (5) Autoimmune complications including anemia or thrombocytopenia poorly responsive to corticosteroids; (6) Symptomatic or functional extra nodal involvement (e.g., skin, kidney, lung, spine); and/or (7) Disease-related symptoms as defined by any of the following: unintentional weight loss ≥10% within the previous 6 months, significant fatigue, fevers ≥38.0° C. (100.5° F.) for 2 or more weeks without evidence of infection, and night sweats for ≥1 month without evidence of infection. In some embodiments, the CLL disease is relapsed and/or refractory CLL. In some embodiments, the CLL is refractory to a BTK inhibitor. In some embodiments, the CLL relapsed during treatment with a BTK inhibitor.

In some embodiments, the human subject has received at least one line of treatment prior to being treated with the methods described herein. For instance, in one embodiment, the subject has received one prior line of treatment. In some embodiments, the subject has received two prior lines of treatment. In some embodiments, the subject has received two prior lines of systemic antineoplastic therapy. In some embodiments, the subject has received two prior lines of systemic antineoplastic therapy, wherein at least one of the at least two prior antineoplastic therapy comprises treatment with (or intolerance of) a BTK inhibitor (e.g., ibrutinib). In some embodiments, the subject has refractory and/or relapsed CLL after receiving the two prior antineoplastic therapies. Relapse may be defined as evidence of disease progression in a subject who has previously achieved a CR or PR for at least 6 months. Refractory disease may be defined as treatment failure (not achieving a CR or PR) or as progression within 6 months from the last dose of therapy. In some embodiments, the subject has received three prior lines of treatment. In some embodiments, the subject has received more than three prior lines of treatment. In some embodiments, the subject has received one, two, three, or more prior lines of treatment. In some embodiments, the subject has received at least two prior lines of treatment. In one embodiment, a prior line of treatment comprises systemic antineoplastic therapy. In one embodiment, the systemic antineoplastic therapy comprises treatment with a BTK inhibitor, e.g., ibrutinib. In some embodiments, the subject is intolerant to a BTK inhibitor, e.g., ibrutinib. In other embodiments, a prior line of therapy comprises treatment with a BCL2 inhibitor, e.g. venetoclax. In still further embodiments, a prior line of therapy comprises a treatment with a combination of a BTK inhibitor and a BCL2 inhibitor (e.g., ibrutinib and venetoclax).

In some embodiments, the human subject has measurable disease meeting at least one of (a) ≥5×10$^9$/L (5,000/µL) B lymphocytes in peripheral blood and (b) presence of measurable lymphadenopathy and/or organomegaly.

In some embodiments, the human subject has an ECOG performance status score of 0 or 1. Information regarding ECOG performance status scores can be found in, e.g., Oken et al, *Am J Clin Oncol* 1982 December; 5(6):649-55).

In some embodiments, the human subject has acceptable laboratory parameters for (1) creatine clearance or serum creatine (>45 mL/min using Cockcroft-Gault formula or serum creatinine ≤1.5 times the upper limit of normal (×ULN)), (2) serum alanine transaminase (≤2.5×ULN), (3) serum aspartate transaminase (≤2.5×ULN), (4) bilirubin (≤1.5×ULN unless due to Gilbert syndrome), (5) hemoglobin (≥9.0 g/dL unless anemia is due to marrow involvement of CLL), (6) absolute neutrophil count (≥1.0×10$^9$/L (1000/µL) unless neutropenia is due to bone marrow involvement of CLL), platelet count (≥30×10$^9$/L (30,000/µL)), and coagulation status (PT/INR/aPTT≤1.5×ULN).

A human subject receiving a treatment described herein may be a patient having one or more of the inclusion criteria set forth in Example 2, or not having one or more of the exclusion criteria set forth in Example 2.

Human subjects with CLL are classified as having a CD20-positive cancer. Thus, prior cancer treatments such human subjects may have received include anti-CD20 monoclonal antibodies (e.g., rituximab). During such treatments, or any other treatments, the CLL may be refractory or have relapsed to said treatment. Accordingly, in one embodiment, the subject has received prior to treatment with the bispecific antibody a treatment with an anti-CD20 monoclonal antibody, such as rituximab or obinutuzumab. In some embodiments, during said prior treatment with the anti-CD20 antibody or combinations of anti-CD20 monoclonal antibody with one therapeutic agent, e.g., venetoclax (a Bcl2 inhibitor), the CLL relapsed or was refractory to treatment.

The methods described herein are advantageous for treating CLL, such as refractory or recurrent CLL. The treatment is maintained continuously using, e.g., the treatment regimens described above. However, treatment may be terminated when progressive disease develops or unacceptable toxicity occurs.

The response of subjects with CLL to the methods described herein may be assessed according to the iwCLL response criteria, as shown in Table 2 (source: Hallek et al., *Lancet* 2018; 391:1524-1537).

TABLE 2

| | | International Workshop on Chronic Lymphocytic Leukemia Response Criteria | | | |
|---|---|---|---|---|---|
| Group | Parameter | CR | PR | PD | SD |
| | | Group A: Assessment of lymphoid tumor load and constitutional symptoms | | | |
| | Lymph nodes | None ≥1.5 cm | Decrease ≥50% (from baseline)[1] | Increase ≥50% from baseline or from response | Change of −49% to +49% |
| | Liver and/or spleen size[2] | Spleen size <13 cm; liver size normal | Decrease ≥50% from baseline | Increase ≥50% from baseline or from response | Change of −49% to +49% |

TABLE 2-continued

International Workshop on Chronic Lymphocytic Leukemia Response Criteria

| Group | Parameter | CR | PR | PD | SD |
|---|---|---|---|---|---|
| | Constitutional symptoms | None | Any | Any | Any |
| | Circulating lymphocyte count | None | Decrease ≥50% from baseline | Increase ≥50% from baseline or from response | Change of −49% to +49% |
| Group B: Assessment of hematopoietic system | | | | | |
| | Platelet count | ≥100 × 10$^9$/L (≥100,000 μL) | ≥100 × 10$^9$/L (≥100,000 μL) or increase ≥50% over baseline | Decrease ≥50% from baseline secondary to CLL | Change of −49% to +49% |
| | Hemoglobin | ≥11.0 g/dL (untransfused and without erythropoietin) | ≥11.0 g/dL or increase of ≥50% over baseline | Decrease of ≥2.0 g/dL from baseline, secondary to CLL | Increase <11.0 g/dL or <50% over baseline or decrease <2.0 g/dL |
| | Bone marrow | Normocellular, no CLL cells, no B-lymphoid nodules | Presence of CLL cells or B-lymphoid nodules, or not done | Increase of CLL cells by ≥50% on successive biopsies | No change in marrow infiltration |

Abbreviations:
CLL = chronic lymphocytic leukemia;
CR = complete response;
PD = progressive disease;
PR = partial response;
SD = stable disease.
Definitions:
CR, complete remission (all the criteria have to be met);
PD, progressive disease (at least 1 of the criteria of group A or group B has to be met);
PR, partial remission (for a PR, at least 2 of the parameters of group A and 1 parameter of group B need to improve if previously abnormal; if only 1 parameter of both groups A and B is abnormal before therapy, only 1 needs to improve);
SD, stable disease (all of the criteria have to be met; constitutional symptoms alone do not define PD).
[1]Sum of the products of 6 or fewer lymph nodes (as evaluated by CT scans and physical examination in clinical trials or by physical examination in general practice).
[2]Spleen size is considered normal if <13 cm. There is not firmly established international consensus on the size of a normal liver; therefore, liver size should be evaluated by imaging and manual palpation and recorded in eCRF.

Subjects treated according to the methods described herein preferably experience improvement in at least one sign of CLL. In one embodiment, improvement is measured by a reduction in the number of circulating lymphocytes. In some embodiments, improvement is measured by a reduction in the quantity and/or size of measurable tumor lesions. In some embodiments, lesions can be measured on CT or MRI films. In some embodiments, cytology or histology can be used to evaluate responsiveness to a therapy. In some embodiments, bone marrow aspirate and bone marrow biopsy can be used to evaluate response to therapy.

In one embodiment, the subject treated exhibits a complete response (CR), a partial response (PR), or stable disease (SD), as defined by iwCLL response criteria (see, e.g., Table 2). In some embodiments, the methods described herein produce at least one therapeutic effect chosen from prolonged survival, such as progression-free survival or overall survival, optionally compared to another therapy or placebo. In some embodiments, the subjects are treated with the methods described herein until disease progression (PD) or unacceptable toxicity.

Cytokine release syndrome (CRS) can occur when methods are used in human subjects that utilize immune cell- and bispecific antibody-based approaches that function by activation of immune effector cell, such as by engaging CD3 (Lee et al., *Biol Blood Marrow Transplant* 2019; 25:625-38, which is incorporated herein by reference). Hence, in some embodiments, CRS mitigation is performed together with the methods described herein. As part of CRS mitigation, the selection of a priming dose and/or intermediate dose is performed prior to administering the full dose (e.g., 12-60 mg), as described herein. CRS can be classified in accordance with standard practice (e.g. as outlined in Lee et al., *Biol Blood Marrow Transplant.* 2019 April; 25(4):625-638, which is incorporated herein by reference). CRS may include excessive release of cytokines, for example of proinflammatory cytokines, e.g., IL-6, TNF-alpha or IL-8, that may result in adverse effects like fever, nausea, vomiting and chills. Thus, despite the unique anti-tumor activity of bispecific antibodies such as epcoritamab, their immunological mode of action may trigger unwanted "side" effects, i.e., the induction of unwanted inflammatory reactions. Hence, patients may be further subjected to a concomitant treatment, prophylaxis, and/or premedication with, e.g., analgesics, antipyretics, and/or anti-inflammatory drugs to mitigate possible CRS symptoms.

Accordingly, in one embodiment, human subjects in the methods described herein are treated with prophylaxis for CRS. In preferred embodiments, the prophylaxis comprises the administration of a corticosteroid to the subject. In one embodiment, the prophylaxis (e.g. corticosteroid) is administered on the same day as the bispecific antibody. The prophylaxis (e.g. corticosteroid) can also be administered on the subsequent days as well. In some embodiments, the prophylaxix (e.g. corticosteroid) is further administered on subsequent days 2, 3, and 4. It is understood that days 2, 3 and 4 when relating to further medication, such as prophylaxis, is relative to the administration of the bispecific antibody which is administered on day 1. For example, when in a cycle the antibody is administered on day 15, and prophylaxis is also administered, the prophylaxis corresponding to days 2, 3 and 4 are days 16, 17, and 18 of the cycle. In some embodiments, the prophylaxis is administered on the day when the bispecific antibody is administered and on subsequent days 2-4. When said prophylaxis is administered on the same day as the bispecific antibody, the prophylaxis is preferably administered 30-120 minutes prior to said administration of the bispecific antibody. An exemplary corticosteroid suitable for use in the methods and uses described herein is prednisolone. In some embodiments, the corticosteroid is prednisolone. In some embodiments, prednisolone is administered at an intravenous dose of 100 mg, or an equivalent thereof, including an oral dose. Exemplary corticosteroid equivalents of prednisolone, along with dosage equivalents, which can be used for CRS prophylaxis are shown in Table 6.

Furthermore, in some embodiments, human subjects in the methods described herein are treated with premedication to reduce reactions to injections. In one embodiment, the premedication includes the administration of antihistamines. In some embodiments, the premedication includes the administration of antipyretics. In a further embodiment, the premedication includes systemic administration of antihistamines and antipyretics.

An exemplary antihistamine suitable for use in premedication is diphenhydramine. In some embodiments, the antihistamine is diphenhydramine. In one embodiment, diphenhydramine is administered at an intravenous or oral dose 50 mg, or an equivalent thereof. An exemplary antipyretic suitable for use in premedication is acetaminophen. In some embodiments, the antipyretic is acetaminophen. In one embodiment, acetaminophen is administered at an oral dose of 560-1000 mg, such as 650-1000 mg, or equivalent thereof. In some embodiments, the premedication is administered on the same day as the bispecific antibody. In some embodiments, the premedication is administered on the same day as the bispecific antibody prior to the injection with the bispecific antibody, e.g., 30-120 minutes prior to administration of the bispecific antibody.

Premedication and/or prophylaxis can be administered at least in the initial phase of the treatment. In some embodiments, premedication and/or prophylaxis is administered during the first four administrations of the bispecific antibody. For example, the premedication and/or prophylaxis can be administered as described herein, during the first 28 day cycle of the bispecific antibody administration. In some embodiments, the premedication is administered during cycle 1. In some embodiments, the prophylaxis is administered during cycle 1.

Usually, risk of reactions during the initial treatment subsides after a few administrations, e.g., after the first four administrations (first cycle). Hence, and when the human subject does not experience CRS, prophylaxis for CRS may be stopped. However, when the human subject experiences a CRS greater than grade 1, CRS prophylaxis may continue. Likewise, premedication may also optionally continue. CRS grading can be performed as described in Tables 7 and 8.

In a further embodiment, in the methods described herein, the prophylaxis is administered during the second 28-day cycle i.e cycle 2, when the human subject experiences CRS greater than grade 1 after the fourth i.e. last administration of the bispecific antibody in cycle 1. Furthermore, the prophylaxis can be continued during a subsequent cycle, when in the last administration of the bispecific antibody of the previous cycle, the human subject experiences CRS greater than grade 1. Any premedication may be optionally administered during the second cycle. In some embodiments, the premedication is administered during cycle 2. Further premedication may be optionally administered during subsequent cycles as well. In some embodiments, the premedication is administered during subsequent cycles (after cycle 2).

In one embodiment, premedication and prophylaxis for CRS is administered, wherein the premedication comprises an antihistamine such as diphenhydramine (e.g., at an intravenous or oral dose 50 mg, or an equivalent thereof) and the prophylaxis comprises an antipyretic such as acetaminophen (e.g., at an oral dose of 650-1000 mg, or an equivalent thereof), and a corticosteroid such as prednisolone (e.g., at an intravenous dose of 100 mg, or an equivalent thereof). In some embodiments, the premedication and prophylaxis is administered 30-120 minutes prior to administration of the bispecific antibody. On subsequent days 2, 3, and optionally day 4, further prophylaxis is administered comprising the systemic administration of a corticosteroid such as prednisolone (e.g., at an intravenous dose of 100 mg, or an equivalent thereof). In some embodiments, the premedication and prophylaxis schedule preferably is administered during the first four administrations of the bispecific antibody, e.g., during the first 28-day cycle of bispecific antibody administration described herein. Furthermore, subsequent cycles, in case of, e.g., CRS greater than grade 1 occurring during the last administration of the prior cycle, can include the same administration schedule, wherein the premedication as part of the administration schedule is optional.

During the treatment of a human subject with CLL using the doses and treatment regimens described herein, CRS can be well managed while at the same time effectively controlling and/or treating CLL. As described in the Examples, subjects treated with the methods described herein may experience manageable CRS. In some cases, subjects receiving the treatment described herein may develop CRS of grade 1 as defined in accordance with standard practice. In other cases, subjects may develop manageable CRS of grade 2 as defined in accordance with standard practice. Hence, subjects receiving the treatments described herein may have manageable CRS of grade 1 or grade 2 during as defined in accordance with standard practice. In accordance with standard classification for CRS, a grade 1 CRS includes a fever to at least 38° C., no hypotension, no hypoxia, and a grade 2 CRS includes a fever to at least 38° C. plus hypotension, not requiring vasopressors and/or hypoxia requiring oxygen by low flow nasal cannula or blow by. Such manageable CRS can occur during cycle 1. Human subjects receiving the treatments described herein may also have CRS greater than grade 2 during the treatments as defined in accordance with standard practice. Hence, human subjects receiving the treatments described herein may also have CRS of grade 3 during said treatments as defined in accordance with standard practice. Such manageable CRS may further occur during cycle 1 and subsequent cycles.

Human subjects treated according to the methods described herein may also experience pyrexia, fatigue, and injection site reactions. They may also experience neurotoxicity, partial seizures, agraphia related to CRS, or confusional state related to CRS.

As mentioned above, subjects may develop CRS during treatment with the methods described herein, despite having received CRS prophylaxis. CRS grading criteria are described in Tables 7 and 8.

In one embodiment, subject is administered antibiotics if the subject develops Grade 1 CRS i.e. subjects who develop Grade 1 CRS are treated with antibiotics if they present with infection. In some embodiments, the antibiotics are continued until neutropenia, if present, resolves. In some embodiments, subjects with Grade 1 CRS who exhibit constitutional symptoms are treated with NSAIDs.

In one embodiments, subjects who develop Grade 2 CRS are treated with intravenous fluid boluses and/or supplemental oxygen. In some embodiments, subjects who develop Grade 2 CRS are treated with a vasopressor. In some embodiments, subjects with Grade 2 CRS with comorbidities are treated with tocilizumab (a humanized antibody against IL-6 receptor, commercially available as, e.g., ACTEMRA®) and/or steroids (e.g., dexamethasone or its equivalent of methylprednisolone). In a further embodiment, a subject who presents with concurrent ICANS is administered dexamethasone. In yet a further embodiment, if the subject does not show improvement in CRS symptoms within, e.g., 6 hours, or if the subject starts to deteriorate after initial improvement, then a second dose of tocilizumab is administered together with a dose of corticosteroids. In some embodiments, if the subject is refractory to tocilizumab after three administrations, then additional cytokine therapy, e.g., an anti-IL-6 antibody (e.g., siltuximab) or an IL-1R antagonist (e.g., anakinra) is administered to the subject.

In one embodiment, subjects who develop Grade 3 CRS are treated with vasopressor (e.g., norepinephrine) support and/or supplemental oxygen. In some embodiments, subjects with Grade 3 CRS are treated with tocilizumab, or tocilizumab in combination with steroids (e.g., dexamethasone or its equivalent of methylprednisolone). In some embodiments, a subject who presents with concurrent ICANS is administered dexamethasone. In a further embodiment, if the subject is refractory to tocilizumab after three administrations, then additional cytokine therapy, e.g., an anti-IL-6 antibody (e.g., siltuximab) or an IL-1R antagonist (e.g., anakinra) is administered to the subject.

In one embodiment, subjects who develop Grade 4 CRS are treated with vasopressor support and/or supplemental oxygen (e.g., via positive pressure ventilation, such as CPAP, BiPAP, intubation, or mechanical ventilation). In some embodiments, the subject is administered at least two vasopressors if the subject develops Grade 4 CRS. In some embodiments, the subject is further administered a steroid i.e. the subject is administered tocilizumab and a steroid. In some embodiments, the steroid is dexamethasone. In some embodiments, the steroid is methylprednisolone. In a further embodiment, a subject who presents with concurrent ICANS is administered dexamethasone. In a further embodiment, if the subject is refractory to tocilizumab after three administrations, then additional cytokine therapy, e.g., an anti-IL-6 antibody (e.g., siltuximab) or an IL-1R antagonist (e.g., anakinra) is administered to the subject. In some embodiments, administration of tocilizumab is switched to administration of an anti-IL-6 antibody (e.g., siltuximab) if the subject is refractory to tocilizumab. In some embodiments, tocilizumab is switched to an IL-1R antagonist (e.g., anakinra) if the subject is refractory to tocilizumab.

In some embodiments, the human subject receives prophylactic treatment for tumor lysis syndrome (TLS) i.e. the subject is treated with prophylaxis for tumor lysis syndrome (TLS). Classification and grading of tumor lysis syndrome can be performed using methods known in the art, for example, as described in Howard et al. *N Engl J Med* 2011; 364:1844-54, and Coiffier et al., *J Clin Oncol* 2008; 26:2767-78. In some embodiments, prophylactic treatment of TLS comprises administering one or more uric acid reducing agents prior to administering the bispecific antibody i.e. the prophylaxis for TLS comprises administering one or more uric acid reducing agents prior to administration of the bispecific antibody. Exemplary uric acid reducing agents include allopurinol and rasburicase. Accordingly, in one embodiment, the prophylactic treatment of TLS comprises administering allopurinol and/or rasburicase. In some embodiments, the prophylactic treatment of TLS comprises administering allopurinol and/or rasburicase prior to administering the bispecific antibody. In one embodiment, allopurinol is administered 72 hours prior to the bispecific antibody. In some embodiments, rasburicase is initiated after administering allopurinol but prior to administering the bispecific antibody. Reassessment of the subject's TLS risk category can be performed prior to subsequent doses of the bispecific antibody. A subject is considered to be at low risk of TLS if all measurable lymph nodes have a largest diameter <5 cm and ALC<$25 \times 10^9$/L. A subject is considered to be at medium risk of TLS if any measurable lymph node has a largest diameter ≥5 cm but <10 cm or ALC≥$25 \times 10^9$/L. A subject is considered to be at high risk of TLS if (a) any measurable lymph node has a largest diameter ≥10 cm, or (b) ALC≥$25 \times 10^9$/L and any measurable lymph node has a largest diameter ≥5 cm but <10 cm. Subjects with a lymphocyte count >$100 \times 10^9$/L are considered as high risk. In some embodiments, when the subject shows signs of TLS, supportive therapy, such as rasburicase and/or allopurinol, may be used.

In one embodiment, the bispecific antibody used in the methods described herein is administered subcutaneously, and thus is formulated in a pharmaceutical composition such that it is compatible with subcutaneous (s.c.) administration, i.e., having a formulation and/or concentration that allows pharmaceutical acceptable s.c. administration at the doses described herein. In some embodiments, subcutaneous administration is carried out by injection. For example, formulations for DuoBody-CD3xCD20 that are compatible with subcutaneous formulation and can be used in the methods described herein have been described previously (see, e.g., WO2019155008, which is incorporated herein by reference). In some embodiments, the bispecific antibody may be formulated using sodium acetate trihydrate, acetic acid, sodium hydroxide, sorbitol, polysorbate 80, and water for injection, and have a pH of 5.5 or about 5.5. In some embodiments, the bispecific antibody is provided as a 5 mg/mL or 60 mg/mL concentrate. In other embodiments, the desired dose of the bispecific antibody is reconstituted to a volume of about 1 mL for subcutaneous injection.

In one embodiment, a suitable pharmaceutical composition for the bispecific antibody can comprise the bispecific antibody, 20-40 mM acetate, 140-160 mM sorbitol, and a surfactant, such as polysorbate 80, and having a pH of 5.3-5.6. In some embodiments, the pharmaceutical formulation may comprise an antibody concentration in the range of 5-100 mg/mL, e.g., 48 or 60 mg/mL of the bispecific antibody, 30 mM acetate, 150 mM sorbitol, 0.04% w/v polysorbate 80, and have a pH of 5.5. Such a formulation may be diluted with, e.g., the formulation buffer to allow proper dosing and subcutaneous administration.

The volume of the pharmaceutical composition is appropriately selected to allow for subcutaneous administration of the antibody. For example, the volume to be administered is in the range of about 0.3 mL to about 3 mL, such as from 0.3 mL to 3 mL. The volume to be administered can be 0.5 mL, 0.8 mL, 1 mL, 1.2 mL, 1.5 ml, 1.7 mL, 2 mL, or 2.5 mL, or about 0.5 mL, about 0.8 mL, about 1 mL, about 1.2 mL, about 1.5 ml, about 1.7 mL, about 2 mL, or about 2.5 mL. Accordingly, in some embodiments, the volume to be administered is 0.5 mL or about 0.5 mL. In some embodiments, the volume to be administered is 0.8 mL or about 0.8 mL. In some embodiments, the volume to be administered is 1 mL or about 1 mL. In some embodiments, the volume to be administered is 1.2 mL or about 1.2 mL. In some embodiments, the volume to be administered is 1.5 mL or about 1.5 mL. In some embodiments, the volume to be administered is 1.7 mL or about 1.7 mL. In some embodiments, the volume to be administered is 2 mL or about 2 mL. In some embodiments, the volume to be administered is 2.5 mL or about 2.5 mL.

The methods (or uses of CD3xCD20 antibodies) described herein are for the treatment of human patients with CLL. It is understood that the methods described herein may be the first, or part of the first, treatment provided to such patients. However, patients may have been subjected to prior treatments for CLL. Prior treatments may include, but are not limited to, one or more of chemotherapy, immunotherapy, and targeted therapy, or combinations thereof. Most commonly, the standard of care comprises treatments with a combination of cytotoxic chemotherapy and anti-CD20 monoclonal antibodies. It is understood that the methods described herein may also be used in combination with other treatments.

In one embodiment, the bispecific antibody used in the methods described herein comprises:

(i) a first binding arm comprising a first antigen-binding region which binds to human CD3ε (epsilon) and comprises a variable heavy chain (VH) region and a variable light chain (VL) region, wherein the VH region comprises the CDR1, CDR2 and CDR3 sequences within the amino acid sequence of SEQ ID NO: 6, and the VL region comprises the CDR1, CDR2 and CDR3 sequences within the amino acid sequence of SEQ ID NO: 7; and (ii) a second binding arm comprising a second antigen-binding region which binds to human CD20 and comprises a VH region and a VL region, wherein the VH region comprises the CDR1, CDR2 and CDR3 sequences within the amino acid sequence of SEQ ID NO: 13, and the VL region comprises the CDR1, CDR2 and CDR3 sequences within the amino acid sequence SEQ ID NO: 14.

CDR1, CDR2 and CDR3 regions can be identified from variable heavy and light chain regions using methods known in the art. The CDR regions from said variable heavy and light chain regions can be annotated according to IMGT (see Lefranc et al., *Nucleic Acids Research* 1999; 27:209-12 and Brochet. *Nucl Acids Res* 2008; 36:W503-8).

In some embodiments, the bispecific antibody comprises:

(i) a first binding arm comprising a first antigen-binding region which binds to human CD3ε (epsilon) and comprises VHCDR1, VHCDR2 and VHCDR3 the amino acid sequences set forth in SEQ ID NOs: 1, 2, and 3, respectively, and VLCDR1, VLCDR2, and VLCDR3 comprising the amino acid sequences set forth in SEQ ID NO: 4, the sequence GTN, and SEQ ID NO: 5, respectively; and (ii) a second binding arm comprising a second antigen-binding region which binds to human CD20 and comprises VHCDR1, VHCDR2, and VHCDR3 comprising the amino acid sequences set forth in SEQ ID NOs: 8, 9, and 10, respectively, and VLCDR1, VLCDR2, and VLCDR3 comprising the amino acid sequences set forth in SEQ ID NO: 11, the sequence DAS, and SEQ ID NO: 12, respectively.

In some embodiments, the bispecific antibody comprises:

(i) a first binding arm comprising a first antigen-binding region which binds to human CD3ε (epsilon) and comprises a VH region comprising the amino acid sequence of SEQ ID NO: 6, and a VL region comprising the amino acid sequence of SEQ ID NO: 7; and (ii) a second binding arm comprising a second antigen-binding region which binds to human CD20 and comprises a VH region comprising the amino acid sequence of SEQ ID NO: 13, and a VL region comprising the amino acid sequence of SEQ ID NO: 14.

In some embodiments, the bispecific antibody is a full-length antibody. In some embodiments, the bispecific antibody comprises an inert Fc region. In one embodiment, the bispecific antibody is a full-length antibody and have an inert Fc region. In some embodiments, the first binding arm for CD3 is derived from a humanized antibody, e.g., from a full-length IgG1,λ (lambda) antibody such as H1L1 described in WO2015001085, which is incorporated herein by reference, and/or the second binding arm for CD20 is derived from a human antibody, e.g., from a full-length IgG1,κ (kappa) antibody such as clone 7D8 as described in WO2004035607, which is incorporated herein by reference. The bispecific antibody may be produced from two half molecule antibodies, wherein each of the two half molecule antibodies comprises, e.g., the respective first and second binding arms set forth in SEQ ID NOs: 24 and 25, and SEQ ID NOs: 26 and 27. The half-antibodies may be produced in CHO cells and the bispecific antibodies generated by, e.g., Fab-arm exchange. In one embodiment, the bispecific antibody is a functional variant of DuoBody-CD3xCD20.

Accordingly, in some embodiments, the bispecific antibody comprises (i) a first binding arm comprising a first antigen-binding region which binds to human CD3ε (epsilon) and comprises a VH region comprising an amino acid sequence which is at least 85%, 90%, 95%, 96%, 97%, 98%, or 99% identical to SEQ ID NO: 6 or a VH region comprising the amino acid sequence of SEQ ID NO: 6, but with 1, 2, or 3 mutations (e.g., amino acid substitutions), and a VL region comprising an amino acid sequence which is at least 85%, 90%, 95%, 96%, 97%, 98%, or 99% identical to SEQ ID NO: 7 or a VL region comprising the amino acid sequence of SEQ ID NO: 7, but with 1, 2, or 3 mutations (e.g., amino acid substitutions); and (ii) a second binding arm comprising a second antigen-binding region which binds to human CD20 and comprises a VH region comprising an amino acid sequence which is at least 85%, 90%, 95%, 98%, or 99% identical to SEQ ID NO: 13 or a VH region comprising the amino acid sequence of SEQ ID NO: 13, but with 1, 2, or 3 mutations (e.g., amino acid substitutions), and a VL region comprising an amino acid sequence which is at least 85%, 90%, 95%, 98%, or 99% identical to SEQ ID NO: 14 or a VL region comprising the amino acid sequence of SEQ ID NO: 14, but with 1, 2, or 3 mutations (e.g., amino acid substitutions).

In one embodiment, the bispecific antibody comprises:

(i) a first binding arm comprising a first antigen-binding region which binds to human CD3ε (epsilon) and comprises a heavy chain comprising the amino acid sequence of SEQ ID NO: 24, and a light chain comprising the amino acid sequence of SEQ ID NO: 25; and (ii) a second binding arm comprising a second antigen-binding region which binds to human CD20 and comprises a VH region comprising the amino acid sequence of SEQ ID NO: 26, and a VL region comprising the amino acid sequence of SEQ ID NO: 27.

In some embodiments, the bispecific antibody comprises (i) a first binding arm comprising a first antigen-binding region which binds to human CD3ε (epsilon) and comprises a heavy chain comprising an amino acid sequence which is at least 85%, 90%, 95%, 98%, or 99% identical to SEQ ID NO: 24 or a heavy chain comprising the amino acid sequence of SEQ ID NO: 24, but with 1, 2, or 3 mutations (e.g., amino acid substitutions), and a light chain comprising an amino acid sequence which is at least 85%, 90%, 95%, 98%, or 99% identical to SEQ ID NO: 25 or a light chain region comprising the amino acid sequence of SEQ ID NO: 25, but with 1, 2, or 3 mutations (e.g., amino acid substitutions); and (ii) a second binding arm comprising a second antigen-binding region which binds to human CD20 and comprises a heavy chain comprising an amino acid sequence which is at least 85%, 90%, 95%, 98%, or 99% identical to SEQ ID NO: 26 or a heavy chain comprising the amino acid sequence of SEQ ID NO: 26, but with 1, 2, or 3 mutations (e.g., amino acid substitutions), and a light chain comprising an amino acid sequence which is at least 85%, 90%, 95%, 98%, or 99% identical to SEQ ID NO: 27 or a light chain region comprising the amino acid sequence of SEQ ID NO: 27, but with 1, 2, or 3 mutations (e.g., amino acid substitutions).

Various constant regions or variants thereof may be used in the bispecific antibody. In one embodiment, the antibody comprises an IgG constant region, such as a human IgG1 constant region, e.g., a human IgG1 constant region as defined in SEQ ID NO: 15, or any other suitable IgG1 allotype. In some embodiments, the bispecific antibody is a full-length antibody with a human IgG1 constant region. In some embodiments, the first binding arm of the bispecific antibody is derived from a humanized antibody, preferably from a full-length IgG1,λ (lambda) antibody. In one embodiment, the first binding arm of the bispecific antibody is derived from a humanized antibody, e.g., from a full-length IgG1) (lambda) antibody, and thus comprises a κ light chain constant region. In some embodiments, the first binding arm comprises a κ light chain constant region as defined in SEQ ID NO: 22. In some embodiments, the second binding arm of the bispecific antibody is derived from a human antibody, preferably from a full-length IgG1,κ (kappa) antibody. In some embodiments the second binding arm of the bispecific antibody is derived from a human antibody, preferably from a full-length IgG1,κ (kappa) antibody, and thus may comprise a κ light chain constant region. In some embodiments, the second binding arm comprises a κ light chain constant region as defined in SEQ ID NO: 23. In a preferred embodiment, the first binding arm comprises a κ light chain constant region as defined in SEQ ID NO: 22 and the second binding arm comprises a κ light chain constant region as defined in SEQ ID NO: 23.

It is understood that the constant region portion of the bispecific antibody may comprise modifications that allow for efficient formation/production of bispecific antibodies and/or provide for an inert Fc region. Such modifications are well known in the art.

Different formats of bispecific antibodies are known in the art (reviewed by Kontermann, Drug Discov Today 2015; 20:838-47; MAbs, 2012; 4:182-97). Thus, the bispecific antibody used in the methods and uses described herein are not limited to any particular bispecific format or method of producing it. For example, bispecific antibodies may include, but are not limited to, bispecific antibodies with complementary CH3 domains to force heterodimerization, Knobs-into-Holes molecules (Genentech, WO9850431), CrossMAbs (Roche, WO2011117329), or electrostatically-matched molecules (Amgen, EP1870459 and WO2009089004; Chugai, US201000155133; Oncomed, WO2010129304).

Preferably, the bispecific antibody comprises an Fc-region comprising a first heavy chain with a first Fc sequence comprising a first CH3 region, and a second heavy chain with a second Fc sequence comprising a second CH3 region, wherein the sequences of the first and second CH3 regions are different and are such that the heterodimeric interaction between said first and second CH3 regions is stronger than each of the homodimeric interactions of said first and second CH3 regions. Further details on these interactions and how they can be achieved are provided in e.g. WO2011131746 and WO2013060867 (Genmab), which are hereby incorporated by reference. In one embodiment, the bispecific antibody comprises in the first heavy chain (i) the amino acid L in the position corresponding to F405 in the human IgG1 heavy chain constant region of SEQ ID NO: 15, and comprises in the second heavy chain the amino acid R in the position corresponding to K409 in the human IgG1 heavy chain constant region of SEQ ID NO: 15, or vice versa.

Bispecific antibodies may comprise modifications in the Fc region to render the Fc region inert, or non-activating. Thus, in the bispecific antibodies disclosed herein, one or both heavy chains may be modified so that the antibody induces Fc-mediated effector function to a lesser extent relative to the bispecific antibody which does not have the modification. Fc-mediated effector function may be measured by determining Fc-mediated CD69 expression on T cells (i.e. CD69 expression as a result of CD3 antibody-mediated, Fcγ receptor-dependent CD3 crosslinking), by binding to Fcγ receptors, by binding to C1q, or by induction of Fc-mediated cross-linking of FcγRs. In particular, the heavy chain constant region sequence may be modified so that Fc-mediated CD69 expression is reduced by at least 50%, at least 60%, at least 70%, at least 80%, at least 90%, at least 99% or 100% when compared to a wild-type (unmodified) antibody, wherein said Fc-mediated CD69 expression is determined in a PBMC-based functional assay, e.g. as described in Example 3 of WO2015001085. Modifications of the heavy and light chain constant region sequences may also result in reduced binding of C1q to said antibody. As compared to an unmodified antibody, the reduction may be by at least 70%, at least 80%, at least 90%, at least 95%, at least 97%, or 100%, and C1q binding may be determined, e.g., by ELISA. Further, the Fc region which may be modified so that the antibody mediates reduced Fc-mediated T-cell proliferation compared to an unmodified antibody by at least 50%, at least 60%, at least 70%, at least 80%, at least 90%, at least 99% or 100%, wherein said T-cell proliferation is measured in a PBMC-based functional assay. Examples of amino acid positions that may be modified, e.g., in an IgG1 isotype antibody, include positions L234 and L235. Thus, in one embodiment, the bispecific antibody may comprises a first heavy chain and a second heavy chain, and wherein in both the first heavy chain and the second heavy chain, the amino acid residues at the positions corresponding to positions L234 and L235 in a human IgG1 heavy chain according to Eu numbering are F and E, respectively. In addition, a D265A amino acid substitution can decrease binding to all Fcγ receptors and prevent ADCC (Shields et al., JBC 2001; 276:6591-604). Therefore, the bispecific antibody may comprise a first heavy chain and a second heavy chain, wherein in both the first heavy chain and the second heavy chain, the amino acid residue at the position corresponding to position D265 in a human IgG1 heavy chain according to Eu numbering is A.

In one embodiment, in the first heavy chain and second heavy chain of the bispecific antibody, the amino acids in the positions corresponding to positions L234, L235, and D265 in a human IgG1 heavy chain, are F, E, and A, respectively.

An antibody having these amino acids at these positions is an example of an antibody having an inert Fc region, or a non-activating Fc region.

In some embodiments, the bispecific antibody comprises a first heavy chain and a second heavy chain, wherein in both the first and second heavy chains, the amino acids in the positions corresponding to positions L234, L235, and D265 in the human IgG1 heavy chain constant region of SEQ ID NO: 15 are F, E, and A, respectively. In some embodiments, the bispecific antibody comprises a first heavy chain and a second heavy chain, wherein in the first heavy chain, the amino acid in the position corresponding to F405 in the human IgG1 heavy chain constant region of SEQ ID NO: 15 is L, and wherein in the second heavy chain, the amino acid in the position corresponding to K409 in the human IgG1 heavy chain constant region of SEQ ID NO: 15 is R, or vice versa. In a preferred embodiment, the bispecific antibody comprises a first heavy chain and a second heavy chain, wherein (i) in both the first and second heavy chains, the amino acids in the positions corresponding to positions L234, L235, and D265 in the human IgG1 heavy chain constant region of SEQ ID NO: 15 are F, E, and A, respectively, and (ii) in the first heavy chain, the amino acid in the position corresponding to F405 in the human IgG1 heavy chain constant region of SEQ ID NO: 15 is L, and wherein in the second heavy chain, the amino acid in the position corresponding to K409 in the human IgG1 heavy chain constant region of SEQ ID NO: 15 is R, or vice versa.

With regard to the bispecific antibodies described herein, those which have the combination of three amino acid substitutions L234F, L235E and D265A and in addition the K409R or the F405L mutation, as described above, may be referred to with the suffix "FEAR" or "FEAL", respectively.

An amino acid sequence of a wild type IgG1 heavy chain constant region may be identified herein as SEQ ID NO: 15. Consistent with the embodiments disclosed above, the bispecific antibody may comprise an IgG1 heavy chain constant region carrying the F405L substitution and may have the amino acid sequence set forth in SEQ ID NO: 17 and/or an IgG1 heavy chain constant region carrying the K409R substitution and may have the amino acid sequence set forth in SEQ ID NO: 18, and have further substitutions that render the Fc region inert or non-activating. Hence, in one embodiment, the bispecific antibody comprises a combination of IgG1 heavy chain constant regions, with the amino acid sequence of one of the IgG1 heavy chain constant regions carrying the L234F, L235E, D265A and F405L substitutions (e.g., as set forth in SEQ ID NO: 19) and the amino acid sequence of the other IgG1 heavy chain constant region carrying the L234F, L235E, D265A and K409R substitutions (e.g., as set forth in SEQ ID NO: 20). Thus, in some embodiments, the bispecific antibody comprises heavy chain constant regions comprising the amino acid sequences of SEQ ID NOs: 19 and 20.

In preferred embodiments, the bispecific antibody used in the methods and uses described herein comprises a first binding arm comprising a heavy chain and a light chain as defined in SEQ ID NOs: 24 and 25, respectively, and a second binding arm comprising a heavy chain and a light chain as defined in SEQ ID NOs: 26 and 27, respectively. Such an antibody can also be referred to herein as DuoBody-CD3xCD20. Also, variants of such antibodies are contemplated use in the methods and uses as described herein. In some embodiment, the bispecific antibody comprising a heavy chain and a light chain consisting of the amino acid sequences set forth in SEQ ID NOs: 24 and 25, respectively, and a heavy chain and a light chain consisting of the amino acid sequences set forth in SEQ ID NOs: 26 and 27, respectively. In some embodiments, the bispecific antibody is epcoritamab (CAS 2134641-34-0), or a biosimilar thereof.

Kits

Also provided herein are kits which include a pharmaceutical composition containing a bispecific antibody which binds to CD3 and CD20 in accordance with the invention, such as DuoBody-CD3xCD20 or epcoritamab, and a pharmaceutically-acceptable carrier, in a therapeutically effective amount adapted for use in the methods described herein. The kits optionally also can include instructions, e.g., comprising administration schedules, to allow a practitioner (e.g., a physician, nurse, or patient) to administer the composition contained therein to administer the composition to a patient with CLL. The kit also can include a syringe.

Optionally, the kits include multiple packages of the single-dose (e.g., a dose between 12-60 mg, such as 12 mg, 24 mg, 36 mg, 48 mg, or 60 mg) pharmaceutical compositions each containing an effective amount of the bispecific antibody for a single administration in accordance with the methods described herein. Instruments or devices necessary for administering the pharmaceutical composition(s) also may be included in the kits. For instance, a kit may provide one or more pre-filled syringes containing an amount of the bispecific antibody.

Further Embodiments

1. A bispecific antibody comprising:
   (i) a first binding arm comprising a first antigen-binding region which binds to human CD3ε (epsilon) and comprises a variable heavy chain (VH) region and a variable light chain (VL) region, wherein the VH region comprises the CDR1, CDR2 and CDR3 sequences that are in the VH region sequence of SEQ ID NO: 6, and the VL region comprises the CDR1, CDR2 and CDR3 sequences that are in the VL region sequence of SEQ ID NO: 7; and
   (ii) a second binding arm comprising a second antigen-binding region which binds to human CD20 and comprises a VH region and a VL region, wherein the VH region comprises the CDR1, CDR2 and CDR3 sequences that are in the VH region sequence of SEQ ID NO: 13, and the VL region comprises the CDR1, CDR2 and CDR3 sequences that are in the VL region sequence of SEQ ID NO: 14;
   for use in the treatment of chronic lymphocytic leukemia (CLL) in a human subject, wherein the treatment comprises administering the bispecific antibody to the human subject at a dose ranging from 12-60 mg in 28-day cycles.

2. The bispecific antibody according to embodiment 1, wherein the bispecific antibody is administered at a dose of 24 mg.

3. The bispecific antibody according to embodiment 1, wherein the bispecific antibody is administered at a dose of 48 mg.

4. The bispecific antibody according to any one of embodiments 1-3, wherein the bispecific antibody is administered once every week (weekly administration).

5. The bispecific antibody according to embodiment 4, wherein the weekly administration is performed for 2.5 28-day cycles.

6. The bispecific antibody according to embodiment 4 or 5, wherein after the weekly administration, the bispecific antibody is administered once every two weeks (biweekly administration).

7. The bispecific antibody according to embodiment 6, wherein the biweekly administration is performed for six 28-day cycles.

8. The bispecific antibody according to embodiment 6 or 7, wherein after the biweekly administration, the bispecific antibody is administered once every four weeks.

9. The bispecific antibody according to any one of embodiments 4-8, wherein prior to administering the first weekly dose of 12-60 mg, a priming dose of the bispecific antibody is administered in cycle 1 of the 28-day cycles.

10. The bispecific antibody according to embodiment 9, wherein the priming dose is administered two weeks prior to administering the first weekly dose of 12-60 mg.

11. The bispecific antibody according to embodiment 9 or 10, wherein the priming dose is in the range of 0.05-0.35 mg.

12. The bispecific antibody according to any one of embodiments 9-11, wherein said priming dose is 0.16 mg or about 0.16 mg.

13. The bispecific antibody according to any one of embodiments 9-12, wherein after administering the priming dose and prior to administering the first weekly dose of 12-60 mg, an intermediate dose of the bispecific antibody is administered.

14. The bispecific antibody according to embodiment 13, wherein the priming dose is administered on day 1 and the intermediate dose is administered on day 8 before the first weekly dose of 12-60 mg on days 15 and 22 of cycle 1.

15. The bispecific antibody according to embodiment 13 or 14, wherein said intermediate dose is in the range of 0.6-1.2 mg.

16. The bispecific antibody according to any one of embodiments 13-15, wherein said intermediate dose is 0.8 mg or about 0.8 mg.

17. The bispecific antibody according to any one of embodiments 13-16, wherein the bispecific antibody is administered in 28-day cycles, wherein:
   a) in cycle 1, a priming dose is administered on day 1, an intermediate dose on day 8, and a full dose of 12-60 mg on days 15 and 22;
   b) in cycles 2-3, a full dose of 12-60 mg is administered on days 1, 8, 15, and 22;
   c) in cycles 4-9, a full dose of 12-60 mg is administered on days 1 and 15; and
   d) in cycle 10 and subsequent cycles, a full dose of 12-60 mg is administered on day 1.

18. The bispecific antibody according to embodiment 17, wherein the full dose is 24 mg or about 24 mg.

19. The bispecific antibody according to embodiment 17, wherein the full dose is 48 mg or about 48 mg.

20. The bispecific antibody according to any one of embodiments 1-19, wherein the bispecific antibody is administered subcutaneously.

21. The bispecific antibody according to any one of embodiments 1-20, wherein the CLL is relapsed and/or refractory CLL.

22. The bispecific antibody according to any one of embodiments 1-21, wherein the subject is intolerant to a BTK inhibitor.

23. The bispecific antibody according to any one of embodiments 1-22, wherein the subject has received at least two prior lines of antineoplastic therapy.

24. The bispecific antibody according to embodiment 23, wherein at least one of the at least two prior antineoplastic therapy comprises treatment with a BTK inhibitor.

25. The bispecific antibody according to any one of embodiments 1-24, wherein the CLL is refractory to a BTK inhibitor.

26. The bispecific antibody according to any one of embodiments 1-25, wherein the CLL relapsed during treatment with a BTK inhibitor.

27. The bispecific antibody according to any one of embodiments 21-26, wherein the subject has refractory and/or relapsed CLL after receiving the two prior antineoplastic therapies.

28. The bispecific antibody according to any one of embodiments 1-27, wherein the subject is treated with prophylaxis for cytokine release syndrome (CRS).

29. The bispecific antibody according to embodiment 28, wherein the prophylaxis comprises administering a corticosteroid to the subject.

30. The bispecific antibody according to any one of embodiment 28 or 29, wherein the corticosteroid is administered on the same day as the bispecific antibody.

31. The bispecific antibody according to embodiment 30, wherein the corticosteroid is further administered on the second, third, and fourth days after administering the bispecific antibody.

32. The bispecific antibody according to any one of embodiments 29-31, wherein the corticosteroid is prednisolone.

33. The bispecific antibody according to embodiment 32, wherein the prednisolone is administered at an intravenous dose of 100 mg, or equivalent thereof, including oral dose.

34. The bispecific antibody according to any one of embodiments 1-33, wherein the subject is administered premedication to reduce reactions to injections.

35. The bispecific antibody according to embodiment 34, wherein the premedication comprises an antihistamine.

36. The bispecific antibody according to embodiment 35, wherein the antihistamine is diphenhydramine.

37. The bispecific antibody according to embodiment 36, wherein the diphenhydramine is administered at an intravenous or oral dose of 50 mg, or equivalent thereof.

38. The bispecific antibody according to any one of embodiments 34-37, wherein the premedication comprises an antipyretic.

39. The bispecific antibody according to embodiment 38, wherein the antipyretic is acetaminophen.

40. The bispecific antibody according to embodiment 39, wherein the acetaminophen is administered at an oral dose of 560 to 1000 mg, or equivalent thereof.

41. The bispecific antibody according to any one of embodiments 34-40, wherein the premedication is administered on the same day as the bispecific antibody.

42. The bispecific antibody according to any one of embodiments 28-41, wherein the prophylaxis is administered during cycle 1.

43. The bispecific antibody according to any one of embodiments 34-42, wherein the premedication is administered during cycle 1.

44. The bispecific antibody according to embodiment 42 or 43, wherein the prophylaxis is administered during cycle 2 when the subject experiences CRS greater than grade 1 after the last administration of the bispecific antibody in cycle 1.

45. The bispecific antibody according to embodiment 44, wherein the prophylaxis is continued in a subsequent cycle, when in the last administration of the bispecific antibody of the previous cycle, the subject experiences CRS greater than grade 1.

46. The bispecific antibody according to any one of embodiments 34-45, wherein the premedication is administered during cycle 2.

47. The bispecific antibody according to embodiment 46, wherein the premedication is administered during subsequent cycles.

48. The bispecific antibody according to any one of embodiments 1-47, wherein the subject is administered antibiotics if the subject develops Grade 1 CRS.

49. The bispecific antibody according to any one of embodiments 1-47, wherein the subject is administered a vasopressor if the subject develops Grade 2 or Grade 3 CRS.
50. The bispecific antibody according to any one of embodiments 1-47, wherein the subject is administered at least two vasopressors if the subject develops Grade 4 CRS.
51. The bispecific antibody according to any one of embodiments 1-50, wherein the subject is administered tocilizumab if the subject develops Grade 2, Grade 3, or Grade 4 CRS.
52. The bispecific antibody according to embodiment 51, wherein the subject is further administered a steroid.
53. The bispecific antibody according to embodiment 52, wherein the steroid is dexamethasone.
54. The bispecific antibody according to embodiment 52, wherein the steroid is methylprednisolone.
55. The bispecific antibody according to any one of embodiments 51-54, wherein tocilizumab is switched to an anti-IL-6 antibody (e.g., siltuximab) if the subject is refractory to tocilizumab.
56. The bispecific antibody according to any one of embodiments 51-54, wherein tocilizumab is switched to an IL-1R antagonist (e.g., anakinra) if the subject is refractory to tocilizumab.
57. The bispecific antibody according to any one of embodiments 1-56, wherein the subject is treated with prophylaxis for tumor lysis syndrome (TLS).
58. The bispecific antibody according to embodiment 57, wherein the prophylaxis for TLS comprises administering one or more uric acid reducing agents prior to administration of the bispecific antibody.
59. The bispecific antibody according to embodiment 58, wherein the one or more uric acid reducing agents comprise rasburicase and/or allopurinol.
60. The bispecific antibody according to any one of embodiments 1-59, wherein the subject achieves a complete response, a partial response, or stable disease.
61. The bispecific antibody according to any one of embodiments 1-60, wherein:
    (i) the first antigen-binding region comprises VHCDR1, VHCDR2, and VHCDR3 comprising the amino acid sequences set forth in SEQ ID NOs: 1, 2, and 3, respectively, and VLCDR1, VLCDR2, and VLCDR3 comprising the amino acid sequences set forth in SEQ ID NO: 4, the sequence GTN, and SEQ ID NO: 5, respectively; and
    (ii) the second antigen-binding region comprises VHCDR1, VHCDR2, and VHCDR3 comprising the amino acid sequences set forth in SEQ ID NOs: 8, 9, and 10, respectively, and VLCDR1, VLCDR2, and VLCDR3 comprising the amino acid sequences set forth in SEQ ID NO: 11, the sequence DAS, and SEQ ID NO: 12, respectively.
62. The bispecific antibody according to any one of embodiments 1-61, wherein:
    (i) the first antigen-binding region comprises a VH region comprising the amino acid sequence of SEQ ID NO: 6, and the VL region comprising the amino acid sequence of SEQ ID NO: 7; and
    (ii) the second antigen-binding region comprises a VH region comprising the amino acid sequence of SEQ ID NO: 13, and the VL region comprising the amino acid sequence of SEQ ID NO: 14.
63. The bispecific antibody according to any one of embodiments 1-62, wherein the first binding arm of the bispecific antibody is derived from a humanized antibody, preferably from a full-length IgG1,λ (lambda) antibody.
64. The bispecific antibody according to embodiment 63, wherein the first binding arm of the bispecific antibody comprises a λ light chain constant region comprising the amino acid sequence set forth in SEQ ID NO: 22.
65. The bispecific antibody according to any one of embodiments 1-64, wherein the second binding arm of the bispecific antibody is derived from a human antibody, preferably from a full-length Ig 1κ (kappa) antibody.
66. The bispecific antibody according to embodiment 65, wherein the second binding arm comprises a κ light chain constant region comprising the amino acid sequence set forth in SEQ ID NO: 23.
67. The bispecific antibody according to any one of embodiments 1-66, wherein the bispecific antibody is a full-length antibody with a human IgG1 constant region.
68. The bispecific antibody according to any one of embodiments 1-67, wherein the bispecific antibody comprises an inert Fc region.
69. The bispecific antibody according to any one of embodiments 1-68, wherein the bispecific antibody comprises a first heavy chain and a second heavy chain, wherein in both the first and second heavy chains, the amino acids in the positions corresponding to positions L234, L235, and D265 in the human IgG1 heavy chain constant region of SEQ ID NO: 15 are F, E, and A, respectively.
70. The bispecific antibody according to any one of embodiments 1-69, wherein the bispecific antibody comprises a first heavy chain and a second heavy chain, wherein in the first heavy chain, the amino acid in the position corresponding to F405 in the human IgG1 heavy chain constant region of SEQ ID NO: 15 is L, and wherein in the second heavy chain, the amino acid in the position corresponding to K409 in the human IgG1 heavy chain constant region of SEQ ID NO: 15 is R, or vice versa.
71. The bispecific antibody according to any one of embodiments 1-70, wherein the bispecific antibody comprises a first heavy chain and a second heavy chain, wherein
    (i) in both the first and second heavy chains, the amino acids in the positions corresponding to positions L234, L235, and D265 in the human IgG1 heavy chain constant region of SEQ ID NO: 15 are F, E, and A, respectively, and
    (ii) in the first heavy chain, the amino acid in the position corresponding to F405 in the human IgG1 heavy chain constant region of SEQ ID NO: 15 is L, and wherein in the second heavy chain, the amino acid in the position corresponding to K409 in the human IgG1 heavy chain constant region of SEQ ID NO: 15 is R, or vice versa.
72. The bispecific antibody according to embodiment 71, wherein the bispecific antibody comprises heavy chain constant regions comprising the amino acid sequences of SEQ ID NOs: 19 and 20.
73. The bispecific antibody according to any one of embodiments 1-72, wherein the bispecific antibody comprises a heavy chain and a light chain comprising the amino acid sequences set forth in SEQ ID NOs: 24 and 25, respectively, and a heavy chain and a light chain comprising the amino acid sequences set forth in SEQ ID NOs: 26 and 27, respectively.
74. The bispecific antibody according to any one of embodiments 1-73, wherein the bispecific antibody comprises a heavy chain and a light chain consisting of the amino acid sequence of SEQ ID NOs: 24 and 25, respectively, and a heavy chain and a light chain consisting of the amino acid sequence of SEQ ID NOs: 26 and 27, respectively.

75. The bispecific antibody according to any one of embodiments 1-74, wherein the bispecific antibody is epcoritamab, or a biosimilar thereof.

The present disclosure is further illustrated by the following examples, which should not be construed as further limiting. The contents of all figures and all references, Genbank sequences, patents and published patent applications cited throughout this application are expressly incorporated herein by reference.

1a. A method of treating chronic lymphocytic leukemia (CLL) in a human subject, the method comprising administering to the subject a bispecific antibody comprising:
  (i) a first binding arm comprising a first antigen-binding region which binds to human CD3ε (epsilon) and comprises a variable heavy chain (VH) region and a variable light chain (VL) region, wherein the VH region comprises the CDR1, CDR2 and CDR3 sequences that are in the VH region sequence of SEQ ID NO: 6, and the VL region comprises the CDR1, CDR2 and CDR3 sequences that are in the VL region sequence of SEQ ID NO: 7; and
  (ii) a second binding arm comprising a second antigen-binding region which binds to human CD20 and comprises a VH region and a VL region, wherein the VH region comprises the CDR1, CDR2 and CDR3 sequences that are in the VH region sequence of SEQ ID NO: 13, and the VL region comprises the CDR1, CDR2 and CDR3 sequences that are in the VL region sequence of SEQ ID NO: 14;
    wherein the bispecific antibody is administered at a dose ranging from 12-60 mg in 28-day cycles.
2a. The method of embodiment 1a, wherein the bispecific antibody is administered at a dose of 24 mg.
3a. The method of embodiment 1a, wherein the bispecific antibody is administered at a dose of 48 mg.
4a. The method of any one of embodiments 1a-3a, wherein the bispecific antibody is administered once every week (weekly administration).
5a. The method of embodiment 4a, wherein the weekly administration is performed for 2.5 28-day cycles.
6a. The method of embodiment 4a or 5a, wherein after the weekly administration, the bispecific antibody is administered once every two weeks (biweekly administration).
7a. The method of embodiment 6a, wherein the biweekly administration is performed for six 28-day cycles.
8a. The method of embodiment 6a or 7a, wherein after the biweekly administration, the bispecific antibody is administered once every four weeks.
9a. The method of any one of embodiments 4a-8a, wherein prior to administering the first weekly dose of 12-60 mg, a priming dose of the bispecific antibody is administered in cycle 1 of the 28-day cycles.
10a. The method of embodiment 9a, wherein the priming dose is administered two weeks prior to administering the first weekly dose of 12-60 mg.
11a. The method of embodiment 9a or 10a, wherein the priming dose is in the range of 0.05-0.35 mg.
12a. The method of any one of embodiments 9a-11a, wherein said priming dose is 0.16 mg or about 0.16 mg.
13a. The method of any one of embodiments 9a-12a, wherein after administering the priming dose and prior to administering the first weekly dose of 12-60 mg, an intermediate dose of the bispecific antibody is administered.
14a. The method of embodiment 13, wherein the priming dose is administered on day 1 and the intermediate dose is administered on day 8 before the first weekly dose of 12-60 mg on days and 22 of cycle 1.

15a. The method of embodiment 13a or 14a, wherein said intermediate dose is in the range of 0.6-1.2 mg.
16a. The method of any one of embodiments 13a-15a, wherein said intermediate dose is 0.8 mg or about 0.8 mg.
17a. The method of any one of embodiments 13a-16a, wherein the bispecific antibody is administered in 28-day cycles, wherein:
  a) in cycle 1, a priming dose is administered on day 1, an intermediate dose on day 8, and a full dose of 12-60 mg on days 15 and 22;
  b) in cycles 2-3, a full dose of 12-60 mg is administered on days 1, 8, 15, and 22;
  c) in cycles 4-9, a full dose of 12-60 mg is administered on days 1 and 15; and
  d) in cycle 10 and subsequent cycles, a full dose of 12-60 mg is administered on day 1.
18a. The method of embodiment 17a, wherein the full dose is 24 mg or about 24 mg.
19a. The method of embodiment 17a, wherein the full dose is 48 mg or about 48 mg.
20a. The method of any one of embodiments 1a-19a, wherein the bispecific antibody is administered subcutaneously.
21a. The method of any one of embodiments 1a-20a, wherein the CLL is relapsed and/or refractory CLL.
22a. The method of any one of embodiments 1-21a, wherein the subject is intolerant to a BTK inhibitor.
23a. The method of any one of embodiments 1a-22a, wherein the subject has received at least two prior lines of antineoplastic therapy.
24a. The method of embodiment 23a, wherein at least one of the at least two prior antineoplastic therapy comprises treatment with a BTK inhibitor.
25a. The method of any one of embodiments 1a-24a, wherein the CLL is refractory to a BTK inhibitor.
26a. The method of any one of embodiments 1a-25a, wherein the CLL relapsed during treatment with a BTK inhibitor.
27a. The method of any one of embodiments 21a-26a, wherein the subject has refractory and/or relapsed CLL after receiving the two prior antineoplastic therapies.
28a. The method of any one of embodiments 1a-27a, wherein the subject is treated with prophylaxis for cytokine release syndrome (CRS).
29a. The method of embodiment 28a, wherein the prophylaxis comprises administering a corticosteroid to the subject.
30a. The method of embodiment 28a or 29a, wherein the corticosteroid is administered on the same day as the bispecific antibody.
31a. The method of embodiment 30a, wherein the corticosteroid is further administered on the second, third, and fourth days after administering the bispecific antibody.
32a. The method of any one of embodiments 29a-31a, wherein the corticosteroid is prednisolone.
33a. The method of embodiment 32a, wherein the prednisolone is administered at an intravenous dose of 100 mg, or equivalent thereof, including oral dose.
34a. The method of any one of embodiments 1a-33a, wherein the subject is administered premedication to reduce reactions to injections.
35a. The method of embodiment 34a, wherein the premedication comprises an antihistamine.
36a. The method of embodiment 35a, wherein the antihistamine is diphenhydramine.
37a. The method of embodiment 36a, wherein the diphenhydramine is administered at an intravenous or oral dose of 50 mg, or equivalent thereof.

38a. The method of any one of embodiments 34a-37a, wherein the premedication comprises an antipyretic.
39a. The method of embodiment 38, wherein the antipyretic is acetaminophen.
40a. The method of embodiment 39, wherein the acetaminophen is administered at an oral dose of 560 to 1000 mg, or equivalent thereof.
41a. The method of any one of embodiments 34a-40a, wherein the premedication is administered on the same day as the bispecific antibody.
42a. The method of any one of embodiments 28a-41a, wherein the prophylaxis is administered during cycle 1.
43a. The method of any one of embodiments 34a-42a, wherein the premedication is administered during cycle 1.
44a. The method of embodiment 42a or 43a, wherein the prophylaxis is administered during cycle 2 when the subject experiences CRS greater than grade 1 after the last administration of the bispecific antibody in cycle 1.
45a. The method of embodiment 44a, wherein the prophylaxis is continued in a subsequent cycle, when in the last administration of the bispecific antibody of the previous cycle, the subject experiences CRS greater than grade 1.
46a. The method of any one of embodiments 34a-45a, wherein the premedication is administered during cycle 2.
47a. The method of embodiment 46a, wherein the premedication is administered during subsequent cycles.
48a. The method of any one of embodiments 1a-47a, wherein the subject is administered antibiotics if the subject develops Grade 1 CRS.
49a. The method of any one of embodiments 1a-47a, wherein the subject is administered a vasopressor if the subject develops Grade 2 or Grade 3 CRS.
50a. The method of any one of embodiments 1a-47a, wherein the subject is administered at least two vasopressors if the subject develops Grade 4 CRS.
51a. The method of any one of embodiments 1a-50a, wherein the subject is administered tocilizumab if the subject develops Grade 2, Grade 3, or Grade 4 CRS.
52a. The method of embodiment 51a, wherein the subject is further administered a steroid.
53a. The method of embodiment 52a, wherein the steroid is dexamethasone.
54a. The method of embodiment 52a, wherein the steroid is methylprednisolone.
55a. The method of any one of embodiments 51a-54a, wherein tocilizumab is switched to an anti-IL-6 antibody (e.g., siltuximab) if the subject is refractory to tocilizumab.
56a. The method of any one of embodiments 51a-54a, wherein tocilizumab is switched to an IL-1R antagonist (e.g., anakinra) if the subject is refractory to tocilizumab.
57a. The method of any one of embodiments 1a-56a, wherein the subject is treated with prophylaxis for tumor lysis syndrome (TLS).
58a. The method of embodiment 57a, wherein the prophylaxis for TLS comprises administering one or more uric acid reducing agents prior to administration of the bispecific antibody.
59a. The method of embodiment 58a, wherein the one or more uric acid reducing agents comprise rasburicase and/or allopurinol.
60a. The method of any one of embodiments 1a-59a, wherein the subject achieves a complete response, a partial response, or stable disease.
61a. The method of any one of embodiments 1a-60a, wherein:
  (i) the first antigen-binding region comprises VHCDR1, VHCDR2, and VHCDR3 comprising the amino acid sequences set forth in SEQ ID NOs: 1, 2, and 3, respectively, and VLCDR1, VLCDR2, and VLCDR3 comprising the amino acid sequences set forth in SEQ ID NO: 4, the sequence GTN, and SEQ ID NO: 5, respectively; and
  (ii) the second antigen-binding region comprises VHCDR1, VHCDR2, and VHCDR3 comprising the amino acid sequences set forth in SEQ ID NOs: 8, 9, and 10, respectively, and VLCDR1, VLCDR2, and VLCDR3 comprising the amino acid sequences set forth in SEQ ID NO: 11, the sequence DAS, and SEQ ID NO: 12, respectively.
62a. The method of any one of embodiments 1a-61a, wherein:
  (i) the first antigen-binding region comprises a VH region comprising the amino acid sequence of SEQ ID NO: 6, and the VL region comprising the amino acid sequence of SEQ ID NO: 7; and
  (ii) the second antigen-binding region comprises a VH region comprising the amino acid sequence of SEQ ID NO: 13, and the VL region comprising the amino acid sequence of SEQ ID NO: 14.
63a. The method of any one of embodiments 1a-62a, wherein the first binding arm of the bispecific antibody is derived from a humanized antibody, preferably from a full-length IgG1,λ (lambda) antibody.
64a. The method of embodiment 63a, wherein the first binding arm of the bispecific antibody comprises a λ light chain constant region comprising the amino acid sequence set forth in SEQ ID NO: 22.
65a. The method of any one of embodiments 1a-64a, wherein the second binding arm of the bispecific antibody is derived from a human antibody, preferably from a full-length IgG1κ (kappa) antibody.
66a. The method of embodiment 65a, wherein the second binding arm comprises a κ light chain constant region comprising the amino acid sequence set forth in SEQ ID NO: 23.
67a. The method of any one of embodiments 1a-66a, wherein the bispecific antibody is a full-length antibody with a human IgG1 constant region.
68a. The method of any one of embodiments 1a-67a, wherein the bispecific antibody comprises an inert Fc region.
69a. The method of any one of embodiments 1a-68a, wherein the bispecific antibody comprises a first heavy chain and a second heavy chain, wherein in both the first and second heavy chains, the amino acids in the positions corresponding to positions L234, L235, and D265 in the human IgG1 heavy chain constant region of SEQ ID NO: 15 are F, E, and A, respectively.
70a. The method of any one of embodiments 1a-69a, wherein the bispecific antibody comprises a first heavy chain and a second heavy chain, wherein in the first heavy chain, the amino acid in the position corresponding to F405 in the human IgG1 heavy chain constant region of SEQ ID NO: 15 is L, and wherein in the second heavy chain, the amino acid in the position corresponding to K409 in the human IgG1 heavy chain constant region of SEQ ID NO: 15 is R, or vice versa.
71a. The method of any one of embodiments 1a-70a, wherein the bispecific antibody comprises a first heavy chain and a second heavy chain, wherein
  (i) in both the first and second heavy chains, the amino acids in the positions corresponding to positions L234, L235, and D265 in the human IgG1 heavy chain constant region of SEQ ID NO: 15 are F, E, and A, respectively, and (ii) in the first heavy chain, the amino acid in the position corresponding to F405 in the human IgG1 heavy chain constant region of SEQ ID NO: 15 is L, and wherein in the second heavy chain, the amino acid in the position corresponding to K409 in the human IgG1 heavy chain constant region of SEQ ID NO: 15 is R, or vice versa.

72a. The method of embodiment 71a, wherein the bispecific antibody comprises heavy chain constant regions comprising the amino acid sequences of SEQ ID NOs: 19 and 20.

73a. The method of any one of embodiments 1a-72a, wherein the bispecific antibody comprises a heavy chain and a light chain comprising the amino acid sequences set forth in SEQ ID NOs: 24 and 25, respectively, and a heavy chain and a light chain comprising the amino acid sequences set forth in SEQ ID NOs: 26 and 27, respectively.

74a. The method of any one of embodiments 1a-73a, wherein the bispecific antibody comprises a heavy chain and a light chain consisting of the amino acid sequence of SEQ ID NOs: 24 and 25, respectively, and a heavy chain and a light chain consisting of the amino acid sequence of SEQ ID NOs: 26 and 27, respectively.

75a. The method of any one of embodiments 1a-74a, wherein the bispecific antibody is epcoritamab, or a biosimilar thereof.

EXAMPLES

DuoBody-CD3xCD20

DuoBody-CD3xCD20 is a bsAb recognizing the T-cell antigen CD3 and the B-cell antigen CD20. DuoBody-CD3xCD20 triggers potent T-cell-mediated killing of CD20-expressing cells. DuoBody-CD3xCD20 has a regular IgG1 structure.

Two parental antibodies, IgG1-CD3-FEAL, a humanized IgG1λ, CD3ε-specific antibody having heavy and light chain sequences as listed in SEQ ID NOs: 24 and 25, respectively, and IgG1-CD20-FEAR, derived from human IgG1κ CD20-specific antibody 7D8 having heavy and light chain sequences as listed in SEQ ID NOs: 26 and 27, respectively, were manufactured as separate biological intermediates. Each parental antibody contains one of the complementary mutations in the CH3 domain required for the generation of DuoBody molecules (F405L and K409R, respectively). The parental antibodies comprised three additional mutations in the Fc region (L234F, L235E and D265A; FEA). The parental antibodies were produced in mammalian Chinese hamster ovary (CHO) cell lines using standard suspension cell cultivation and purification technologies. DuoBody-CD3xCD20 was subsequently manufactured by a controlled Fab-arm exchange (cFAE) process (Labrijn et al. 2013, Labrijn et al. 2014, Gramer et al. 2013). The parental antibodies are mixed and subjected to controlled reducing conditions. This leads to separation of the parental antibodies that, under re-oxidation, re-assemble. This way, highly pure preparations of DuoBody-CD3xCD20 (~93-95%) were obtained. After further polishing/purification, final product was obtained, close to 100% pure. The DuoBody-CD3xCD20 concentration was measured by absorbance at 280 nm, using the theoretical extinction coefficient $\varepsilon=1.597$ mL·mg$^{-1}$cm$^{-1}$. The product has received the international proprietary name of epcoritamab.

Epcoritamab is prepared (5 mg/mL or 60 mg/mL) as a sterile clear colorless to slightly yellow solution supplied as concentrate for solution for subcutaneous (SC) injection. Epcoritamab contains buffering and tonicifying agents. All excipients and amounts thereof in the formulated product are pharmaceutically acceptable for subcutaneous injection products. Appropriate doses are reconstituted to a volume of about 1 mL for subcutaneous injection.

Example 1: Epcoritamab-Induced Activation of CD4+ and CD8+ T Cells and Cytotoxicity of B Cells Obtained from CLL Patients Patients with CLL often have intrinsic T cell immune dysfunction which could potentially impact epcoritamab's anti-tumor activity. This experiment was performed to determine whether epcoritamab can activate T cells from CLL patients and induce cytotoxicity against B cells.

Briefly, commercially obtained CLL patient PBMCs were co-cultured with healthy donor (HD) PBMCs (ratio patient: healthy donor cells 1:5) and epcoritamab, or with bispecific antibodies containing either the CD3 arm, or the CD20 arm, and a non-binding control arm (bsIgG1-CD3xctrl, and bsIgG1-ctrlxCD20, respectively, wherein controls have the same format as epcoritamab (i.e. having an inert Fc), for 24 hours. The HD PBMCs were added to improve viability of the CLL patient-derived PBMCs and were labeled with CFSE to be able to distinguish them from the CLL patient-derived PBMCs. CD69 expression was used to evaluate (A) CD4+ and (B) CD8+ T-cell activation. B-cell viability (% CD4−CD8−CD22+ cells left) was analyzed as a measure for cytotoxicity induced by epcoritamab.

Figure 1B:
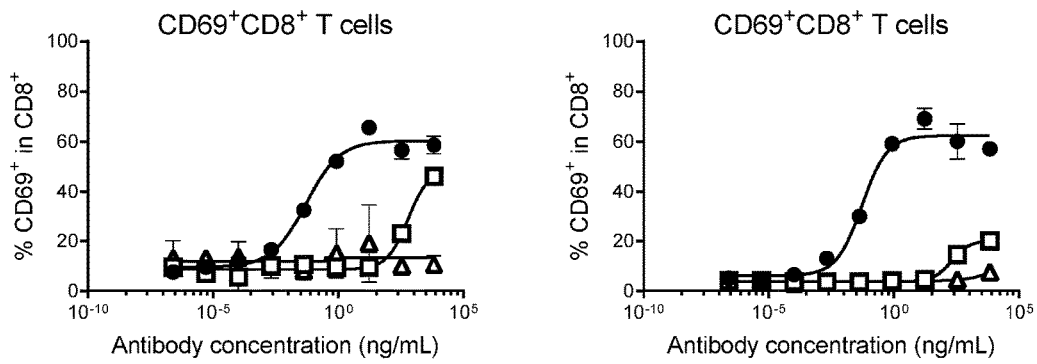
Figure 1C:
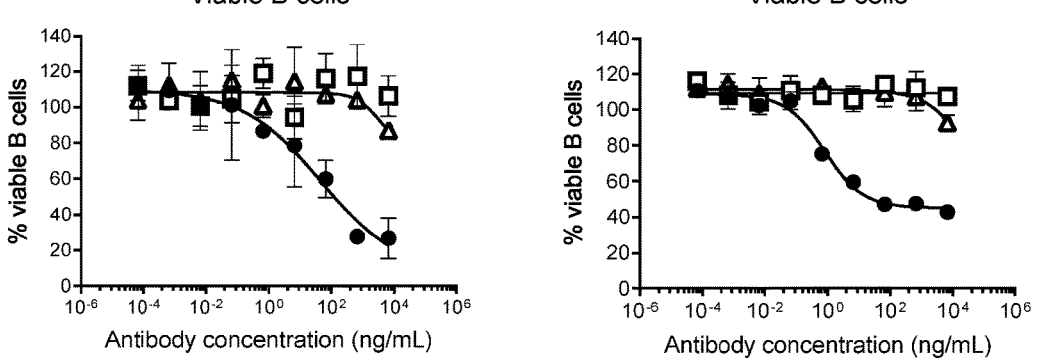

As shown in FIG. 1, epcoritamab induced the activation of both CLL and HD CD4+ and CD8+ T cells (See panels A and B). For CD4+ T cells, HD T cells were more efficiently activated than CLL T cells (see panel A, compare the left graph with the right graph, wherein epcoritamab induced CD4+ T cell activation to a higher % of CD69 in healthy donor derived PBMCs as compared to CLL patient derived PBMCs). Epcoritamab activated both CLL and HDD CD8+ T cells to a similar degree (see panel B, the upper line of both graphs represents epcoritamab). Epcoritamab induced T-cell-mediated cytotoxicity of both CLL and HD B cells, indicating that CLL B cells are susceptible to T-cell-mediated cytotoxicity (see panel C, wherein epcoritamab reduced the viability of B cells following a dose response curve). These data demonstrate that epcoritamab activates both CD4+ and CD8+ T cells, and induces killing of B cells, from CLL patients.

Example 2: A Phase 1b/2, Open-Label, Safety and Efficacy Study of Epcoritamab in Relapsed/Refractory Chronic Lymphocytic Leukemia An open-label, 2-part (dose escalation and expansion), multicenter study is conducted to evaluate the safety, tolerability, PK, pharmacodynamics, immunogenicity, and preliminary efficacy of single agent epcoritamab in subjects aged 18 years or older with relapsed and/or refractory (R/R) chronic lymphocytic leukemia (CLL).

Summary of Ongoing Clinical Trial with Epcoritamab

Epcoritamab is currently in a clinical trial for the treatment of R/R B-NHL (ClinicalTrials.gov Identifier: NCT03625037). Preliminary data suggest that the drug is tolerated at doses up to at least 48 mg, including 60 mg in R/R B-NHL patients, with a favourable safety profile, with no dose-limiting toxicities reported.

Objectives

Dose Escalation

The primary objective of the dose escalation part is to identify the recommended phase 2 dose (RP2D) and maximum tolerated dose (MTD) (endpoint: incidence of dose limiting toxicities (DLTs)), and evaluate the safety and tolerability (endpoints: incidence and severity of adverse events (AEs), serious adverse events (SAEs), CRS, ICANs, and TLS, and incidence of dose interruption, dose delay, and dose intensity), of epcoritamab in subjects with R/R CLL.

Secondary objectives of the dose escalation part include characterizing the PK properties of epcoritamab (endpoints: PK parameters, including clearance, volume of distribution and AUC0-last and AUC0-x, Cmax, Tmax, predose values, and half-life), evaluating pharmacodynamic markers linked to efficacy and the mechanism of action of epcoritamab (endpoints: pharmacodynamic markers in blood samples), evaluating the immunogenicity of epcoritamab (endpoint: incidence of anti-drug antibodies (ADAs) to epcoritamab), and assessing the preliminary anti-tumor activity of epcoritamab (endpoints: overall response rate (ORR), duration of response (DOR), time to response (TTR), progression free survival (PFS), and overall survival (OS)).

Exploratory objectives of the dose escalation part include evaluating biomarkers predictive of clinical response to epcoritamab (endpoints: CD20 expression, evaluation of immune populations, phenotype and function and blood) and assessing the minimal residual disease (MRD) status in peripheral blood and bone marrow (endpoint: incidence of undetectable MRD).

Expansion

The primary objective of the expansion part is to assess the preliminary efficacy of epcoritamab (endpoint: ORR).

Secondary objectives of the expansion part include evaluating the preliminary efficacy of epcoritamab (endpoints: DOR, TTR, PFS, and OS), assessing the MRD status in peripheral blood and bone marrow (endpoint: incidence of undetectable MRD), evaluating the safety and tolerability of epcoritamab (endpoints: endpoints: incidence and severity of AEs, SAEs, CRS, ICANs, and TLS, and incidence of dose interruption, dose delay, and dose intensity), establishing the PK and pharmacodynamic profiles of epcoritamab (endpoints: PK parameters and pharmacodynamic parameters), and evaluating immunogenicity of epcoritamab (endpoint: incidence of ADAs to epcoritamab).

Exploratory objectives of the expansion part include evaluating biomarkers predictive of clinical response to epcoritamab (endpoints: expression of CD20 and evaluation of immune populations, phenotype, and function, and blood).

Study Design Overview

Figure 2:
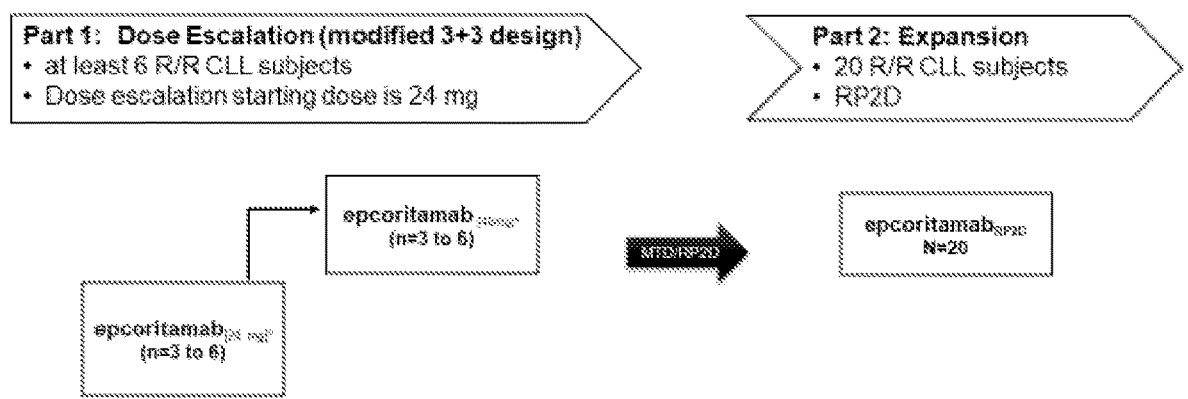
FIG. 2 is a schematic of the clinical trial design. *additional dose levels (higher or lower) may be explored. MTD: maximum tolerated dose, RP2D: recommended Phase 2 dose in R/R CLL subjects.

The trial is conducted in 2 parts: dose escalation (Part 1) and expansion (Part 2). A schematic of the overall trial design is shown in FIG. 2. Both parts consist of a screening period (up to 21 days prior to Cycle 1 Day 1), a treatment period (Cycle 1 Day 1 until epcoritamab discontinuation), a safety follow-up (60 days after the last dose of epcoritamab), and a survival status follow-up.

In both Part 1 and Part 2, epcoritamab is administered as a subcutaneous (SC) injection in 4-week cycles (i.e., 28 days), as shown below, until one or more of the discontinuation criteria are met:

Cycle 1-3: Days 1, 8, 15 and 22 (QW)
Cycle 4-9: Days 1 and 15 (Q2W)
Cycle 10 and beyond: Day 1 (Q4W)

A step-up dosing method is used to mitigate the potential for CRS: priming dose on Cycle 1 Day 1, followed by intermediate dose on Cycle 1 Day 8, then full dose on Cycle 1 Day 15 and Day 22, and full dose in subsequent cycles.

In Part 1 (Dose Escalation), epcoritamab is tested in subjects with R/R CLL using the modified 3+3 design. DLTs are evaluated during the first treatment cycle (i.e., 28 days). After identifying the RP2D, the preliminary efficacy of single agent epcoritamab is assessed together with safety, tolerability, pharmacokinetics (PK), pharmacodynamics, and biomarkers in Part 2 (Expansion).

Dose Escalation (Part 1)

The dose escalation part implements a modified 3+3 design. Epcoritamab is studied at 2 full dose levels: 24 mg and 48 mg. A step-up dosing regimen is applied: 0.16 mg/0.8 mg/24 mg and 0.16 mg/0.8 mg/48 mg (priming/intermediate/full dose). Additional doses including intermediate doses and dosing regimens may be explored based on emerging data. At each dose level, 3 subjects are initially treated. Based on the escalation rules specified following Table 3, 3 additional subjects may be needed at the current dose level or 3 subjects are treated at a different dose level. At least 6 subjects will be enrolled in Part 1. Subjects are monitored for DLTs during the first treatment cycle (i.e., 28 days).

TABLE 3

Escalation Rules Based on Number of Subjects with DLTs

| Decision, based on the number of subjects with DLTs ($N_{DLT}$) | Number of subjects evaluable for DLT at the current dose-level | |
| --- | --- | --- |
| | 3 | 6 |
| Escalate, if $N_{DLT} \leq$ | 0 | 1 |
| Remain on dose-level, if $N_{DLT} =$ | 1 | 2 |
| De-escalate, if $N_{DLT} \geq$ | 2 | 3 |
| Disallow dose-level, if $N_{DLT} \geq$ | 3 | 4 |

Subjects who are not DLT evaluable may be replaced, and at least 6 subjects are needed for a dose level to be identified as RP2D. Additional full dose levels, either lower than 24 mg (e.g., 12 mg) or higher than 48 mg (e.g., 60 mg), may be investigated.

After all subjects on a dose level have completed the DLT monitoring period (i.e., Cycle 1; 28 days), all available data will be evaluated (including, but not limited to safety, PK, pharmacodynamic, and immunogenicity data) in order to inform the next dose level.

Dose escalation stops when:
at the lowest dose-level to be investigated, the decision would be to disallow, de-escalate or remain on the same dose-level according to the escalation rules
at the highest dose-level to be investigated, the decision would be to escalate or remain on the same dose-level according to the escalation rules
at the current dose-level, the decision would be to escalate according to the escalation rules, but a higher dose-level has been evaluated which led to dose de-escalation, or the decision would be to de-escalate according to the escalation rules but a lower dose-level has been evaluated which led to dose escalation The MTD is defined as the highest investigated dose level with DLT observed in at most one-third of subjects. The RP2D for R/R CLL will be set at 48 mg if the dose level is found to be safe and tolerable. The totality of data, including safety (e.g., adverse events (AEs) and safety laboratory values, and observations made after the end of the DLT evaluation period), pharmacokinetics, pharmacodynamics, and preliminary efficacy, will guide further development for expansion.

Expansion (Part II)

Once the RP2D is established, the expansion part will begin. The expansion part enrolls approximately 20 subjects with R/R CLL previously treated with 2 prior lines of systemic antineoplastic therapy, including a BTK inhibitor (e.g., ibrutinib) or are otherwise intolerant of a BTK inhibitor. R/R CLL subjects are treated at the RP2D identified in Part 1. The primary efficacy endpoint of the expansion part is ORR as assessed using the iwCLL 2018 criteria (Table 2). ORR is a widely accepted response endpoint to evaluate the efficacy for subjects with R/R CLL. Secondary efficacy endpoints include DOR, TTR, PFS, and OS. Incidence of MRD negative status is also evaluated as a secondary efficacy endpoint. MRD assessment indicates how many cancer cells still remain in a subject who is in remission either during or after treatment has been implemented. Safety endpoints in the expansion part include the incidence and severity of AEs/SAEs, incidence and severity of tumor lysis syndrome (TLS), immune effector cell-associated neurotoxicity syndrome (ICANS) and CRS, and incidence of treatment interruption and delay.

Inclusion Criteria

1. Subjects must be at least 18 years of age.
2. Active CLL disease that needs treatment with at least 1 of the following criteria being met:
   a. Evidence of progressive marrow failure as manifested by the development of, or worsening of, anemia and/or thrombocytopenia
   b. Massive (i.e., ≥6 cm below the left costal margin) or progressive or symptomatic splenomegaly
   c. Massive nodes (i.e., ≥10 cm in longest diameter) or progressive or symptomatic lymphadenopathy
   d. Progressive lymphocytosis with an increase of ≥50% over a 2-month period, or lymphocyte doubling time (LDT)<6 months
   e. Autoimmune complications including anemia or thrombocytopenia poorly responsive to corticosteroids
   f. Symptomatic or functional extra nodal involvement (e.g., skin, kidney, lung, spine)
   g. Disease-related symptoms as defined by any of the following:
      Unintentional weight loss ≥10% within the previous 6 months
      Significant fatigue
      Fevers ≥38.0° C. (100.5° F.) for 2 or more weeks without evidence of infection.
      Night sweats for ≥1 month without evidence of infection
3. R/R CLL after receiving at least 2 prior lines of systemic antineoplastic therapy, including treatment with (or intolerance of) a BTK inhibitor (e.g., ibrutinib). Relapse is defined as evidence of disease progression in a subject who has previously achieved a CR or PR for ≥6 months. Refractory disease is defined as treatment failure (not achieving a CR or PR) or as progression within 6 months from the last dose of therapy.
4. Measurable Disease with at least one of the following criteria:
   a. ≥5×10$^9$/L (5,000/µL) B lymphocytes in peripheral blood
   b. Presence of measurable lymphadenopathy and/or organomegaly
5. ECOG performance status score of 0 or 1
6. Screening flow cytometry evidence of CD20 positivity
7. Has acceptable laboratory parameters as follows:

TABLE 4

| | Parameter | Result |
|---|---|---|
| a. | Creatine clearance or serum creatine | >45 mL/min (Cockcroft-Gault) or serum creatinine ≤1.5 times the upper limit of normal (×ULN) |
| b. | Serum alanine transaminase (ALT) | ≤2.5 × ULN |
| c. | Serum aspartate transaminase (AST) | ≤2.5 × ULN |
| d. | Bilirubin | ≤1.5 × ULN unless due to Gilbert syndrome Note: Subjects with Gilbert's syndrome may be included if total bilirubin is ≤3 × ULN and direct bilirubin is ≤1.5 × ULN |
| e. | Hemoglobin | ≥9.0 g/dL unless anemia is due to marrow involvement of CLL. Note: Blood transfusion may be administered during screening to meet this requirement |
| f. | Absolute neutrophil count | ≥1.0 × 10$^9$/L (1000/µL) unless neutropenia is due to bone marrow involvement of CLL. Note: Growth factor support is allowed in case of bone marrow involvement. |
| g. | Platelet count | ≥30 × 10$^9$/L (30,000/µL) Note: Transfusion may be administered during screening to meet this requirement. |
| h. | Coagulation status | PT/INR/aPTT ≤1.5 × ULN |

8. Received a cumulative dose of corticosteroids less than the equivalent of 250 mg of prednisone within the 2-week period before the first dose of epcoritamab
9. Subject must have availability of fresh bone marrow material at screening.
10. Must take prophylaxis for CRS/TLS.
11. Subject must be willing and able to adhere to the prohibitions and restrictions specified in the protocol.

Exclusion Criteria

1. Transformation of CLL to aggressive non-Hodgkin lymphoma
2. Subject received prior treatment with a CD3xCD20 bispecific antibody
3. Subject received any prior allogeneic HSCT or solid organ transplantation
4. Subject received treatment with an anti-cancer biologic including anti-CD20 therapy, radio-conjugated or toxin-conjugated antibody or CAR T-cell therapy within 4 weeks or 5 half-lives, whichever is shorter, before the first dose of epcoritamab.
5. Subject received chemotherapy or radiation therapy within 2 weeks of the first dose of epcoritamab.
6. Subject received treatment with an investigational drug or an invasive investigational medical device within 4 weeks or 5 half-lives, whichever is shorter, prior to the first dose of epcoritamab
7. Subject has autoimmune disease or other diseases that require permanent or high-dose immunosuppressive therapy
8. Subject has uncontrolled intercurrent illness, including but not limited to:
   a. Ongoing or active infection requiring intravenous antibiotics treatment at the time of enrollment or within the previous 2 weeks prior to the first dose of epcoritamab.
   b. Symptomatic congestive heart failure (grade III or IV as classified by the New York Heart Association), unstable angina pectoris or cardiac arrhythmia
   c. Myocardial infarction, intracranial bleed, or stroke within the past 6 months
9. Has a baseline QT interval at screening as corrected by Fridericia's formula (QTcF)>480 msec
10. Subject received vaccination with live vaccines within 28 days prior to the first dose of epcoritamab 11. Subject has toxicities from previous anti-cancer therapies that have not resolved to baseline levels or to Grade 1 or less except for alopecia and peripheral neuropathy
12. Subject has known CNS involvement at screening
13. Subject has known past or current malignancy other than inclusion diagnosis, except for:
    a. Cervical carcinoma of Stage 1B or less
    b. Non-invasive basal cell or squamous cell skin carcinoma
    c. Non-invasive, superficial bladder cancer
    d. Prostate cancer with a current PSA level <0.1 ng/mL
    e. Any curable cancer with a CR of >2 years duration
14. Subject has suspected allergies, hypersensitivity, or intolerance to epcoritamab or its excipients
15. Subject is unable to tolerate uric acid reducing medications
16. Subject has had major surgery (e.g., requiring general anesthesia) within 3 weeks before screening or will not have fully recovered from surgery, or has major surgery planned during the time the subject is expected to participate in the trial (or within 4 weeks after the last dose of epcoritamab); Note: Subjects with planned surgical procedures to be conducted under local anesthesia may participate.
17. Subject has known history/positive serology for hepatitis B (unless immune due to vaccination or resolved natural infection or unless passive immunization due to immunoglobulin therapy):
    a. Positive test for antibodies to the hepatitis B core antigen (anti-HBc) AND
    b. Negative test for antibodies to the hepatitis B surface antigen (anti-HBs).
18. Known medical history or ongoing hepatitis C infection that has not been cured.
19. Subject tests positive for HIV at screening.
20. Subject is a woman who is pregnant or breast-feeding, or who is planning to become pregnant while enrolled in this trial or within 12 months after the last dose of epcoritamab.
21. Subject is a man who plans to father a child while enrolled in this trial or within 12 months after the last dose of epcoritamab.
22. Subject has any condition for which participation would not be in the best interest of the subject (e.g., compromise the well-being) or that could prevent, limit, or confound the protocol-specified assessments.

Premedication and CRS Prophylaxis

Administration of corticosteroids, antihistamines, and antipyretics for four days is performed to reduce/prevent the severity of symptoms from potential CRS for each dose of epcoritamab in cycle 1. For administration of epcoritamab in Cycle 2 and beyond, CRS prophylaxis with corticosteroids is optional. Corticosteroid administration can be either intravenous or oral route with recommended dose or equivalent.

TABLE 5

Prophylactic corticosteroid administration pre- and post-epcoritamab administration

| | | | Corticosteroids | Antihistamines | Antipyretics |
|---|---|---|---|---|---|
| Cycle 1 | 1$^{st}$ epcoritamab administration (priming dose) | Day 01* | Prednisolone 100 mg IV (or equivalent including oral dose) | Diphenhydramine 50 mg IV or oral (PO) (or equivalent) | Paracetamol (acetaminophen) 650 to 1000 mg PO (or equivalent) |
| | | Day 02 | Prednisolone 100 mg IV (or equivalent including oral dose) | | |
| | | Day 03 | Prednisolone 100 mg IV (or equivalent including oral dose) | | |
| | | Day 04 | Prednisolone 100 mg IV (or equivalent including oral dose) | | |
| | 2$^{nd}$ epcoritamab administration (intermediate dose) | Day 08* | Prednisolone 100 mg IV (or equivalent including oral dose) | Diphenhydramine 50 mg IV or oral (PO) (or equivalent) | Paracetamol (acetaminophen) 650 to 1000 mg PO (or equivalent) |
| | | Day 09 | Prednisolone 100 mg IV (or equivalent including oral dose) | | |
| | | Day 10 | Prednisolone 100 mg IV (or equivalent including oral dose) | | |
| | | Day 11 | Prednisolone 100 mg IV (or equivalent including oral dose) | | |
| | 3$^{rd}$ epcoritamab administration (1$^{st}$ full dose) | Day 15* | Prednisolone 100 mg IV (or equivalent including oral dose) | Diphenhydramine 50 mg IV or oral (PO) (or equivalent) | Paracetamol (acetaminophen) 650 to 1000 mg PO (or equivalent) |
| | | Day 16 | Prednisolone 100 mg IV (or equivalent including oral dose) | | |
| | | Day 17 | Prednisolone 100 mg IV (or equivalent including oral dose) | | |
| | | Day 18 | Prednisolone 100 mg IV (or equivalent including oral dose) | | |

TABLE 5-continued

Prophylactic corticosteroid administration pre- and post-epcoritamab administration

|  |  |  | Corticosteroids | Antihistamines | Antipyretics |
|---|---|---|---|---|---|
|  | 4th epcoritamab administration (2nd full dose) | Day 22* | Prednisolone 100 mg IV (or equivalent including oral dose) | Diphenhydramine 50 mg IV or oral (PO) (or equivalent) | Paracetamol (acetaminophen) 650 to 1000 mg PO (or equivalent) |
|  |  | Day 23 | Prednisolone 100 mg IV (or equivalent including oral dose) |  |  |
|  |  | Day 24 | Prednisolone 100 mg IV (or equivalent including oral dose) |  |  |
|  |  | Day 25 | Prednisolone 100 mg IV (or equivalent including oral dose) |  |  |
| Cycle 2 | 5th epcoritamab administration (3rd full dose) | Day 29* Day 30 Day 31 Day 32 | If CRS ≥grade 2 occurs following the 4th epcoritamab administration, 4-day consecutive corticosteroid administration is continued in Cycle 2 until an epcoritamab dose is given that does not result in subsequent CRS. | Optional | Optional |

*30 minutes - 2 hours prior to administration of epcoritamab.

TABLE 6

Corticosteroid Dose Equivalents - Conversion Table

| Glucocorticoid | Approximate equivalent dose (mg) |
|---|---|
| Short-acting | |
| Cortisone (PO) | 500 |
| Hydrocortisone (IV or PO) | 400 |
| Intermediate-acting | |
| Methylprednisolone (IV or PO) | 80 |
| Prednisolone (PO) | 100 |
| Prednisone (IV or PO) | 100 |
| Triamcinolone (IV) | 80 |
| Long-acting | |
| Betamethasone (IV) | 15 |
| Dexamethasone (IV or PO) | 15 |

Supportive Care for Cytokine Release Syndrome

CRS is graded according to the ASTCT grading for CRS (Tables 7 and 8), and for treatment of CRS, subjects should receive supportive care. Supportive care can include, but is not limited to, Infusion of saline Systemic glucocorticosteroid, antihistamine, antipyrexia Support for blood pressure (vasopressin, vasopressors)

Support for low-flow and high-flow oxygen and positive pressure ventilation

Monoclonal antibody against IL-6R, e.g., IV administration of tocilizumab

Monoclonal antibody against IL-6, e.g., IV siltuximab if not responding to repeated tocilizumab.

TABLE 7

Grading and Management of Cytokine Release Syndrome
Harmonized definitions and grading criteria for CRS, per the American
Society for Transplantation and Cellular Therapy (ASTCT), formerly American
Society for Blood and Marrow Transplantation, (ASBMT), are presented below.
Grading of Cytokine Release Syndrome

| CRS parameter | Grade 1 | Grade 2 | Grade 3 | Grade 4 | Grade 5 |
|---|---|---|---|---|---|
| Fever[1] With hypotension | ≥38.0° C. None | ≥38.0° C. Not requiring vasopressors | ≥38.0° C. Requiring 1 vasopressor with or without vasopressin | ≥38.0° C. Requiring ≥2 vasopressors (excluding vasopressin) | Death due to CRS in which another cause is not the principle factor leading to this outcome |
| And/or hypoxia[2] | None | Requiring low-flow (□6 L/minute) nasal cannula or blow-by | Requiring high-flow (>6 L/minute) nasal cannula, facemask, nonrebreather mask, or | Requiring positive pressure ventilation[3] (eg, CPAP, BiPAP, intubation and | |

TABLE 7-continued

Grading and Management of Cytokine Release Syndrome
Harmonized definitions and grading criteria for CRS, per the American
Society for Transplantation and Cellular Therapy (ASTCT), formerly American
Society for Blood and Marrow Transplantation, (ASBMT), are presented below.
Grading of Cytokine Release Syndrome

| CRS parameter | Grade 1 | Grade 2 | Grade 3 | Grade 4 | Grade 5 |
|---|---|---|---|---|---|
| | | | venturi mask | mechanical ventilation) | |

Abbreviations:
BiPAP, Bilevel positive airway pressure;
CPAP, continuous positive airway pressure;
CRS, cytokine release syndrome;
IV, intravenous.
Note:
organ toxicities or constitutional symptoms associated with CRS may be graded according to CTCAE but they do not influence CRS grading.
[1]Fever is defined as temperature ≥38.0° C. not attributable to any other cause, with or without constitutional symptoms (eg, myalgia, arthralgia, malaise). In subjects who have CRS receiving antipyretics, anticytokine therapy, and/or corticosteroids, fever is no longer required to grade subsequent CRS severity. In this case, CRS grading is driven by hypotension and/or hypoxia.
[2]CRS grade is determined by the more severe event: hypotension or hypoxia not attributable to any other cause. For example, a subject with temperature of 39.5° C., hypotension requiring 1 vasopressor, and hypoxia requiring low-flow nasal cannula is classified as grade 3 CRS. Both systolic blood pressure and mean arterial pressure are acceptable for blood pressure measurement. No specific limits are required, but hypotension should be determined on a case-by-case basis, accounting for age and the subject's individual baseline, i.e., a blood pressure that is below the normal expected for an individual in a given environment.
[3]Intubation of a subject without hypoxia for the possible neurologic compromise of a patent airway alone or for a procedure is not by definition grade 4 CRS.
Source: Adapted from Lee et al., *Biol Blood Marrow Transplant* 2019; 25: 625-638

TABLE 8

Grading and Management of Cytokine Release Syndrome

| CRS grade | Management |
|---|---|
| 1 | Fever: Patients with a new fever should be admitted to the hospital if not already. Investigate for infection and rapidly startup broad-spectrum antibiotics. Continuation of antibiotic therapy is recommended until and potential neutropenia resolve. Constitutional symptoms may be helped by NSAIDs.<br>Tocilizumab: No*.<br>Steroids: No. |
| 2 | Fever: As per grade 1.<br>Hypotension: Immediate clinical evaluation and intervention is warranted. At the first confirmed decrease ≥20% from baseline systolic, diastolic or mean arterial pressure or evidence of worsening perfusion, administer an IV fluid bolus (20 mL/kg up to 1 L). Consider a vasopressor and administer no later than after the 3$^{rd}$ IV fluid bolus due the vasodilatation and capillary leak associated with CRS.<br>Hypoxia: Consider X-ray or CT-scan if hypoxic and/or tachypneic. Administer oxygen by low-flow nasal cannula (≤6 L/min) or blow-by.<br>Tocilizumab: No* (yes, if the patient has comorbidities†).<br>Steroids: No (consider, if the patient has comorbidities‡). |
| 3 | Fever: As per grade 1.<br>Hypotension: Immediate clinical evaluation and intervention is warranted. Administer a vasopressor (norepinephrine), with or without vasopressin, as most patients with CRS have peripheral vasodilation.<br>Hypoxia: Administer oxygen by high-flow nasal cannula (>6 L/min), facemask, non-breather mask, or Venturi mask.<br>Tocilizumab: Yes†.<br>Steroids: Consider‡. |
| 4 | Fever: As per grade 1.<br>Hypotension: Immediate clinical evaluation and intervention is warranted. Administer at least 2 vasopressors, with or without vasopressin, as most patients with CRS have peripheral vasodilation. |

TABLE 8-continued

Grading and Management of Cytokine Release Syndrome

| CRS grade | Management |
|---|---|
| | Hypoxia: Positive pressure (e.g. CPAP, BiPAP, intubation, and mechanical ventilation).<br>Tocilizumab: Yes[†].<br>Steroids: Yes[‡]. |

*Consider intervening earlier in specific cases. For example, an elderly patient with prolonged fever (>72 hours) or very high fever (>40.5° C./104.9° F.) may not tolerate the resulting sinus tachycardia as well as a younger patient, so tocilizumab may be indicated.
[†]Tocilizumab (anti-IL-6R) remains the only first-line anticytokine therapy approved for CRS. If there is no improvement in symptoms within 6 hours, or if the patient starts to deteriorate after initial improvement, a second dose of tocilizumab should be administered along with a dose of corticosteroids. For patients being refractory to tocilizumab (3 administrations), additional anticytokine therapy such as siltuximab (anti-IL-6) or anakinra (anti-IL-1R) may be considered. However, such use is entirely anecdotal and, as such, is entirely at the discretion of the treating physician.
[‡]Consider dexamethasone over methylprednisolone due to improved CNS penetration even in absence of neurotoxicity, as high-grade CRS is correlated with risk of concurrent or subsequent ICANS. If concurrent ICANS is observed, dexamethasone should be preferred.
Source: (Varadarajan I, Kindwall-Keller T L, Lee D W (2020). Management of cytokine release syndrome. In: Chimeric antigen receptor T-cell therapies for cancer (Chapter 5). Elsevier 2020)

Tumor Lysis Syndrome Prevention and Management

For prophylactic treatment of tumor lysis syndrome, subjects receive uric acid reducing agents prior to the administration of epcoritamab, with allopurinol given at least 72 hours prior to the first dose of epcoritamab and rasburicase initiated prior to starting epcoritamab. Increased oral hydration should be received prior to the first dose and is maintained during dosings. Reassessment of the subject's TLS risk category is performed prior to subsequent doses.

Study Assessments

Bone Marrow Assessment

A fresh bone marrow aspirate is obtained at screening (i.e., within 21 days prior to Cycle 1 Day 1) and at the time of complete response (CR) or when clinically indicated. A fresh bone marrow biopsy is obtained at screening and at the time of CR or nodular partial response (PR) (nPR) or when clinically indicated. Bone marrow evaluations include morphological examination and either flow cytometry or immunohistochemistry. A bone marrow biopsy with aspirate is obtained (a) to confirm a CR or nPR that is supported by physical examination findings, laboratory evaluations and radiographic evaluations according to iwCLL guidelines (Hallek et al, Lancet 2018; 391:1524-37), and (b) if progression is only shown in 1 parameter to confirm cytopenic progression (i.e., neutropenia, anemia, and/or thrombocytopenia and to distinguish from autoimmune and treatment-related cytopenias).

Radiographic Assessments

Imaging scans of the neck, chest, abdomen and pelvis are performed at screening (i.e., within 3 weeks prior to the first dose of epcoritamab) and subsequent response assessments. A CT scan with contrast is the recommended imaging modality. MRI may be used only if CT with contrast is medically contraindicated or if the frequency of CT scans exceeds local standards. MRI studies do not replace the required neck, chest, abdomen, and pelvic CT scans. Additional imaging assessments may be performed to support the efficacy evaluations for a subject as necessary.

Bone Marrow Assessment

A fresh bone marrow aspirate is obtained at screening (i.e., within 21 days prior to Cycle 1 Day 1) and at the time of CR or as clinically indicated. A fresh bone marrow biopsy is obtained at screening and at the time of CR or nodular PR (nPR) or as clinically indicated. Bone marrow evaluations include a morphological examination and either flow cytometry or immunohistochemistry. A bone marrow biopsy with aspirate is obtained (a) to confirm a CR or nPR according to iwCLL guidelines (Hallek et al., supra) that is supported by physical examination findings, laboratory evaluations and radiographic evaluations, and (b) if progression is only shown in 1 parameter to confirm cytopenic progression (i.e., neutropenia, anemia, and/or thrombocytopenia and to distinguish from autoimmune and treatment-related cytopenias).

Minimal Residual Disease (MRD) Assessment

MRD is assessed in the blood by flow cytometry and next generation sequencing. After start of treatment, blood samples are requested at the fixed time points and at time of CR. As an exploratory analysis, when a subject reaches a CR, a portion of the aspirate collected to confirm CR is used to assess MRD.

Disease Response and Progressive Disease Assessment

Tumor response according to imaging assessment is performed to inform decisions on continuation of treatment. Response assessment is completed according to the revised iwCLL guidelines for diagnosis, indications for treatment, response assessment and supportive management of CLL, as described in Table 2. Endpoint definitions are as follows:

Overall response rate (ORR), is defined as the proportion of subjects who achieve a response of PR or CR, prior to initiation of subsequent therapy.

Time to response (TTR), is defined among responders, as the time between first dose of epcoritamab and the initial documentation of PR or CR.

Duration of response (DOR), is defined among responders, as the time from the initial documentation of PR or CR to the date of disease progression or death, whichever occurs earlier.

Progression-free survival (PFS), is defined as the time from the first dosing date of epcoritamab and the date of disease progression or death, whichever occurs earlier.

Overall survival (OS), is defined as the time from the first dosing date of epcoritamab and the date of death.

MRD negativity rate, is defined as the proportion of subjects with at least 1 undetectable MRD result according to the specific threshold, prior to initiation of subsequent therapy.

Clinical Safety Assessments

Safety will be assessed by measuring adverse events, laboratory test results, ECGs, vital sign measurements, physical examination findings, and ECOG performance status. Also assessed are immune effector cell-associated neurotoxicity syndrome (e.g., as described by Lee et al., Biol Blood Marrow Transplant 2019; 25:625-638), constitutional symptoms (B symptoms), tumor flare reaction, and survival.

Immunophenotyping Analyses

Absolute B and T-cell counts are determined in fresh whole blood using flow cytometry to monitor changes associated with epcoritamab treatment. The T-cell activation and exhaustion phenotype is evaluated using flow cytometry and markers in order to evaluate the association of such markers with drug target engagement, treatment efficacy, and/or safety of epcoritamab. Additional immunophenotypes of circulating immune cells (e.g., levels of regulatory T-cells which can suppress T-cell function) are determined in fresh whole blood using flow cytometry to evaluate the association of such markers with T-cell activation/exhaustion phenotype, subject response, and epcoritamab's MOA.

Cytokine and Endothelial Activation Marker Analyses

Since T-cell activation following initial epcoritamab administrations may lead to cytokine release causing CRS, cytokine levels are closely monitored. The levels of cytokines, such as IL-2, IL15, IL-6, IL-8, IL-10, IFNγ, and/or TNFα, are measured in plasma samples using an array based ligand binding assay. Additional cytokines may also be determined to evaluate the association of such markers with treatment-emergent AEs and outcome to epcoritamab.

Preliminary Results:

The first patient was enrolled on Nov. 30, 2020. As of Jul. 1, 2021, 7 patients with R/R CLL received epcoritamab subcutaneously administered at 2 full-dose levels: 24 (n=3) and 48 mg (n=4). Six patients completed the dose limiting toxicity (DLT) evaluation period, and 5 patients had a response assessment. Patients had received a median of 4 lines of prior therapy (range, 2-5). Six of 7 patients had poor-risk features of del(17p), TP53 mutations, or both. Three of 7 pts had bulky disease. No DLTs occurred at 24 or 48 mg. The most common treatment-emergent AEs (>30%) were cytokine release syndrome (CRS) (100%), fatigue (71%), injection-site reaction (43%), and nausea (43%). All pts experienced CRS in the first cycle, but no CRS events were higher than grade 2. No cases of immune effector cell-associated neurotoxicity syndrome (ICANS) were observed. Despite presence of circulating tumor cells, tumor lysis syndrome (TLS) was not observed. Antileukemic activity has been observed at both dose levels, with partial responses in 3 of 5 patients.

As of Sep. 8, 2021, a total of 11 R/R CLL patients have received epcoritamab at 24 mg (N=3) and 48 mg (N=8).

Epcoritamab was well tolerated at both 24 mg and 48 mg with the most common treatment-emergent adverse events being CRS, fatigue, and injection site reaction. There was no immune effector cell-associated neurotoxicity syndrome (ICANS). Preliminary activity of epcoritamab in these heavily pretreated patients who had high-risk cytogenetics have been observed. Among 6 response-evaluable subjects, there were 1 non-confirmed partial response (nPR) at 24 mg and 2 partial responses (PR) at 48 mg. These data are preliminary and non-validated and unclean data and response data were not completely entered by site.

CONCLUSION

These preliminary data suggest that epcoritamab is well tolerated in patients with R/R CLL at dose levels up to 48 mg and has encouraging clinical activity in pts with high-risk disease.

TABLE 9

Listing of Sequences

| SEQ ID | Description | Sequence |
|---|---|---|
| 1 | huCD3 VH CDR1 | GFTFNTYA |
| 2 | huCD3 VH CDR2 | IRSKYNNYAT |
| 3 | huCD3 VH CDR3 | VRHGNFGNSYVSWFAY |
| 4 | huCD3 VL CDR1 | TGAVTTSNY |
| — | huCD3 VL CDR2 | GTN |
| 5 | huCD3 VL CDR3 | ALWYSNLWV |
| 6 | huCD3 VH1 | EVKLVESGGGLVQPGGSLRLSCAASGFTFNTYAMNWVRQAPGKGLEWVARIRSKYNNYATYYADSVKDRFTISRDDSKSSLYLQMNNLKTEDTAMYYCVRHGNFGNSYVSWFAYWGQGTLVTVSS |
| 7 | huCD3 VL1 | QAVVTQEPSFSVSPGGTVTLTCRSSTGAVTTSNYANWVQQTPGQAFRGLIGGTNKRAPGVPARFSGSLIGDKAALTITGAQADDESIYFCALWYSNLWVFGGGTKLTVL |
| 8 | VH CD20-7D8 CDR1 | GFTFHDYA |
| 9 | VH CD20-7D8 CDR2 | ISWNSGTI |
| 10 | VH CD20-7D8 CDR3 | AKDIQYGNYYYGMDV |
| 11 | VL CD20-7D8 CDR1 | QSVSSY |
| — | VL CD20-7D8 CDR2 | DAS |
| 12 | VL CD20-7D8 CDR3 | QQRSNWPIT |
| 13 | VH CD20-7D8 | EVQLVESGGGLVQPDRSLRLSCAASGFTFHDYAMHWVRQAPGKGLEWVSTISWINSGTIGYADSVKGRFTISRDNAKNSLYLQMNSLRAEDTALYYCAKDIQYGNYYYGMDVWGQGTTVTVSS |
| 14 | VL CD20-7D8 | EIVLTQSPATLSLSPGERATLSCRASQSVSSYLAWYQQKPGQAPRLLIYDASNRATGIPARFSGSGSGTDFTLTISSLEPEDFAVYYCQQRSNWPITFGQGTRLEIK |
| 15 | IgG1 heavy chain constant region-WT (amino acids positions 118-447 according to EU numbering). CH3 region italics | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |

TABLE 9-continued

Listing of Sequences

| SEQ ID | Description | Sequence |
|---|---|---|
| 16 | IgG1-LFLEDA Heavy chain constant region (amino acids positions 118-447 according to EU numbering). | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEFEGGPSVFLFPPKPKDTLMISRTPEVTCVVVAVSHEDPEVKFNWYVDGVEVHNAKTPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 17 | IgG1 F405L (amino acids positions 118-447 according to EU numbering) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFLLYSKLTVDKSRWQQGNVFSCSVMHEALHNHYTQKSLSLSPG |
| 18 | IgG1-K409R (amino acids positions 118-447 according to EU numbering) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSRLTVDKSRWQQGNVFSCSVMHEALHNHYTQKSLSLSPG |
| 19 | IgG1-LFLEDA-F405L (FEAL) (amino acids positions 118-447 according to EU numbering) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEFEGGPSVFLFPPKPKDTLMISRTPEVTCVVVAVSHEDPEVKFNWYVDGVEVHNAKTPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFLLYSKLTVDKSRWQQGNVFSCSVMHEALHNHYTQKSLSLSPG |
| 20 | IgG1-LFLEDA-K409R (FEAR) (amino acids positions 118-447 according to EU numbering) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEFEGGPSVFLFPPKPKDTLMISRTPEVTCVVVAVSHEDPEVKFNWYVDGVEVHNAKTPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSRLTVDKSRWQQGNVFSCSVMHEALHNHYTQKSLSLSPG |
| 21 | IgG1 CH3 region | GQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 22 | Constant region human lambda LC | GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| 23 | Constant region human kappa LC | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 24 | huCD3-LFLEDA-F405L (FEAL) heavy chain | EVKLVESGGGLVQPGGSLRLSCAASGFTFNTYAMNWVRQAPGKGLEWVARIRSKYNNYATYYADSVKDRFTISRDDSKSSLYLQMNNLKTEDTAMYYCVRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEFEGGPSVFLFPPKPKDTLMISRTPEVTCVVVAVSHEDPEVKFNWYVDGVEVHNAKTPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFLLYSKLTVDKSRWQQGNVFSCSVMHEALHNHYTQKSLSLSPG |
| 25 | huCD3 VL + CL light chain | QAVVTQEPSFSVSPGGTVTLTCRSSTGAVTTSNYANWVQQTPGQAFRGLIGGTNKRAPGVPARFSGSLIGDKAALTITGAQADDESIYFCALWYSNLWVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |

TABLE 9-continued

Listing of Sequences

| SEQ ID | Description | Sequence |
|---|---|---|
| 26 | CD20-7D8-LFLEDA-K409R (FEAR) heavy chain | EVQLVESGGGLVQPDRSLRLSCAASGFTFHDYAMHWVRQAPGKGLEWVSTISWNSGTIGYADSVKGRFTISRDNAKNSLYLQMNSLRAEDTALYYCAKDIQYGNYYYGMDVWGQGTTVTVSSASTKGPSVFPLAPSSKSTSGGTAALGCLVKDYFPEPVTVSWNSGALTSGVHTFPAVLQSSGLYSLSSVVTVPSSLGTQTYICNVNHKPSNTKVDKRVEPKSCDKTHTCPPCPAPEFEGGPSVFLFPPKPKDTLMISRTPEVTCVVVAVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSRLTVDKSRWQQGNVFSCSVMHEALHNHYTQKSLSLSPG |
| 27 | CD20-7D8 VL + CL light chain | EIVLTQSPATLSLSPGERATLSCRASQSVSSYLAWYQQKPGQAPRLLIYDASNRATGIPARFSGSGSGTDFTLTISSLEPEDFAVYYCQQRSNWPITFGQGTRLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 28 | Human CD3 (epsilon) | MQSGTHWRVLGLCLLSVGVWGQDGNEEMGGITQTPYKVSISGTTVILTCPQYPGSEILWQHNDKNIGGDEDDKNIGSDEDHLSLKEFSELEQSGYYVCYPRGSKPEDANFYLYLRARVCENCMEMDVMSVATIVIVDICITGGLLLLVYYWSKNRKAKAKPVTRGAGAGGRQRGQNKERPPPVPNPDYEPIRKGQRDLYSGLNQRRI |
| 29 | Human CD20 | MTTPRNSVNGTFPAEPMKGPIAMQSGPKPLFRRMSSLVGPTQSFFMRESKTLGAVQIMNGLFHIALGGLLMIPAGIYAPICVTVWYPLWGGIMYIISGSLLAATEKNSRKCLVKGKMIMNSLSLFAAISGMILSIMDILNIKISHFLKMESLNFIRAHTPYINIYNCEPANPSEKNSPSTQYCYSIQSLFLGILSVMLIFAFFQELVIAGIVENEWKRTCSRPKSNIVLLSAEEKKEQTIEIKEEVVGLTETSSQPKNEEDIEIIPIQEEEEEETETNFPEPPQDQESSPIENDSSP |

Bold and underlined are FE; A; L and R, corresponding to positions 234 and 235; 265; 405 and 409, respectively, said positions being in accordance with EU-numbering. In variable regions, said CDR regions that were annotated in accordance with IMGT definitions are underlined.

We claim:

1. A method of treating chronic lymphocytic leukemia (CLL) in a human subject, the method comprising subcutaneously administering to the subject a bispecific antibody comprising:
   (i) a first binding arm comprising a first antigen-binding region which binds to human CD3ε (epsilon) and comprises a variable heavy chain (VH) region and a variable light chain (VL) region, wherein the VH region comprises the CDR1, CDR2 and CDR3 sequences that are in the VH region sequence of SEQ ID NO: 6, and the VL region comprises the CDR1, CDR2 and CDR3 sequences that are in the VL region sequence of SEQ ID NO: 7; and
   (ii) a second binding arm comprising a second antigen-binding region which binds to human CD20 and comprises a VH region and a VL region, wherein the VH region comprises the CDR1, CDR2 and CDR3 sequences that are in the VH region sequence of SEQ ID NO: 13, and the VL region comprises the CDR1, CDR2 and CDR3 sequences that are in the VL region sequence of SEQ ID NO: 14;
   wherein the bispecific antibody is administered at a full dose ranging from 12-60 mg in 28-day cycles, and wherein a priming dose of the bispecific antibody is administered on day 1 of cycle 1, and an intermediate dose of the bispecific antibody is administered on day 8 of cycle 1 before administration of the first full dose of the bispecific antibody on day 15 of cycle 1, wherein the priming dose and intermediate dose are at a lower dose as compared with the full dose; and
   wherein administration of the full dose of the bispecific antibody continues at least until the subject exhibits a complete response (CR), a partial response (PR) or stable disease, or until progressive disease develops or unacceptable toxicity occurs.

2. The method of claim 1, wherein after administration of the priming dose and the intermediate dose the bispecific antibody is administered at a full dose of 24 mg.

3. The method of claim 1, wherein after administration of the priming dose and the intermediate dose the bispecific antibody is administered at a full dose of 48 mg.

4. The method of claim 1, wherein the bispecific antibody is administered once every week (weekly administration) for 2.5 28-day cycles.

5. The method of claim 4, wherein after the weekly administration, the bispecific antibody is administered once every two weeks (biweekly administration) for six 28-day cycles.

6. The method of claim 5, wherein after the biweekly administration, the bispecific antibody is administered once every four weeks.

7. The method of claim 1, wherein the priming dose is in the range of 0.05-0.35 mg.

8. The method of claim 1, wherein said priming dose is 0.16 mg or about 0.16 mg.

9. The method of claim 1, wherein said intermediate dose is in the range of 0.6-1.2 mg.

10. The method of claim 1, wherein said intermediate dose is 0.8 mg or about 0.8 mg.

11. The method of claim 1, wherein the bispecific antibody is administered in 28-day cycles, wherein:
    a) in cycle 1, a priming dose is administered on day 1, an intermediate dose on day 8, and a full dose of 12-60 mg on days 15 and 22;
    b) in cycles 2-3, a full dose of 12-60 mg is administered on days 1, 8, 15, and 22;
    c) in cycles 4-9, a full dose of 12-60 mg is administered on days 1 and 15; and
    d) in cycle 10 and subsequent cycles, a full dose of 12-60 mg is administered on day 1.

12. The method of claim 11, wherein the full dose is 24 mg or about 24 mg.

13. The method of claim 11, wherein the full dose is 48 mg or about 48 mg.

14. The method of claim 1, wherein the CLL is relapsed and/or refractory CLL.

15. The method of claim 1, wherein the subject is intolerant to a BTK inhibitor or wherein the subject has received at least two prior lines of antineoplastic therapy.

16. The method of claim 1, wherein the CLL is refractory to a BTK inhibitor or wherein the CLL relapsed during treatment with a BTK inhibitor.

17. The method of claim 1, wherein the subject has refractory and/or relapsed CLL after receiving the two prior antineoplastic therapies.

18. The method of claim 1, wherein:
    (i) the first antigen-binding region comprises a VH region comprising the amino acid sequence of SEQ ID NO: 6, and a VL region comprising the amino acid sequence of SEQ ID NO: 7; and
    (ii) the second antigen-binding region comprises a VH region comprising the amino acid sequence of SEQ ID NO: 13, and a VL region comprising the amino acid sequence of SEQ ID NO: 14.

19. The method of claim 1, wherein the first binding arm of the bispecific antibody is derived from a humanized antibody and comprises a λ light chain constant region comprising the amino acid sequence set forth in SEQ ID NO: 22 and/or the second binding arm of the bispecific antibody is derived from a human antibody and comprises a κ light chain constant region comprising the amino acid sequence set forth in SEQ ID NO: 23.

20. The method of claim 1, wherein the bispecific antibody is a full-length antibody with a human IgG1 constant region.

21. The method of claim 1, wherein the bispecific antibody comprises a first heavy chain and a second heavy chain, wherein
    (i) in both the first and second heavy chains, the amino acids in the positions corresponding to positions L234, L235, and D265 in the human IgG1 heavy chain constant region of SEQ ID NO: 15 are F, E, and A, respectively, and/or
    (ii) in the first heavy chain, the amino acid in the position corresponding to F405 in the human IgG1 heavy chain constant region of SEQ ID NO: 15 is L, and wherein in the second heavy chain, the amino acid in the position corresponding to K409 in the human IgG1 heavy chain constant region of SEQ ID NO: 15 is R, or vice versa.

22. The method of claim 1, wherein the bispecific antibody comprises heavy chain constant regions comprising the amino acid sequences of SEQ ID NOs: 19 and 20.

23. The method of claim 1, wherein the bispecific antibody comprises a first heavy chain and a first light chain comprising the amino acid sequences set forth in SEQ ID NOs: 24 and 25, respectively, and a second heavy chain and a second light chain comprising the amino acid sequences set forth in SEQ ID NOs: 26 and 27, respectively.

24. The method of claim 1, wherein the bispecific antibody is epcoritamab, or a biosimilar thereof, wherein the biosimilar comprises:
    (i) a first binding arm comprising a VH region comprising the CDR1, CDR2 and CDR3 sequences that are in the VH region sequence of SEQ ID NO: 6, and a VL region comprising the CDR1, CDR2 and CDR3 sequences that are in the VL region sequence of SEQ ID NO: 7; and
    (ii) a second binding arm comprising a VH region comprising the CDR1, CDR2 and CDR3 sequences that are in the VH region sequence of SEQ ID NO: 13, and a VL region comprising the CDR1, CDR2 and CDR3 sequences that are in the VL region sequence of SEQ ID NO: 14.

25. A method of treating chronic lymphocytic leukemia (CLL) in a human subject, the method comprising subcutaneously administering to the subject a bispecific antibody comprising:
    a first heavy chain and a first light chain comprising the amino acid sequences set forth in SEQ ID NOs: 24 and 25, respectively, and a second heavy chain and a second light chain comprising the amino acid sequences set forth in SEQ ID NOs: 26 and 27, respectively, wherein the bispecific antibody is administered at a dose ranging from 12-60 mg in 28-day cycles, wherein:
    a) in cycle 1, a priming dose of 0.16 mg is administered on day 1, an intermediate dose of 0.8 mg on day 8, and a full dose of 12-60 mg on days 15 and 22;
    b) in cycles 2-3, a full dose of 12-60 mg is administered on days 1, 8, 15, and 22;
    c) in cycles 4-9, a full dose of 12-60 mg is administered on days 1 and 15; and
    d) in cycle 10 and subsequent cycles, a full dose of 12-60 mg is administered on day 1.

26. A method of treating chronic lymphocytic leukemia (CLL) in a human subject, the method comprising subcutaneously administering epcoritamab to the subject at a dose ranging from 12-60 mg in 28-day cycles, wherein:
    a) in cycle 1, a priming dose of 0.16 mg is administered on day 1, an intermediate dose of 0.8 mg on day 8, and a full dose of 12-60 mg on days 15 and 22;
    b) in cycles 2-3, a full dose of 12-60 mg is administered on days 1, 8, 15, and 22;

c) in cycles 4-9, a full dose of 12-60 mg is administered on days 1 and 15; and d) in cycle 10 and subsequent cycles, a full dose of 12-60 mg is administered on day 1, wherein administration of the full dose of the bispecific antibody continues at least until the subject exhibits a complete response (CR), a partial response (PR) or stable disease, or until progressive disease develops or unacceptable toxicity occurs.

27. The method of claim 26, wherein the full dose of epcoritamab is 24 mg.

28. The method of claim 26, wherein the full dose of epcoritamab is 48 mg.

* * * * *

```
                       SEQUENCE LISTING

<160> NUMBER OF SEQ ID NOS: 29

<210> SEQ ID NO 1
<211> LENGTH: 8
<212> TYPE: PRT
<213> ORGANISM: Artificial sequence
<220> FEATURE:
<223> OTHER INFORMATION: CDR sequence

<400> SEQUENCE: 1

Gly Phe Thr Phe Asn Thr Tyr Ala
1               5

<210> SEQ ID NO 2
<211> LENGTH: 10
<212> TYPE: PRT
<213> ORGANISM: Artificial sequence
<220> FEATURE:
<223> OTHER INFORMATION: CDR sequence

<400> SEQUENCE: 2

Ile Arg Ser Lys Tyr Asn Asn Tyr Ala Thr
1               5                   10

<210> SEQ ID NO 3
<211> LENGTH: 16
<212> TYPE: PRT
<213> ORGANISM: Artificial sequence
<220> FEATURE:
```

<223> OTHER INFORMATION: CDR sequence

<400> SEQUENCE: 3

Val Arg His Gly Asn Phe Gly Asn Ser Tyr Val Ser Trp Phe Ala Tyr
1               5                   10                  15

<210> SEQ ID NO 4
<211> LENGTH: 9
<212> TYPE: PRT
<213> ORGANISM: Artificial sequence
<220> FEATURE:
<223> OTHER INFORMATION: CDR sequence

<400> SEQUENCE: 4

Thr Gly Ala Val Thr Thr Ser Asn Tyr
1               5

<210> SEQ ID NO 5
<211> LENGTH: 9
<212> TYPE: PRT
<213> ORGANISM: Artificial sequence
<220> FEATURE:
<223> OTHER INFORMATION: CDR sequence

<400> SEQUENCE: 5

Ala Leu Trp Tyr Ser Asn Leu Trp Val
1               5

<210> SEQ ID NO 6
<211> LENGTH: 125
<212> TYPE: PRT
<213> ORGANISM: Artificial sequence
<220> FEATURE:
<223> OTHER INFORMATION: Heavy chain variable region sequence 1

<400> SEQUENCE: 6

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 7
<211> LENGTH: 109
<212> TYPE: PRT
<213> ORGANISM: Artificial sequence
<220> FEATURE:
<223> OTHER INFORMATION: Light chain variable region sequence

<400> SEQUENCE: 7

Gln Ala Val Val Thr Gln Glu Pro Ser Phe Ser Val Ser Pro Gly Gly
1               5                   10                  15

```
Thr Val Thr Leu Thr Cys Arg Ser Ser Thr Gly Ala Val Thr Thr Ser
             20                  25                  30

Asn Tyr Ala Asn Trp Val Gln Gln Thr Pro Gly Gln Ala Phe Arg Gly
             35                  40                  45

Leu Ile Gly Gly Thr Asn Lys Arg Ala Pro Gly Val Pro Ala Arg Phe
         50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                 85                  90                  95

Leu Trp Val Phe Gly Gly Gly Thr Lys Leu Thr Val Leu
            100                 105
```

<210> SEQ ID NO 8
<211> LENGTH: 8
<212> TYPE: PRT
<213> ORGANISM: Artificial sequence
<220> FEATURE:
<223> OTHER INFORMATION: CDR sequence

<400> SEQUENCE: 8

```
Gly Phe Thr Phe His Asp Tyr Ala
1               5
```

<210> SEQ ID NO 9
<211> LENGTH: 8
<212> TYPE: PRT
<213> ORGANISM: Artificial sequence
<220> FEATURE:
<223> OTHER INFORMATION: CDR sequence

<400> SEQUENCE: 9

```
Ile Ser Trp Asn Ser Gly Thr Ile
1               5
```

<210> SEQ ID NO 10
<211> LENGTH: 15
<212> TYPE: PRT
<213> ORGANISM: Artificial sequence
<220> FEATURE:
<223> OTHER INFORMATION: CDR sequence

<400> SEQUENCE: 10

```
Ala Lys Asp Ile Gln Tyr Gly Asn Tyr Tyr Tyr Gly Met Asp Val
1               5                   10                  15
```

<210> SEQ ID NO 11
<211> LENGTH: 6
<212> TYPE: PRT
<213> ORGANISM: Artificial sequence
<220> FEATURE:
<223> OTHER INFORMATION: CDR sequence

<400> SEQUENCE: 11

```
Gln Ser Val Ser Ser Tyr
1               5
```

<210> SEQ ID NO 12
<211> LENGTH: 9
<212> TYPE: PRT
<213> ORGANISM: Artificial sequence
<220> FEATURE:
<223> OTHER INFORMATION: CDR sequence

```
<400> SEQUENCE: 12

Gln Gln Arg Ser Asn Trp Pro Ile Thr
1               5

<210> SEQ ID NO 13
<211> LENGTH: 122
<212> TYPE: PRT
<213> ORGANISM: Artificial sequence
<220> FEATURE:
<223> OTHER INFORMATION: Heavy chain variable region sequence

<400> SEQUENCE: 13

Glu Val Gln Leu Val Glu Ser Gly Gly Gly Leu Val Gln Pro Asp Arg
1               5                   10                  15

Ser Leu Arg Leu Ser Cys Ala Ala Ser Gly Phe Thr Phe His Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser
        115                 120

<210> SEQ ID NO 14
<211> LENGTH: 107
<212> TYPE: PRT
<213> ORGANISM: Artificial sequence
<220> FEATURE:
<223> OTHER INFORMATION: Light chain variable region sequence

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 15
<211> LENGTH: 329
<212> TYPE: PRT
<213> ORGANISM: Homo Sapiens

<400> SEQUENCE: 15

Ala Ser Thr Lys Gly Pro Ser Val Phe Pro Leu Ala Pro Ser Ser Lys
```

```
            1               5                  10                 15
          Ser Thr Ser Gly Gly Thr Ala Ala Leu Gly Cys Leu Val Lys Asp Tyr
                      20                  25                  30

Phe Pro Glu Pro Val Thr Val Ser Trp Asn Ser Gly Ala Leu Thr Ser
                      35                  40                  45

Gly Val His Thr Phe Pro Ala Val Leu Gln Ser Ser Gly Leu Tyr Ser
                      50                  55                  60

Leu Ser Ser Val Val Thr Val Pro Ser Ser Leu Gly Thr Gln Thr
           65                  70                  75                  80

Tyr Ile Cys Asn Val Asn His Lys Pro Ser Asn Thr Lys Val Asp Lys
                              85                  90                  95

Arg Val Glu Pro Lys Ser Cys Asp Lys Thr His Thr Cys Pro Pro Cys
                          100                 105                 110

Pro Ala Pro Glu Leu Leu Gly Gly Pro Ser Val Phe Leu Phe Pro Pro
                          115                 120                 125

Lys Pro Lys Asp Thr Leu Met Ile Ser Arg Thr Pro Glu Val Thr Cys
                      130                 135                 140

Val Val Val Asp Val Ser His Glu Asp Pro Glu Val Lys Phe Asn Trp
           145                 150                 155                 160

Tyr Val Asp Gly Val Glu Val His Asn Ala Lys Thr Lys Pro Arg Glu
                              165                 170                 175

Glu Gln Tyr Asn Ser Thr Tyr Arg Val Val Ser Val Leu Thr Val Leu
                          180                 185                 190

His Gln Asp Trp Leu Asn Gly Lys Glu Tyr Lys Cys Lys Val Ser Asn
                          195                 200                 205

Lys Ala Leu Pro Ala Pro Ile Glu Lys Thr Ile Ser Lys Ala Lys Gly
                      210                 215                 220

Gln Pro Arg Glu Pro Gln Val Tyr Thr Leu Pro Pro Ser Arg Glu Glu
           225                 230                 235                 240

Met Thr Lys Asn Gln Val Ser Leu Thr Cys Leu Val Lys Gly Phe Tyr
                              245                 250                 255

Pro Ser Asp Ile Ala Val Glu Trp Glu Ser Asn Gly Gln Pro Glu Asn
                          260                 265                 270

Asn Tyr Lys Thr Thr Pro Pro Val Leu Asp Ser Asp Gly Ser Phe Phe
                          275                 280                 285

Leu Tyr Ser Lys Leu Thr Val Asp Lys Ser Arg Trp Gln Gln Gly Asn
                      290                 295                 300

Val Phe Ser Cys Ser Val Met His Glu Ala Leu His Asn His Tyr Thr
           305                 310                 315                 320

Gln Lys Ser Leu Ser Leu Ser Pro Gly
                              325

<210> SEQ ID NO 16
<211> LENGTH: 329
<212> TYPE: PRT
<213> ORGANISM: Artificial sequence
<220> FEATURE:
<223> OTHER INFORMATION: Heavy chain constant region

<400> SEQUENCE: 16

Ala Ser Thr Lys Gly Pro Ser Val Phe Pro Leu Ala Pro Ser Ser Lys
           1               5                  10                  15

Ser Thr Ser Gly Gly Thr Ala Ala Leu Gly Cys Leu Val Lys Asp Tyr
                      20                  25                  30

Phe Pro Glu Pro Val Thr Val Ser Trp Asn Ser Gly Ala Leu Thr Ser
```

```
                35                  40                  45
Gly Val His Thr Phe Pro Ala Val Leu Gln Ser Ser Gly Leu Tyr Ser
             50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
                100                 105                 110

Pro Ala Pro Glu Phe Glu Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 17
<211> LENGTH: 329
<212> TYPE: PRT
<213> ORGANISM: Artificial sequence
<220> FEATURE:
<223> OTHER INFORMATION: Heavy chain constant region

<400> SEQUENCE: 17

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
                 35                  40                  45

Gly Val His Thr Phe Pro Ala Val Leu Gln Ser Ser Gly Leu Tyr Ser
             50                  55                  60

Leu Ser Ser Val Val Thr Val Pro Ser Ser Ser Leu Gly Thr Gln Thr
```

Tyr Ile Cys Asn Val Asn His Lys Pro Ser Asn Thr Lys Val Asp Lys
65                  70                  75                  80

Arg Val Glu Pro Lys Ser Cys Asp Lys Thr His Thr Cys Pro Pro Cys
            85                  90                  95

Pro Ala Pro Glu Leu Leu Gly Gly Pro Ser Val Phe Leu Phe Pro Pro
100                 105                 110

Lys Pro Lys Asp Thr Leu Met Ile Ser Arg Thr Pro Glu Val Thr Cys
        115                 120                 125

Val Val Val Asp Val Ser His Glu Asp Pro Glu Val Lys Phe Asn Trp
130                 135                 140

Tyr Val Asp Gly Val Glu Val His Asn Ala Lys Thr Lys Pro Arg Glu
145                 150                 155                 160

Glu Gln Tyr Asn Ser Thr Tyr Arg Val Val Ser Val Leu Thr Val Leu
            165                 170                 175

His Gln Asp Trp Leu Asn Gly Lys Glu Tyr Lys Cys Lys Val Ser Asn
180                 185                 190

Lys Ala Leu Pro Ala Pro Ile Glu Lys Thr Ile Ser Lys Ala Lys Gly
        195                 200                 205

Gln Pro Arg Glu Pro Gln Val Tyr Thr Leu Pro Pro Ser Arg Glu Glu
210                 215                 220

Met Thr Lys Asn Gln Val Ser Leu Thr Cys Leu Val Lys Gly Phe Tyr
225                 230                 235                 240

Pro Ser Asp Ile Ala Val Glu Trp Glu Ser Asn Gly Gln Pro Glu Asn
            245                 250                 255

Asn Tyr Lys Thr Thr Pro Pro Val Leu Asp Ser Asp Gly Ser Phe Leu
260                 265                 270

Leu Tyr Ser Lys Leu Thr Val Asp Lys Ser Arg Trp Gln Gln Gly Asn
        275                 280                 285

Val Phe Ser Cys Ser Val Met His Glu Ala Leu His Asn His Tyr Thr
290                 295                 300

Gln Lys Ser Leu Ser Leu Ser Pro Gly
305                 310

<210> SEQ ID NO 18
<211> LENGTH: 329
<212> TYPE: PRT
<213> ORGANISM: Artificial sequence
<220> FEATURE:
<223> OTHER INFORMATION: Heavy chain constant region

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

```
              100                 105                 110
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Arg Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 19
<211> LENGTH: 329
<212> TYPE: PRT
<213> ORGANISM: Artificial sequence
<220> FEATURE:
<223> OTHER INFORMATION: Heavy chain constant region

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
```

```
                130                 135                 140
Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Leu
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 20
<211> LENGTH: 329
<212> TYPE: PRT
<213> ORGANISM: Artificial sequence
<220> FEATURE:
<223> OTHER INFORMATION: Heavy chain constant region

<400> SEQUENCE: 20

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Phe Glu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                 165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
            245                 250                 255
Pro Ser Asp Ile Ala Val Glu Trp Glu Ser Asn Gly Gln Pro Glu Asn
        260                 265                 270
Asn Tyr Lys Thr Thr Pro Pro Val Leu Asp Ser Asp Gly Ser Phe Phe
    275                 280                 285
Leu Tyr Ser Arg Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly
            325

<210> SEQ ID NO 21
<211> LENGTH: 106
<212> TYPE: PRT
<213> ORGANISM: Homo sapiens

<400> SEQUENCE: 21

Gly Gln Pro Arg Glu Pro Gln Val Tyr Thr Leu Pro Pro Ser Arg Glu
1               5                  10                  15
Glu Met Thr Lys Asn Gln Val Ser Leu Thr Cys Leu Val Lys Gly Phe
            20                  25                  30
Tyr Pro Ser Asp Ile Ala Val Glu Trp Glu Ser Asn Gly Gln Pro Glu
        35                  40                  45
Asn Asn Tyr Lys Thr Thr Pro Pro Val Leu Asp Ser Asp Gly Ser Phe
    50                  55                  60
Phe Leu Tyr Ser Lys Leu Thr Val Asp Lys Ser Arg Trp Gln Gln Gly
65                  70                  75                  80
Asn Val Phe Ser Cys Ser Val Met His Glu Ala Leu His Asn His Tyr
                85                  90                  95
Thr Gln Lys Ser Leu Ser Leu Ser Pro Gly
            100                 105

<210> SEQ ID NO 22
<211> LENGTH: 106
<212> TYPE: PRT
<213> ORGANISM: Homo sapiens

<400> SEQUENCE: 22

Gly Gln Pro Lys Ala Ala Pro Ser Val Thr Leu Phe Pro Pro Ser Ser
1               5                  10                  15
Glu Glu Leu Gln Ala Asn Lys Ala Thr Leu Val Cys Leu Ile Ser Asp
            20                  25                  30
Phe Tyr Pro Gly Ala Val Thr Val Ala Trp Lys Ala Asp Ser Ser Pro
        35                  40                  45
Val Lys Ala Gly Val Glu Thr Thr Thr Pro Ser Lys Gln Ser Asn Asn
```

```
                50                  55                  60
Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 23
<211> LENGTH: 107
<212> TYPE: PRT
<213> ORGANISM: Homo sapiens

<400> SEQUENCE: 23

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 24
<211> LENGTH: 454
<212> TYPE: PRT
<213> ORGANISM: Artificial sequence
<220> FEATURE:
<223> OTHER INFORMATION: Antibody heavy chain

<400> SEQUENCE: 24

Glu Val Lys Leu Val Glu Ser Gly Gly Gly Leu Val Gln Pro Gly Gly
 1               5                  10                  15

Ser Leu Arg Leu Ser Cys Ala Ser Gly Phe Thr Phe Asn Thr Tyr
                20                  25                  30

Ala Met Asn Trp Val Arg Gln Ala Pro Gly Lys Gly Leu Glu Trp Val
             35                  40                  45

Ala Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Ser Ser
 65                  70                  75                  80

Leu Tyr Leu Gln Met Asn Asn Leu Lys Thr Glu Asp Thr Ala Met Tyr
                 85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160
```

-continued

```
Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Phe Glu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Ala Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Leu Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly
    450

<210> SEQ ID NO 25
<211> LENGTH: 215
<212> TYPE: PRT
<213> ORGANISM: Artificial sequence
<220> FEATURE:
<223> OTHER INFORMATION: Antibody light chain

<400> SEQUENCE: 25

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60
```

```
Ser Gly Ser Leu Ile Gly Asp Lys Ala Ala Leu Thr Ile Thr Gly Ala
 65                  70                  75                  80

Gln Ala Asp Asp Glu Ser Ile Tyr Phe Cys Ala Leu Trp Tyr Ser Asn
                 85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 26
<211> LENGTH: 451
<212> TYPE: PRT
<213> ORGANISM: Artificial sequence
<220> FEATURE:
<223> OTHER INFORMATION: Antibody heavy chain

<400> SEQUENCE: 26

Glu Val Gln Leu Val Glu Ser Gly Gly Gly Leu Val Gln Pro Asp Arg
1               5                   10                  15

Ser Leu Arg Leu Ser Cys Ala Ala Ser Gly Phe Thr Phe His Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205
```

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Ala Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 27
<211> LENGTH: 214
<212> TYPE: PRT
<213> ORGANISM: Artificial sequence
<220> FEATURE:
<223> OTHER INFORMATION: Antibody light chain

<400> SEQUENCE: 27

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys Arg Thr Val Ala Ala
            100                 105                 110

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 28
<211> LENGTH: 207
<212> TYPE: PRT
<213> ORGANISM: Homo Sapiens

<400> SEQUENCE: 28

```
Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
50                  55                  60

Asn Ile Gly Gly Asp Glu Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205
```

<210> SEQ ID NO 29
<211> LENGTH: 297
<212> TYPE: PRT
<213> ORGANISM: Homo Sapiens

<400> SEQUENCE: 29

```
Met Thr Thr Pro Arg Asn Ser Val Asn Gly Thr Phe Pro Ala Glu Pro
1               5                   10                  15
```

-continued

```
Met Lys Gly Pro Ile Ala Met Gln Ser Gly Pro Lys Pro Leu Phe Arg
            20                  25                  30
Arg Met Ser Ser Leu Val Gly Pro Thr Gln Ser Phe Phe Met Arg Glu
        35                  40                  45
Ser Lys Thr Leu Gly Ala Val Gln Ile Met Asn Gly Leu Phe His Ile
    50                  55                  60
Ala Leu Gly Gly Leu Leu Met Ile Pro Ala Gly Ile Tyr Ala Pro Ile
65                  70                  75                  80
Cys Val Thr Val Trp Tyr Pro Leu Trp Gly Gly Ile Met Tyr Ile Ile
                85                  90                  95
Ser Gly Ser Leu Leu Ala Ala Thr Glu Lys Asn Ser Arg Lys Cys Leu
            100                 105                 110
Val Lys Gly Lys Met Ile Met Asn Ser Leu Ser Leu Phe Ala Ala Ile
            115                 120                 125
Ser Gly Met Ile Leu Ser Ile Met Asp Ile Leu Asn Ile Lys Ile Ser
    130                 135                 140
His Phe Leu Lys Met Glu Ser Leu Asn Phe Ile Arg Ala His Thr Pro
145                 150                 155                 160
Tyr Ile Asn Ile Tyr Asn Cys Glu Pro Ala Asn Pro Ser Glu Lys Asn
                165                 170                 175
Ser Pro Ser Thr Gln Tyr Cys Tyr Ser Ile Gln Ser Leu Phe Leu Gly
            180                 185                 190
Ile Leu Ser Val Met Leu Ile Phe Ala Phe Phe Gln Glu Leu Val Ile
            195                 200                 205
Ala Gly Ile Val Glu Asn Glu Trp Lys Arg Thr Cys Ser Arg Pro Lys
            210                 215                 220
Ser Asn Ile Val Leu Leu Ser Ala Glu Glu Lys Lys Glu Gln Thr Ile
225                 230                 235                 240
Glu Ile Lys Glu Glu Val Val Gly Leu Thr Glu Thr Ser Ser Gln Pro
                245                 250                 255
Lys Asn Glu Glu Asp Ile Glu Ile Ile Pro Ile Gln Glu Glu Glu Glu
            260                 265                 270
Glu Glu Thr Glu Thr Asn Phe Pro Glu Pro Pro Gln Asp Gln Glu Ser
            275                 280                 285
Ser Pro Ile Glu Asn Asp Ser Ser Pro
    290                 295
```